US010767189B2

(12) United States Patent
Coulibaly et al.

(10) Patent No.: US 10,767,189 B2
(45) Date of Patent: Sep. 8, 2020

(54) METHODS FOR PRODUCING COTTON PLANTS WITH ENHANCED DROUGHT TOLERANCE AND COMPOSITIONS THEREOF

(71) Applicant: Monsanto Technology LLC, St. Louis, MO (US)

(72) Inventors: Issa Coulibaly, St. Peters, MO (US); Nilesh Dighe, Lubbock, TX (US); Xuehui Feng, St. Louis, MO (US); Richard H. Sheetz, Prosper, TX (US); Humphrey W. Wanjugi, O'Fallon, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 91 days.

(21) Appl. No.: 15/237,136

(22) Filed: Aug. 15, 2016

(65) Prior Publication Data

US 2017/0051302 A1 Feb. 23, 2017

Related U.S. Application Data

(60) Provisional application No. 62/218,923, filed on Sep. 15, 2015, provisional application No. 62/206,695, filed on Aug. 18, 2015.

(51) Int. Cl.

| | |
|---|---|
| ***A01H 1/04*** | (2006.01) |
| ***C12N 15/82*** | (2006.01) |
| ***C12Q 1/6895*** | (2018.01) |
| ***C07K 14/415*** | (2006.01) |
| ***A01H 5/10*** | (2018.01) |

(52) U.S. Cl.

CPC .......... *C12N 15/8273* (2013.01); *A01H 1/04* (2013.01); *A01H 5/10* (2013.01); *C07K 14/415* (2013.01); *C12Q 1/6895* (2013.01); *C12Q 2600/13* (2013.01); *C12Q 2600/156* (2013.01)

(58) Field of Classification Search

None

See application file for complete search history.

(56) References Cited

U.S. PATENT DOCUMENTS

| | | | |
|---|---|---|---|
| 5,210,015 | A | 5/1993 | Gelfand et al. |
| 5,217,863 | A | 6/1993 | Cotton et al. |
| 5,468,613 | A | 11/1995 | Erlich et al. |
| 5,563,055 | A | 10/1996 | Townsend et al. |
| 5,595,890 | A | 1/1997 | Newton et al. |
| 5,616,464 | A | 4/1997 | Albagli et al. |
| 5,762,876 | A | 6/1998 | Lincoln et al. |
| 5,800,944 | A | 9/1998 | Blonsky et al. |
| 5,876,930 | A | 3/1999 | Livak et al. |
| 5,945,283 | A | 8/1999 | Kwok et al. |
| 6,004,744 | A | 12/1999 | Goelet et al. |
| 6,013,431 | A | 1/2000 | Soderlund et al. |
| 6,030,787 | A | 2/2000 | Livak et al. |
| 6,090,558 | A | 7/2000 | Butler et al. |
| 6,503,710 | B2 | 1/2003 | Gut et al. |
| 6,613,509 | B1 | 9/2003 | Chen |
| 6,799,122 | B2 | 9/2004 | Benson |
| 6,913,879 | B1 | 7/2005 | Schena |
| 6,996,476 | B2 | 2/2006 | Najarian |
| 7,238,476 | B2 | 7/2007 | McKeown et al. |
| 7,250,252 | B2 | 7/2007 | Katz et al. |
| 7,270,981 | B2 | 9/2007 | Armes et al. |
| 7,282,355 | B2 | 10/2007 | Shi |
| 7,297,485 | B2 | 11/2007 | Bornarth et al. |
| 7,312,039 | B2 | 12/2007 | Barany et al. |
| 2014/0255922 | A1 | 9/2014 | Wu et al. |

OTHER PUBLICATIONS

Lipka et al 2015 Current Opinion in Plant Biology 24:110-118 (Year: 2015).*

Arends et al., "R/qtl: High Throughput Multiple QTL Mapping," *Bioinformatics*, 26:2990-2992 (2010).

Arns et al., "Marker-Assisted Selection," *Plant Breeding*, Hayward, Bosemark, Romagosa (eds.) Chapman & Hall, London, pp. 314-331 (1993).

Aulchenko et al., "GenABEL: An R Library for Genome-Wide Association Analysis," *Bioinformatics*, 23:1294-1296 (2007).

Blenda et al., "A High Density Consensus Genetic Map of Tetraploid Cotton That Integrates Multiple Component Maps through Molecular Marker Redundancy Check," *PLoS One*, 7(9):e45739 (2012).

Borevitz et al., "Large-Scale Identification of Single-Feature Polymorphisms in Complex Genomes," *Genome Research*, 13:513-523 (2003).

Borrell et al., "Does Maintaining Green Leaf Area in Sorghum Improve Yield under Drought? II. Dry Matter Production and Yield," *Crop Science*, 40:1037-1048 (2000).

Broman et al., "R/qtl: QTL Mapping in Experimental Crosses," *Bioinformatics*, 19:889-90 (2003).

Brubaker et al., "Comparative Genetic Mapping of Allotetraploid Cotton and its Diploid Progenitors," *Genome*, 42:184-203 (1999).

Bruce et al., "Molecular and Physiological Approaches to Maize Improvement for Drought Tolerance," *Journal of Experimental Botany*, 53:13-25 (2002).

Cui et al., "Detecting Single-Feature Polymorphisms Using Oligonucleotide Array and Robustified Projection Pursuit," *Bioinformatics*, 21:3852-3858 (2005).

(Continued)

*Primary Examiner* — Brent T Page

(74) *Attorney, Agent, or Firm* — Arnold & Porter Kaye Scholer LLP; Matthew Madsen; David R. Marsh

(57) ABSTRACT

The present disclosure is in the field of plant breeding. The disclosure provides methods for breeding cotton plants having a staygreen trait using marker-assisted selection. The disclosure further provides germplasm that stays green under high drought stress and provide yield advantage over non-staygreen germplasm. The disclosure also provides genetic markers associated with staygreen QTLs for introgressing these QTLs into elite germplasm in a breeding program and producing novel cotton germplasm that performs better under water-limited conditions.

18 Claims, 2 Drawing Sheets

Specification includes a Sequence Listing.

(56) References Cited

OTHER PUBLICATIONS

Duncan et al., "Descriptive Comparison of Senescent and Non-Senescent Sorghum Genotypes," *Agronomy Journal*, 73:849-853 (1981).

Evans et al., "Wheat," In *Crop physiology: Some case histories*, L.T. Evans (ed.), Cambridge University Press, Cambridge, UK, pp. 101-150 (1975).

Flint-Garcia et al., "Structure of Linkage Disequilibrium in Plants," *Annual Review of Plant Biology*, 54:357-374 (2003).

Gruber, et al., "Vectors for Plant Transformation," in *Methods in Plant Molecular Biology and Biotechnology*, B.R. Glick and J.E. Thompson (eds.) CRC Press, Inc., Boca Raton, pp. 89-119 (1993).

Hedrick, "Gametic Disequilibrium Measures: Proceed with Caution," *Genetics*, 117:331-41 (1987).

Helsel et al., "Grain Yield Variations in Oats Associated with Differences in Leaf Area Duration Among Oat Lines," *Crop Science*, 18:765-769 (1978).

Henzell et al., "Relationships Between Yield and Non-Senescence (Staygreen) in Some Grain Sorghum Hybrids Grown Under Terminal Drought Stress," In (*Proceedings of the Second Australian Sorghum Conference, Gatton*) M.A. Foale, R.G. Henzell and P.N. Vance (eds.) Feb. 4-6, 1992) Australian Institute of Agricultural Science, Melbourne, Occasional Publication No. 68), pp. 355-358 (1992).

Horsch et al., "A Simple and General Method for Transferring Genes into Plants," *Science*, 227:1229-1231 (1985).

Jannink et al., "Association in Mapping in Plant Populations," In *Quantitative Genetics, Genomics and Plant Breeding*, Kang (ed.) CAB International, pp. 59-68 (2002).

Jansen, "Biometrics in Plant Breeding: Applications of Molecular Markers," In *Proceedings of the Ninth Meeting of the Eucarpia Section Biometrics in Plant Breeding, The Netherlands*, van Oijen and Jansen (eds.) pp. 116-124 (1994).

Jansen et al., "High Resolution of Quantitative Traits Into Multiple Loci via Interval Mapping," *Genetics*, 136:1447-1455 (1994).

Jansen et al., "Genotype-by-Environment Interaction in Genetic Mapping of Multiple Quantitative Trait Loci," *Theoretical and Applied Genetics*, 91:33-37 (1995).

Kosambi, "The Estimation of Map Distances from Recombination Values," *Annals of Eugenics*, 12:172-75 (1944).

Kruglyak et al., "A Nonparametric Approach for Mapping Quantitative Trait Loci," *Genetics*, 139:1421-1428 (1995).

Lander et al., "Mapping Mendelian Factors Underlying Quantitative Traits Using RFLP Linkage Maps," *Genetics*, 121:185-199 (1989).

Li et al., "Genome Sequence of the Cultivated Cotton *Gossypium Arboreum*," *Nature Genetics*, 46:567-572 (2014).

Li et al., "Genome Sequence of Cultivated Upland Cotton (*Gossypium hirsutum* TM-1) Provides Insights into Genome Evolution," *Nature Biotechnology*, 33:524-530 (2015).

Mild et al., "Procedures for Introducing Foreign DNA into Plants," in *Methods in Plant Molecular Biology and Biotechnology*, B.R. Glick and J.E. Thompson (eds.) CRC Press, Inc., Boca Raton pp. 67-88 (1993).

Motyer et al., "LASSO Model Selection with Post-Processing for a Genome-Wide Association Study Data Set," *BMC Proceedings*, 5(Suppl 9):S24 (2011).

Openshaw et al., "Marker-assisted Selection in Backcross Breeding," in *Proceedings of the Symposium "Analysis of Molecular Marker Data*," American Society for Horticultural Science Crop Science Society of America, pp. 41-43 (1994).

Patterson et al., "Population Structure and Eigenanalysis," *PLoS Genetics* 2:e190 (2006).

Price et al., "Principal Components Analysis Corrects for Stratification in Genome-Wide Association Studies," *Nature Genetics*, 38:904-909 (2006).

Ragot et al., "Marker-Assisted Backcrossing: a Practical Example," *Techniques Et Utilisations Des Marqueurs Moleculaires Les Colloques*, 72:45-56 (1995).

Reich et al., "Linkage Disequilibrium in the Human Genome," *Nature*, 411:199-204 (2001).

Rosenow et al., "Drought Tolerant Sorghum and Cotton Germplasm," *Agricultural Water Management*, 7:207-222 (1983).

Russell, "Genetic Improvement of Maize Yields," *Advances in Agronomy*, 46:245-298 (1991).

Service, "Gene Sequencing: The Race for the $1000 Genome," *Science* 311:1544-46 (2006).

Subudhi et al., "Quantitative Trait Loci for the Stay-Green Trait in Sorghum (*Sorghum bicolor* L. Moench): Consistency Across Genetic Backgrounds and Environments," *Theoretical Applied Genetics*, 101:733-741 (2000).

Thomas et al., "Five Ways to Stay Green," *Journal of Experimental Botany*, 51:329-337 (2000).

Thomas et al., "Crops That Stay Green," *Annals of Applied Biology*, 123:193-219 (1993).

Tollenaar et al., "Leaf Senescence in Short-Season Maize Hybrids," *Canadian Journal of Plant Science*, 58:869-874 (1978).

Utz et al., "Comparison of Different Approaches to Interval Mapping of Quantitative Trait Loci," In *Biometrics in Plant Breeding*, van Oijen, Jansen (eds.) *Proceedings of the Ninth Meeting of the Eucarpia Section Biometrics in Plant Breeding, The Netherlands*, pp. 195-204 (1994).

Waldmann et al., "Evaluation of the Lasso and the Elastic Net in Genome-Wide Association Studies," *Front Genetics*, 4:1-11 (2013).

Wang et al., "The Draft Genome of a Diploid Cotton *Gossypium raimondii*," *Nature Genetics*, 44:1098-1103 (2012).

Wang et al., "A Whole-Genome DNA Marker Map for Cotton Based on the D-Genome Sequence of *Gossypium raimondii* L," *G3 (Bethesda)*, 3:1759-67 (2013).

Wolfe et al., "Interactive Water and Nitrogen Effects on Senescence of Maize. I. Leaf Area Duration, Nitrogen Distribution, and Yield," *Agronomy Journal*, 80:859-864 (1988).

Yan et al., "Overexpression of the *Arabidopsis* 14-3-3 Protein GF14λ, in Cotton Leads to a 'Stay-Green' Phenotype and Improves Stress Tolerance under Moderate Drought Conditions," *Plant and Cell Physiology*, 45:1007-1014 (2004).

Yu et al., "A Unified Mixed-Model Method for Association Mapping that Accounts for Multiple Levels of Relatedness," *Nature Genetics*, 38:203-208 (2006).

Yu et al., "Genome Structure of Cotton Revealed by a Genome-Wide SSR Genetic Map Constructed from a $BC_1$ Population Between *Gossypium hirsutum* and *G. barbadense*," *BMC Genomics*, 12:15 (2011).

Zeng, "Precision Mapping of Quantitative Trait Loci," *Genetics*, 136:1457-1468 (1994).

Zhang et al., "Sequencing of Allotetraploid Cotton (*Gossypium hirsutum* L. acc. TM-1) Provides a Resource for Fiber Improvement," *Nature Biotechnology*, 33:531-537 (2015).

* cited by examiner

```
                              SEQUENCE LISTING


<160> NUMBER OF SEQ ID NOS: 44

<210> SEQ ID NO 1
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t

<400> SEQUENCE: 1

gccccgccaa agttaatagt gggcacgata gttgttttat gtatatagag gggtttcctt      60

ngaggccacg ccttagggtt taagtcttta tgtcaataac tggattttat tttgaaactt     120

t                                                                     121


<210> SEQ ID NO 2
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t

<400> SEQUENCE: 2

tattacagtg cagcaaaggc agcaaaaaaa aagaaacaaa aataattaaa caataatcat      60

ntggaaaatg actgagactt gtaaagattg acgtaaagaa gttaccatca aacgtcggcc     120

a                                                                     121


<210> SEQ ID NO 3
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t

<400> SEQUENCE: 3

ttttattttt aacaatacaa agtcaaataa tacgtgatga taccaattaa aataaatata      60

naagtaatat tcttattaaa aataaaaaat aaaaaacgaa aaataaataa atgagtggta     120

a                                                                     121


<210> SEQ ID NO 4
<211> LENGTH: 594
<212> TYPE: DNA
<213> ORGANISM: Glycine max
<220> FEATURE:
<221> NAME/KEY: misc_feature
<222> LOCATION: (440)..(440)
<223> OTHER INFORMATION: n is a, c, g, or t

<400> SEQUENCE: 4

gataagatca aggcatacca tgatcaaaag atagcccgta aacaatttgt ggtaaggcaa      60

aaagtattac tttatgactt tatactaaga atctttgtag gtaagttttg acctaagtag     120

ttagggtctt ttgttattat ttacgtattt ccacatggta cagttgaggt taaaagcgaa     180
```

```
gaatccggaa aaaatttcaa ggtcaacgga cagcgattaa agcctttcta caaaaatttt    240

caagtccaca tggttgaaga attagtcctc gaggagccga ttaaataaat ttcaaggtca    300

tcgagttaac gacgttaaac aaaagcgctt tttgggagac aacccaaatt tattctcatt    360

tatttaattt tgagtttaag taagatttag gttgtaaata aatttttatt tattccagtt    420

aatttaatat tttgaggaan gtaatggagg ttgtgaatat ttcaaaagtc gaataatgat    480

ggtggcgtgg ccacaacatg ctacatgctg aaaattattt acctacaaac aaaatccaac    540

accgacaaca ccgttaaaag acacatggtg agtattctta actttttaa ttgt           594
```

```
<210> SEQ ID NO 5
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t

<400> SEQUENCE: 5

ccgcctcaaa attagtaatg ggcataattc ctatttagtc ctttttattt tctttaatct     60

ntaattaagc tttcacacct attttaattt agtccctttt cctaattatt cttaattcta    120

g                                                                     121
```

```
<210> SEQ ID NO 6
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t

<400> SEQUENCE: 6

aaagctaagc tagtgaggca aagaagtatc aagtgagttt ttgtactcca tccctaaaat     60

nttgtgtgac tgtcatgttt tgtaaggata taggaactct gttgattgtg aatgctaagc    120

a                                                                     121
```

```
<210> SEQ ID NO 7
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t

<400> SEQUENCE: 7

atagtatgat gacaaatttg cactttaact cattaaatta ttaagttaga tgaaatgaat     60

ntgaagttta atttagacct tgtttgatag accattgaaa aaaaaatcta ttgaaaatta    120

a                                                                     121
```

```
<210> SEQ ID NO 8
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t
```

<400> SEQUENCE: 8

```
tcaaattatt agctaatttt ataatgctcc aaactatgaa aaatattttt attgataaaa    60

ntgatttaga gtgttttcgg gacatagata ttgataacat tttaaacttt ttaactgaag   120

a                                                                   121
```

<210> SEQ ID NO 9
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t

<400> SEQUENCE: 9

```
tttttaagtt ccgagttcac ctctgttgct tctacatcaa aattgagtca ggtgtgtaac    60

naaaactcta aaaaatacaa taggtaaaaa ccaaaagtca tgactatcgg cactacacga   120

c                                                                   121
```

<210> SEQ ID NO 10
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t

<400> SEQUENCE: 10

```
ttgaacaacc taccttggaa ctttcgtcag ccatggaggg tattgttaaa aaccttcatc    60

nggataggga atggtttaat ntggagagtt catccttgaa ggagggaaaa agtttggaag   120

t                                                                   121
```

<210> SEQ ID NO 11
<211> LENGTH: 601
<212> TYPE: DNA
<213> ORGANISM: Glycine max
<220> FEATURE:
<221> NAME/KEY: misc_feature
<222> LOCATION: (224)..(224)
<223> OTHER INFORMATION: n is a, c, g, or t

<400> SEQUENCE: 11

```
cggcccagat tatgtgaata gttagctcaa gaactccttt ttttgcagca gataaacatc    60

agtttgtctg ttgttttaat aactaattac tgtaattttt ccccctatga attaagcaca   120

acaagtttcc cctttttttg attgacgtat atttatgggt ttgatagtaa ttatttctgc   180

cggaatctga aaactaattc ctgctatttc ttgctctatg atgnataact ttacgtgttt   240

tgctgatcta tctttaatta gtgttatgag cgcattactt tttgttttgt tctgttggtt   300

gcagaattga tataatatca aacttcctta atttgtacta atttgaaaat ttacttatga   360

ttcaagtttc gggaaatgga tgctggtaat tgcttttttta gaaccatttg aaatgcatag   420

atgaaccaat tttctcccaa caccagattt gtcaaaatat cgaaaaccat gggcaaataa   480

aatagtaata acagttttga tattattttt tcttcatgcc attggttaag gatggacatt   540

ataaaaaaga ttcgctataa ttcctttctg agattttccg tttagcaatc aggatgggag   600
```

```
c                                                                   601


<210> SEQ ID NO 12
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t

<400> SEQUENCE: 12

caataacgaa aagtttcttg taatgatatt tgaaattaat atggcacaaa atggtaatgc     60

ntgatggatt gatattggag caaccaacca tgtatgtaaa gacaaaagca tgttcacaaa    120

g                                                                   121


<210> SEQ ID NO 13
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t

<400> SEQUENCE: 13

agactagcat ctcttttttt ttgttctatt taaaagtttc aattaaagct ttccttaatc     60

nttttttttgg tttctttatt gggttgtaaa ttattaatta tttattcctt ttagaacagt    120

g                                                                   121


<210> SEQ ID NO 14
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t

<400> SEQUENCE: 14

ttcagttttt taattggttt gaagattaca aaagacggaa attttgtaaa ttaagtaaat     60

nttaaataat caaaaataag atttttaata aattaataat taatagtaaa taataataag    120

g                                                                   121


<210> SEQ ID NO 15
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t

<400> SEQUENCE: 15

gtgatggtca gtttaaaaat aaaaatagca tattttatga ttaagtaagt tacgtgttag     60

naagtaattt ctaagccaaa attcttttta aaangggaga attgtaacac cccaaaatag    120

g                                                                   121
```

```
<210> SEQ ID NO 16
<211> LENGTH: 676
<212> TYPE: DNA
<213> ORGANISM: Glycine max
<220> FEATURE:
<221> NAME/KEY: misc_feature
<222> LOCATION: (292)..(292)
<223> OTHER INFORMATION: n is a, c, g, or t

<400> SEQUENCE: 16

cggaggtaga gttgtcaatc tttgtaataa aaaagttctg gattcatctt caatagggta      60

attggccact acttgtctgt atttaaaagc ccgcaatgtt gaatatatta ttgttctttg     120

agccctgtta tttacttttc cctcttcgaa aacttttaaa atctcctttt tcccggttaa     180

caaacatcat tttctgtgaa aaagaaattc atctaaaaga ctaaaggact agaggaaaag     240

gaaaaagaag atggaactag tggtggaaac aataactgga taccacggct tncagcggtt     300

caacctaatc aagcttatat ttgttgccgg tgccagttat atcggctgtt tgactcaatc     360

aaccactcat ttggtttgtt tccttttctc ttagtactta aaaaaaaaca attaaaggga     420

aaatggggaa aactaaattt atttggaatt taggtatgtt ggagatttga aggaaggaaa     480

tatgagcttg ctaagaagtt aaagacgatt gtataaagga aggaaagcat ttgcctgagg     540

gtctttatat gttgcgaagg tattaatttc tattaatttc ttatctttct attaattttt     600

ggtttaattt cttttaagtt atttctcatt gtgttgtttt tggtgctcat agatgggaga     660

cccttctgta gaggtt                                                     676


<210> SEQ ID NO 17
<211> LENGTH: 508
<212> TYPE: DNA
<213> ORGANISM: Glycine max
<220> FEATURE:
<221> NAME/KEY: misc_feature
<222> LOCATION: (104)..(104)
<223> OTHER INFORMATION: n is a, c, g, or t

<400> SEQUENCE: 17

ttagtgtgaa gtacggttgg tttccgatca ctggcgaggc ggcagcggtg gaaagagtct      60

ctaggaaagc gattaggcct tgccctcctc ctatgaacgg gaanaataat tgtgcttctg     120

gtgatatcgt agaggtgttc gatgacttat cctggaaacc ggcggtgatt gttaaggttc     180

ttggtggaaa caacttttcc gttaggattc ttgggtcgag tagcgaactc aaagcgcatc     240

aatctcgatt gcgtattcgg cagtcttggg aagatggcaa ttggttcctc gttggaaagg     300

taaatccttt cgattctttt tctaaacgat aattttaata tttctcttca tttttttttgt     360

tatacgttaa ctgattctta ccttaattat tattttctac ttcagggttc atcaaattcc     420

actgggccgc agaaaaggaa aagatcttcg cttggcttct catatattgg tgcgcaaaag     480

aagagggtgt tggaggaagg taggaatg                                        508


<210> SEQ ID NO 18
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t

<400> SEQUENCE: 18

tcgaacttaa agaaaaccgg gtgtgacaat ggttttggga tgtcttgata tcgtgatacc      60
```

```
nattacttgg tatcgtgata ccactatatc tggtcttgat tcttttcatt tcagcactgt    120

t                                                                     121


<210> SEQ ID NO 19
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t

<400> SEQUENCE: 19

gcgtttttaa acatctaata tgtgagctta aaaagctcaa taagtatcaa tggataaacc     60

nacttatctt atgctttatt agtgttgagc ccttcttaaa catgtctttg tcaattcatt    120

c                                                                     121


<210> SEQ ID NO 20
<211> LENGTH: 170
<212> TYPE: DNA
<213> ORGANISM: Glycine max
<220> FEATURE:
<221> NAME/KEY: misc_feature
<222> LOCATION: (50)..(50)
<223> OTHER INFORMATION: n is a, c, g, or t

<400> SEQUENCE: 20

ttagacattg gcgatctgct tcatttcttg cttcgtcgct ttggttatcn gatgcgagtt     60

tcatctctct cagtctctct tagtgtcttt ctttttgtct tcatcttttc tttggaaaaa    120

agttgcgtaa ttttgttgtg aatgttcaat tgttgtttcg cttttttttt               170


<210> SEQ ID NO 21
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t

<400> SEQUENCE: 21

acacagaatg cacttacgag actcattcac ttatttaaca aattcgtagc ttctcatacc     60

ngatttcata tgcatactta ctacagatct tcatattcat gcattaacat atatacttca    120

t                                                                     121


<210> SEQ ID NO 22
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t

<400> SEQUENCE: 22

aatataaaaa cgaacttaaa attttacatt gtacaaaccc aaatttgact aagcccaata     60

naccaactac ctacccaaaa ccaaaaccca ttaacccaaa cctaatttca accctagccc    120

a                                                                     121


<210> SEQ ID NO 23
```

```
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t

<400> SEQUENCE: 23

atgattccaa tgcaatggga cagaaacatt ttgtataact ttatatcgat gtatacaatt     60

naatcaaaat taaagttacc gtcttttttt gtgttagcct tcgttgaaac atagatttca    120

g                                                                    121


<210> SEQ ID NO 24
<211> LENGTH: 611
<212> TYPE: DNA
<213> ORGANISM: Glycine max
<220> FEATURE:
<221> NAME/KEY: misc_feature
<222> LOCATION: (38)..(40)
<223> OTHER INFORMATION: n is a, c, g, or t
<220> FEATURE:
<221> NAME/KEY: misc_feature
<222> LOCATION: (230)..(230)
<223> OTHER INFORMATION: n is a, c, g, or t

<400> SEQUENCE: 24

tcgtcaatca taataataat catctccaag acgaccannn tttctaaatc actgccgtct     60

ctatcctcca gatctgagtt caataaaaag gcttctttaa tcgggtcggg tatccatgaa    120

acctctcaaa agattggtcg acttgctaaa tgtaagccat ttcttttaat tgttttctta    180

gcttaatttt tttaaaaagt tttgcttgtt attcgatcca attcaaaaan atagtaatcc    240

agattttagc tcttaagaat aaaaaaaagt tgattaattt atgtgctata ggtataaatc    300

ctaaggatca gattagtagc tagttttcaa ttgggatttt gaaatgttgt gaattttttt    360

attgttttta atgtaattgt tgcagtggcg aaaaggtcat caatgttcga tgatccggtt    420

gttgaaatac aagaactgac tgcgttgata aaaactgata ttaccacctt gaatatggca    480

ctttctgatt tacaaacact tcaaaacatg gagattgccg atgggaatta ctccgaggat    540

cgaattgttc attcgaccac tgtttgtgat gacttgaaga acaagttaat gggtgctaca    600

aagcattttc a                                                         611


<210> SEQ ID NO 25
<211> LENGTH: 645
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t

<400> SEQUENCE: 25

cttctgtcta acaaaatcac tttcagtctc tttcccattt aataaaacca ctttctcttt     60

natgtacact tatatttgac actttttgct tgttaattct tttgtcttat gaatttttca    120

ctgcttaatt ggttgtattt gatttatttc ttgtgtagtg aacccaatac tggaaatgac    180

aacaaaaaga cgtaatctgc agttttcttt ctttttattc tgtcacggct ggagtcgtgg    240

gcacgacgct gggcacgatg cggggcacga tgcggatctg acgtggcaaa tcagaagtca    300

acacagggaa tattctggaa acaacttatc ttgatctatt gacgtgattt gggagatttt    360

ggatttcatt ttcataattt taaagatatt atcttatctt tttttgatta gtttgttgat    420
```

```
ttgggaattt gaagcctata aatacccacc tttgggtaag gctaagggga tctcgtcttt    480

tgttcttatt gctactttat tttcattttt aataaaattt tcttctttta tttatttcta    540

ctttatttta ttttatttta tgtttttaca ttatcaaaac atgttaagca tgataatcaa    600

tatcatgctt ggctaatttt tctcaagcca agagctagta cgatt                    645


<210> SEQ ID NO 26
<211> LENGTH: 121
<212> TYPE: DNA
<213> ORGANISM: Glycine max
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t

<400> SEQUENCE: 26

tgatgatctn gtatatactt tcatactttc ctcatccaat ttttttttta aatggagatt     60

nataatttat ttatttatga atcatattat agcatcttat taaaagtttt taaaaataaa    120

c                                                                    121


<210> SEQ ID NO 27
<211> LENGTH: 250
<212> TYPE: DNA
<213> ORGANISM: Glycine max
<220> FEATURE:
<221> NAME/KEY: misc_feature
<222> LOCATION: (150)..(150)
<223> OTHER INFORMATION: n is a, c, g, or t

<400> SEQUENCE: 27

cgttgctgct ttgtttatag agaaagcaga aaaatgaatc tttcaactcc gcgtgcttac     60

ttttttaaag aaagttgcat ttgaataatt ttaaatttat tttttcaaaa aaattaattt    120

aataatataa taaaataaaa atttatcagn tcaaaaatat ttttaataga gctgcaatgt    180

ttggttgatg ggaatcgagg aacaaacaag aatgtgtatc tgtcccataa ttaacttaat    240

cccaaaattc                                                           250


<210> SEQ ID NO 28
<211> LENGTH: 683
<212> TYPE: DNA
<213> ORGANISM: Glycine max
<220> FEATURE:
<221> NAME/KEY: misc_feature
<222> LOCATION: (391)..(391)
<223> OTHER INFORMATION: n is a, c, g, or t

<400> SEQUENCE: 28

gcagtctttg ctgaagttgg taaattaaaa gggtggcata taggaggagg caaatttgac     60

aggtaactat atttttctca ccttcttata tttgagttat ctttgttttg gatttcatat    120

atgtatgtat atttatttat ttattgtatg ctagacctga aacagagtac attgaggata    180

ttgttaaata tgttataaaa aagttgatga gtaccaaatc tggacatgtt tatgaagaac    240

tggttggaat agattatcag aaagatgcaa ttttgaggct gattgagcaa gaacgctatc    300

gtgtaatagg actctgggga atgggtggta taggcaaaac taccettgct gatgttgtac    360

ataaggaaat gtctccaaag tttaaaagcc nttgctttct tcaaaatgtt agtgagaaaa    420
```

```
taaaaaacca aggaaaggaa tctttacgaa atgatcttct ttccatactg ttaaatgaaa    480

aagatattca tatagacact cctttgatag gataccctta ccgagagagg ttgaacaata    540

aaaaagtact tcttgtgctt gatgatgtta gtcaccaaga ccaaataact attatgggtg    600

ttagacattt tggtgatgga agtaaaatca ttgtaacatc tagagataga aaagtacttg    660

agaatggaga agctgaccaa att                                            683


<210> SEQ ID NO 29
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t

<400> SEQUENCE: 29

ttaattttca catgttatca tattggattt gtttaacaat atctcaattt acatcacttg     60

ntatataaat aaattttcac atatcaatcc acatttcatt tatacaatga cattattcat    120

t                                                                    121


<210> SEQ ID NO 30
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t

<400> SEQUENCE: 30

gatagaccga gctgagtagg atactaaatg tatacctgac tgtactgatg tatgtatatc     60

ngttttttgt atgaagcatg ttgagcatgt ttaatttgtt atatctgtat ctcaatttct    120

g                                                                    121


<210> SEQ ID NO 31
<211> LENGTH: 121
<212> TYPE: DNA
<213> ORGANISM: Glycine max
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t

<400> SEQUENCE: 31

aaataccagn aagatggtgg agaagatttt aacaaatctt gaaaaaaaaa taaaaataaa     60

natatggtaa aattaggtgt aggcgacgac aacaacagag gaagaaagaa aaaattgaag    120

a                                                                    121


<210> SEQ ID NO 32
<211> LENGTH: 400
<212> TYPE: DNA
<213> ORGANISM: Glycine max
<220> FEATURE:
<221> NAME/KEY: misc_feature
<222> LOCATION: (230)..(230)
<223> OTHER INFORMATION: n is a, c, g, or t

<400> SEQUENCE: 32
```

```
atttagaatt aaatgaatag aaataggtta cattgaatgt ggtttctcac aaagtatgga     60

aatggtttga gaatcaattt aagtttttca aattattatt taactaataa tgaaagtttg    120

aaaatgaaat gaaattaatt ggtcattgtg aatccgttga gtgtagaaat tgaatatatt    180

tgctcataga ttctgttatg gtaaatttgt catgacttta acgaaattan aattgggttg    240

aaaagattat tgaatttgaa aattaattaa tttatataaa ttaatttaat aatatttatt    300

ttgggaaata aaaaaacatg cattgggtta gattaaatta taacgtgttg ggttaaaagt    360

ccaaaaagca cgtataattc aacctgatac agacccctca                          400


<210> SEQ ID NO 33
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (97)..(97)
<223> OTHER INFORMATION: n is a, c, g, or t

<400> SEQUENCE: 33

cgtggtatca tgtattgtca gtaatcggta taggtcgtag ctgtatccct gtgggctcac     60

ncctgctaac tttgtcttgt atttagacat tgtacgngta gaaagataca tgtatgtggt    120

t                                                                    121


<210> SEQ ID NO 34
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t

<400> SEQUENCE: 34

gttaataata gtcatatcta atgaaactaa aataaaaaaa taactactca aggatgtaaa     60

naaaattgca taatttagag aggggcaaaa atataaataa ttataaaata aaaatgttag    120

a                                                                    121


<210> SEQ ID NO 35
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t

<400> SEQUENCE: 35

tctgtaaatt ataaattttc acgcactcat ttacgtaaat tcaatttatt aaaaattacc     60

ntgtttcatc ttaaattaat tattattttt ttaaatcaag tagatattta aatattaaaa    120

t                                                                    121


<210> SEQ ID NO 36
<211> LENGTH: 575
<212> TYPE: DNA
<213> ORGANISM: Glycine max
<220> FEATURE:
```

```
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (437)..(438)
<223> OTHER INFORMATION: n is a, c, g, or t
<220> FEATURE:
<221> NAME/KEY: misc_feature
<222> LOCATION: (524)..(526)
<223> OTHER INFORMATION: n is a, c, g, or t
<220> FEATURE:
<221> NAME/KEY: misc_feature
<222> LOCATION: (557)..(557)
<223> OTHER INFORMATION: n is a, c, g, or t

<400> SEQUENCE: 36

tcttcccttt ctctccatta accctcaact ccgtctccaa accccccaaa tttatccctt     60

tagcttccat ttctcctccc ccggcaacac cctgcaaatc tcccgaaatc ccagctctgt    120

ccccactcga cggttcaact cgaaccctca aaaccntttt ctccttggcc ctctctgcca    180

ccatcgtctt caccaaaatg atccaaaatt atgctctcaa aacaatctcc cagaacccca    240

acgcactttc caccgtgggc cctctcttct tcgcttcctt aaaggaccgc cctagcggat    300

acctcaacac gcctttgact gtggttgcag cgggattagc taagtggctt gacatttaca    360

gtggggtttt gatggttagg gttttactca gttggttccc taacattccc tgggaccggc    420

agcccctttc ggctatnngg gatctatgtg atccttattt gaatctcttt aggaatataa    480

ttccgccgat gttcgacacc ttggatgtta gcccgcttct agcnnncgcc gtgttgggga    540

ctctcggctc gatgctnaat aacagtagag gaatg                               575


<210> SEQ ID NO 37
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t

<400> SEQUENCE: 37

ataaatatga tgataagatt aaatattgta acaatactgt agcacgagac aaaaaaaataa     60

nttaaactcg ccatatttca ccgtccattc aagctcactc aaagtctatc cattggactt    120

t                                                                    121


<210> SEQ ID NO 38
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t

<400> SEQUENCE: 38

aacaaagttc acatgtaatg taataccgtc gaagatatta gattgaaatt aaaaaaaaaa     60

nagaaaaaaa cctgactgaa aaggaaaatt gaatgggctt caaccaaaac cagcccaatt    120

t                                                                    121


<210> SEQ ID NO 39
<211> LENGTH: 121
<212> TYPE: DNA
<213> ORGANISM: Glycine max
```

<220> FEATURE:
<221> NAME/KEY: misc_feature
<222> LOCATION: (61)..(61)
<223> OTHER INFORMATION: n is a, c, g, or t

<400> SEQUENCE: 39
taataatgga aacaacaact ttaatcacca tccctatatc tagtttattt gtaagtttta 60
ntgggtacat cttatatact attttttaga taactttctc aataattaag aaattcattt 120
g 121

<210> SEQ ID NO 40
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t

<400> SEQUENCE: 40
cttgtttgag ggaggtttcg atttccaagc cataggcatc aatactaaac cttaaaattg 60
nttggaaaat actttagaaa cattttgaag ggccttggaa ttactaaata tgctcataat 120
a 121

<210> SEQ ID NO 41
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t

<400> SEQUENCE: 41
cttaattatc aaattgagaa aacaaaaact atataatcca cgacctcgtt aaacataata 60
ntatgaaccc taattgaatt atacacaaag atatcacata caaattctta atacactaat 120
t 121

<210> SEQ ID NO 42
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t

<400> SEQUENCE: 42
tttatccaga caccaaattg ttgccagatt gaatgggaaa atatccaaac agatctcact 60
natgcctact tgcatgcctt agtgctacta gatattttat catagctcat acacaaatta 120
t 121

<210> SEQ ID NO 43
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (115)..(115)

-continued

```
<223> OTHER INFORMATION: n is a, c, g, or t

<400> SEQUENCE: 43

acaagaggtg acgggtgatg gggttcaaaa agccgtgaac atgaattact ttgtcggggg      60

naaaacatac tcatttgaca atggagaacc gctgatactt ttttgggggg ggggnaagaa     120

a                                                                     121


<210> SEQ ID NO 44
<211> LENGTH: 121
<212> TYPE: DNA
<213> ORGANISM: Glycine max
<220> FEATURE:
<221> NAME/KEY: misc_feature
<222> LOCATION: (61)..(61)
<223> OTHER INFORMATION: n is a, c, g, or t

<400> SEQUENCE: 44

attaattttt tattaaaaaa atttaaaccg gttcaacata ttcaactatt gtttttttact      60

nagatttcaa tttttactgg tttcgagctg tttccggttc aatcggttca acccatttat     120

t                                                                     121
```

METHODS FOR PRODUCING COTTON PLANTS WITH ENHANCED DROUGHT TOLERANCE AND COMPOSITIONS THEREOF

CROSS-REFERENCE TO RELATED APPLICATIONS

This application claims the benefit and priority of U.S. Provisional Application No. 62/206,695, filed on Aug. 18, 2015 and U.S. Provisional Application No. 62/218,923, filed on Sep. 15, 2015, both of which are incorporated by reference in their entirety herein.

FIELD

The present disclosure relates to the field of agricultural biotechnology. More specifically, the disclosure relates to methods for producing cotton plants with improved staygreen potential and drought tolerance.

INCORPORATION OF SEQUENCE LISTING

A sequence listing contained in the file named "P34321US04_SEQ.txt" which is 23,231 bytes in size (measured in MS-Windows®) and created on Aug. 15, 2016, comprises 44 nucleotide sequences, is filed electronically herewith and incorporated by reference in its entirety.

BACKGROUND

Cotton is an important and valuable field crop primarily due to the intrinsic value of their fiber (lint) to provide soft, breathable textile products. Cotton is also an important source of vegetable oil used extensively in foodstuffs for baking and frying and in spreads such as margarine and mayonnaise. The seed bagasse is used as raw materials in livestock feed, fertilizer, paper, and biofuel. Despite the importance of cotton's secondary products, 90% of cotton's value resides in the lint fiber.

Commercial cotton breeding programs have aimed to develop new, unique, and superior cotton varieties with desirable traits such as higher fiber (lint) yield, earlier maturity, improved fiber quality, resistance to diseases and insects, tolerance to drought and heat, and other improved agronomic traits. However, breeding cotton for yield and fiber quality has been challenging. Part of the challenge comes from limited genetic diversity in breeding programs and increasing vulnerability of germplasm to environmental stress. Among all types of environmental stress, drought or water deficit is a major limiting factor for cotton production in many cotton production areas.

Studies on the response of cotton to drought stress have shown many deleterious effects of drought, depending on the time, length, and severity of the stress as well as the plant developmental stage. Drought stress in cotton can decrease leaf water potential and leaf area, and therefore promotes stunted vegetative growth including reduced shoot growth, shortened internodes, and abscised lower leaves when the stress is severe. If the drought stress is encountered during the reproductive stage, it increases square and boll abortions, leading to lower yield.

The detrimental effects of drought can be minimized by the development of drought tolerant cotton cultivars. However, there are limited reports on this aspect due to the complex nature of drought tolerant mechanisms. Cotton possesses sophisticated mechanisms to adapt and grow in soils with limited water availability. For instance, cotton develops a deep-penetrating and extensive root system (having large numbers of lateral roots) with narrower tap roots, sheds leaves and fruits, and has a flexible fruiting period when exposed to drought stress. Differences in stomatal distribution and behavior have been observed in cotton grown in soils with restricted water availability. Despite these phenotypic manifestations of drought tolerance, little is known about molecular mechanisms underlying drought resistance in cotton.

There is a need to breed new cotton varieties with improved drought tolerance. New cotton germplasm providing drought tolerance is highly sought after. To assist molecular breeding, genetic loci and markers, haplotypes, and chromosomal intervals that confer or are linked to drought tolerance are also much desired. Further, there is a need for a rapid, cost-efficient method to assay, monitor, and introgress drought tolerance traits in cotton.

SUMMARY

In one aspect, this disclosure provides a method of creating a population of cotton plants or seeds, which method comprising the steps of: (a) genotyping a first population of cotton plants or seeds at a marker locus associated with a staygreen (STG) quantitative trait locus (QTL) selected from the group consisting of STG QTLs 1 to 7; (b) selecting from the first population one or more cotton plants or seeds comprising an STG allele of the marker locus; and (c) producing from the selected one or more cotton plants or seeds a second population of cotton plants or seeds comprising the STG QTL. In a further aspect, a method comprises genotyping a first population of cotton plants or seeds at a marker locus within about 20 cM, 15 cM, 10 cM, 5 cM, 4 cM, 3 cM, 2 cM, 1 cM, 0.5 cM, or less than 0.5 cM of any one of marker loci SEQ ID NOs: 1 to 44. In an aspect, a method further comprises: phenotyping the second population of cotton plants or seeds to confirm an STG trait.

In one aspect, this disclosure provides a method of introgressing an STG QTL, the method comprising: (a) crossing a first cotton plant comprising an STG QTL selected from the group consisting of STG QTLs 1 to 7, with a second cotton plant of a different genotype to produce one or more progeny plants or seeds; and (b) assaying the one or more progeny plants or seeds at a marker locus associated with the STG QTL; and (c) selecting a progeny plant or seed comprising the STG QTL. In an aspect, a method further comprises: (d) crossing the selected progeny plant with itself or the second plant to produce one or more further progeny plants or seeds; and (e) selecting a further progeny plant or seed comprising the STG QTL. In another aspect, step (e) comprises marker-assisted selection, optionally, with a marker within about 20 cM, 15 cM, 10 cM, 5 cM, 4 cM, 3 cM, 2 cM, 1 cM, 0.5 cM, or less than 0.5 cM of any one of STG QTLs 1 to 7.

In another aspect, this disclosure provides a method for selecting a cotton plant or seed, the method comprising: (a) detecting in a population of cotton plants or seeds a cotton plant or seed comprising an STG allele of a marker locus associated with an STG QTL selected from the group consisting of STG QTLs 1 to 7; and (b) selecting the cotton plant or seed comprising the STG allele.

In a further aspect, this disclosure provides a method for evaluating a collection of cotton germplasm, the method comprising: (a) obtaining a collection of cotton germplasm; (b) isolating nucleic acids from each germplasm; (c) assaying the nucleic acids for one or more markers linked to or associated with an STG QTL selected from the group consisting of STG QTLs 1 to 7; (d) selecting germplasm having an STG QTL based on the marker assay. In another aspect, a method further comprises confirming that the selected germplasm has post-anthesis drought or heat tolerance.

In one aspect, this disclosure provides a method comprising providing a set of cotton seeds comprising one or more STG QTLs selected from the group consisting of STG QTLs 1 to 7, to a person desirous of planting the set of cotton seeds in a field plot prone to drought or heat stress.

In another aspect, this disclosure provides a method of growing a population of cotton plants, the method comprising planting a population of cotton seeds comprising one or more introgressed STG QTLs selected from the group consisting of STG QTLs 1 to 7. In another aspect, this disclosure provides a method of growing a population of cotton plants in a field plot prone to drought or heat stress, the method comprising planting a population of cotton seeds comprising one or more introgressed STG QTLs selected from the group consisting of STG QTLs 1 to 7 in the field plot prone to drought or heat stress.

In another aspect, this disclosure provides a method of reducing the cost of watering cotton plants, the method comprising: (a) growing a population of cotton plants comprising one or more introgressed STG QTLs selected from the group consisting of STG QTLs 1 to 7; and (b) reducing the amount of water supplied to the population of cotton plants after the cotton plants start flowering.

In a further aspect, this disclosure provides cotton plants or seeds comprising a staygreen trait when grown under water-limited conditions, and further comprising one or more, introgressed STG QTLs selected from the group consisting of STG QTLs 1 to 7. In an aspect, the introgressed STG QTLs are also present in or originate from one or more cotton germplasm selected from the group consisting of STG-001 and STG-002 having an ATCC deposit number of PTA-122486 and PTA-122487, respectively. In an aspect, cotton plants or seeds disclosed herein exhibit post-anthesis drought or heat tolerance. In another aspect, cotton plants or seeds disclosed herein exhibit no yield penalty under water-sufficient conditions. In a further aspect, cotton plants or seeds disclosed herein exhibit a delayed onset of senescence under water-limited conditions. In another aspect, cotton plants or seeds disclosed herein exhibit a reduced rate of senescence under water-limited conditions. In an aspect, cotton plants or seeds disclosed herein exhibit greener leaves compared to cotton plants without the STG QTL under similar water-sufficient conditions.

In a further aspect, the instant disclosure provides methods to enhance cotton plant performance under water deficit conditions by combining two or more staygreen QTLs disclosed herein. In an aspect, the combined staygreen QTLs have additive effects in providing drought tolerance. In another aspect, the combined staygreen QTLs have synergistic effects in providing drought tolerance. In a further aspect, the combination of two or more staygreen QTLs disclosed herein has no negative effects over cotton physiology, resistance, yield, or performance in general.

BRIEF DESCRIPTION OF THE SEQUENCES

Figure 1:
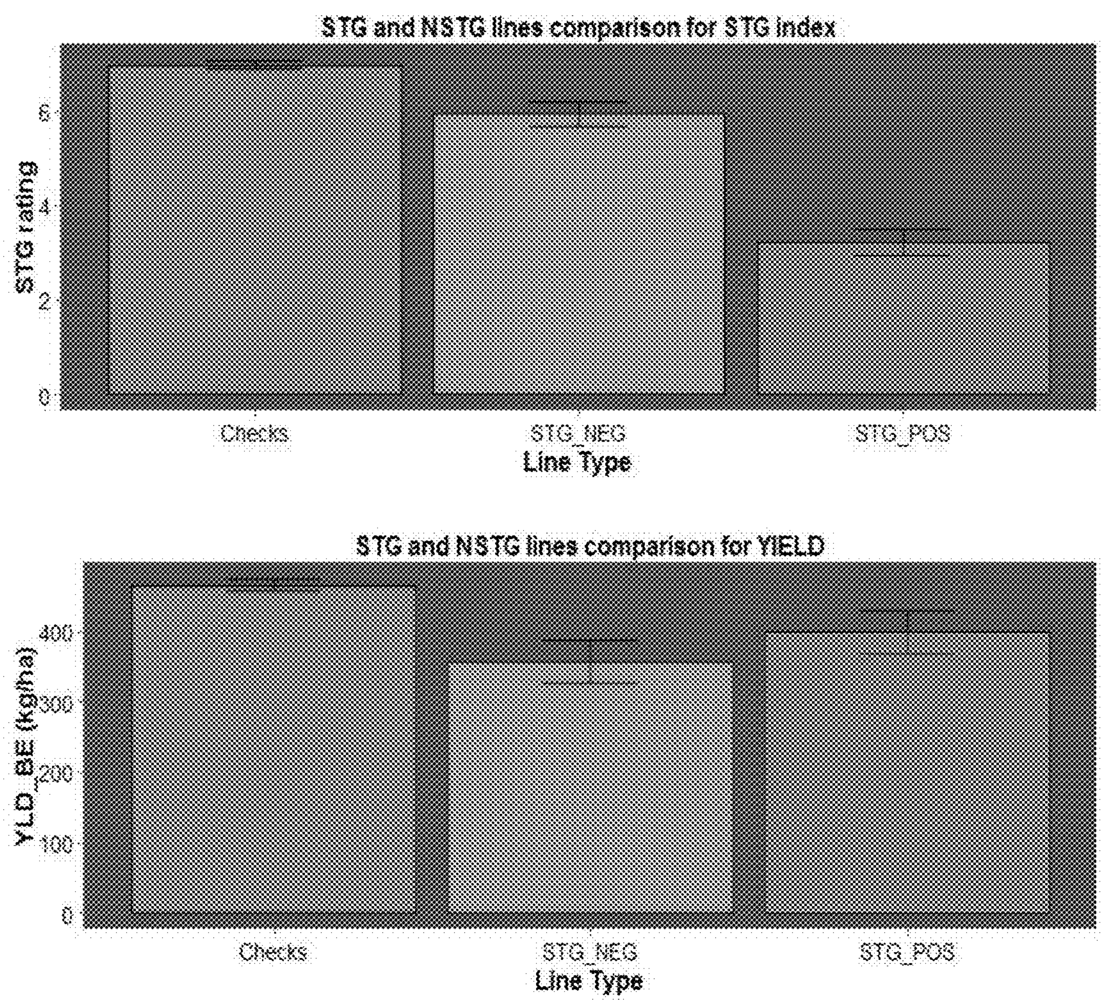
FIG. 1 shows the staygreen (STG) index and yield of staygreen and non-staygreen plants under high moisture stress. STG_POS: staygreen individuals based on genotype at QTL1 and QTL2; STG_NEG: non-staygreen individuals based on genotype at QTL1 and QTL2.

SEQ ID NOs: 1 to 7 list sequences of exemplary SNP marker loci associated with STG QTL 1. SEQ ID NOs: 8 to 17 list sequences of exemplary SNP marker loci associated with STG QTL 2. Example STG and non-STG alleles of these marker loci are listed in Table 3.

SEQ ID NOs: 18 to 21 list sequences of exemplary SNP marker loci associated with STG QTL 3. SEQ ID NOs: 22 to 28 list sequences of exemplary SNP marker loci associated with STG QTL 4. SEQ ID NOs: 29 to 32 list sequences of exemplary SNP marker loci associated with STG QTL 5. SEQ ID NOs: 33 to 40 list sequences of exemplary SNP marker loci associated with STG QTL 6. SEQ ID NOs: 41 to 44 list sequences of exemplary SNP marker loci associated with STG QTL 7. Example STG and non-STG alleles of these marker loci are listed in Table 6.

DETAILED DESCRIPTION

Unless defined otherwise herein, terms are to be understood according to conventional usage by those of ordinary skill in the relevant art. Examples of resources describing many of the terms related to molecular biology used herein can be found in Alberts et al., Molecular Biology of The Cell, $5^{th}$ Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed., Oxford University Press: New York, 2002; and Lewin, Genes IX, Oxford University Press: New York, 2007. The nomenclature for DNA bases as set forth at 37 C.F.R. § 1.822 is used.

As used herein, terms in the singular and the singular forms "a," "an," and "the," for example, include plural referents unless the content clearly dictates otherwise. Thus, for example, reference to "plant," "the plant," or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

As used herein, a "cotton plant" refers to a plant of the genus *Gossypium.*

As used herein, "staygreen" is a term used to describe a plant phenotype, e.g., whereby leaf senescence (most easily distinguished by yellowing of the leaf associated with chlorophyll degradation) is delayed compared to a standard reference. See, Thomas and Howarth, Five ways to stay green. *Journal of Experimental Botany,* 51:329-337 (2000). Staygreen trait can be characterized using the staygreen index shown in Example 1 and Table 1. For example, a cotton plant exhibiting a staygreen trait under water deficit conditions comprises a leaf color selected from the group consisting of 135B, 134A, 140A, 140B, and 142A. A cotton plant exhibits a moderate staygreen trait when it comprises a leaf color of 142A under water deficit conditions. Unless specified otherwise, all color scores described herein are according to the R.H.S. Colour Chart of The Royal Horticultural Society of London (R.H.S.), 2007, 5th Edition. Alternative methods that can be used to characterize a staygreen trait include, but are limited to, leaf chlorophyll quantification and hyperspectral imaging.

As used herein, "drought," "drought conditions," "water-limited conditions," or "water-deficit conditions" refer to a stress condition having a moisture deficit in the soil.

One way to characterize drought conditions is Palmer Drought Severity Index (PDSI), which is a drought indicator to assess moisture status. PDSI uses temperature and precipitation data to calculate water supply and demand, and also incorporates soil moisture. Drought conditions, according to their different severity can has a PDSI of −1.0 to −1.9 (abnormally dry), a PDSI of −2.0 to −2.9 (moderate drought), a PDSI of −3.0 to −3.9 (severe drought), a PDSI of −4.0 to −4.9 (extreme drought), or a PDSI of −5.0 or less (exceptional drought).

As used herein, "fiber length" refers to the average of the longest 50 percent of fibers in a sample as measured by a fibergraph instrument. Long fibers are desirable because they produce greater yarn strength, aid in spinning finer yarns, and can be processed at higher speeds.

As used herein, "uniformity index (UI)" refers to a relative measure of the length uniformity of cotton fibers. Uniformity is calculated as the ratio of the average length of all fibers to the average length of the longest 50 percent of the fibers in the sample. High uniformity values indicate uniform fiber length distribution and are associated with a high-quality product and with low manufacturing waste.

As used herein, "fiber strength" refers to strength of cotton fibers. Strength values are reported in grams of force required to break a bundle of cotton fibers with the holding jaws separated by ⅛ inch. The size of the bundle of fibers is described in tex units. Yarn strength and ease of processing are positively correlated with strong-fibered cottons.

As used herein, fiber "elongation" is the degree of extension of the fibers before a break occurs when measuring strength. Fiber bundle elongation is correlated with yarn elongation but has an insignificant effect on yarn strength.

As used herein, "short fiber content" refers to the percentage (by weight) of fibers of 12.7 mm or less. The presence of excess amounts of short fibers can cause significant problems for a spinner, which problems include excess waste, loss of yarn strength, and increases in ends-down and yarn defects.

As used herein, "fallout rating" refers to the rating of how much cotton has fallen on the ground at harvest.

As used herein, "gin turnout" refers to fraction of lint in a machine harvested sample of seed cotton (lint, seed, and trash).

As used herein, "lint index" refers to the weight of lint per seed in milligrams As used herein, "lint percent" refers to the lint (fiber) fraction of seed cotton (lint and seed).

As used herein, "lint yield" or "fiber yield" refers to the measure of the quantity of fiber produced on a given unit of land. Lint yield can be measured in pounds of lint per acre or kilograms of lint per hectare.

As used herein, "stringout rating," also referred to as "storm resistance," refers to a visual rating prior to harvest of the relative looseness of the seed cotton held in the boll structure on the plant. The rating values are from 1 to 5 (tight to loose in the boll).

As used herein, "micronaire" refers to a measure of the fineness of the fiber. Cotton's resistance to air flow per unit mass is measured to determine micronaire. Within a cotton cultivar, micronaire can also be a measure of maturity. Micronaire differences are governed by changes in fiber perimeter or in cell wall thickness, or by changes in both. Within a variety, cotton fiber perimeter is fairly consistent and maturity will cause a change in micronaire. Consequently, micronaire has a high correlation with maturity within a variety of cotton. Maturity is the degree of development of cell wall thickness. Micronaire may not have a good correlation with maturity between varieties of cotton having different fiber perimeter. Micronaire values range from about 2.0 to 6.0 μg/inch.

As used herein, "fiber maturity ratio" refers to the degree of wall thickening. The relative wall thickness (e.g., the area of the cell wall to that of a circle with the same perimeter as the fiber, or the ratio of the cell wall thickness to the overall 'diameter' of the fiber) can be measured by an instrument called High Volume Instrument (HVI).

As used herein, "boll open percent" refers to the percentage of bolls that are open at a given time. Lower percentage generally indicates late relative maturity.

As used herein, "plant" refers to a whole plant or a cell or tissue culture derived from a plant, comprising any of: whole plants, plant components or organs (e.g., leaves, stems, roots, etc.), plant tissues, seeds, plant cells, and/or progeny of the same. A progeny plant can be from any filial generation, e.g., $F_1$, $F_2$, $F_3$, $F_4$, $F_5$, $F_6$, $F_7$, etc. A plant cell is a biological cell of a plant, taken from a plant or derived through culture from a cell taken from a plant.

As used herein, "germplasm" refers to living sources of genetic material. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leaves, stems, pollen, ovules, or cells that can be cultured into a whole plant.

As used herein, the phrase "associated with" or "linked to" refers to a recognizable and/or assayable relationship between two entities. For example, the phrase "associated with staygreen" refers to a trait, locus, gene, allele, marker, phenotype, etc., or the expression thereof, the presence or absence of which can influence an extent, degree, and/or rate at which a plant or a part of interest thereof that has a staygreen trait. As such, a marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with staygreen" refers to a marker whose presence or absence can be used to predict whether and to what extent a plant will display a staygreen phenotype under appropriate environment.

As used herein, a centimorgan ("cM") is a unit of measure of recombination frequency and genetic distance between two loci. One cM is equal to a 1% chance that a marker at one genetic locus will be separated from a marker at, a second locus due to crossing over in a single generation. Genetic distances can be calculated from recombination values using the Kosambi function (Kosambi, The estimation of map distances from recombination values. *Annals of Eugenics,* 12:172-75 (1944)).

As used herein, "closely linked" means that the marker or locus is within about 20 cM, 10 cM, 5 cM, 1 cM, 0.5 cM, or less than 0.5 cM of another marker or locus. For example, 20 cM means that recombination between the marker and the locus with a frequency of equal to or less than about 20%.

As used herein, the term "chromosome interval" designates a contiguous linear span of genomic DNA that resides on a single chromosome.

As used herein, "adjacent", when used to describe a nucleic acid molecule that hybridizes to DNA containing a polymorphism, refers to a nucleic acid that hybridizes to DNA sequences that directly abut the polymorphic nucleotide base position. For example, a nucleic acid molecule that can be used in a single base extension assay is "adjacent" to the polymorphism.

As used herein, "locus" is a chromosome region where a polymorphic nucleic acid, trait determinant, gene or marker is located. The loci of this disclosure comprise one or more polymorphisms in a population; e.g., alternative alleles are present in some individuals. A "gene locus" is a specific chromosome location in the genome of a species where a specific gene can be found.

As used herein, "allele" refers to an alternative nucleic acid sequence at a particular locus. The length of an allele can be as small as 1 nucleotide base, but is typically larger. For example, a first allele can occur on one chromosome, while a second allele occurs on a second homologous chromosome, e.g., as occurs for different chromosomes of a heterozygous individual, or between different homozygous or heterozygous individuals in a population.

As used herein, a "staygreen allele" is an allele at a particular locus that confers, or contributes to, a staygreen trait, or alternatively, is an allele that allows the identification of plants that comprise a staygreen trait. For example, a staygreen marker allele can be a marker allele that segregates with a staygreen trait. A staygreen allelic form of a chromosome is a chromosome interval that includes a nucleotide sequence that contributes to staygreen at one or more genetic loci physically located in the chromosome interval.

As used herein, "crossed" or "cross" means to produce progeny via fertilization (e.g. cells, seeds or plants) and includes crosses between plants (sexual) and self-fertilization (selfing).

As used herein, "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. (Ragot et al., Marker-assisted Backcrossing: A Practical Example. *Techniques Et Utilisations Des Marqueurs Moleculaires Les Colloques,* 72:45-56 (1995); and Openshaw et al., Marker-assisted Selection in Backcross Breeding, in *Proceedings Of The Symposium "Analysis of Molecular Marker Data,"* pp. 41-43 (1994)). The initial cross gives rise to the $F_1$ generation. The term "BC1" refers to the second use of the recurrent parent, "BC2" refers to the third use of the recurrent parent, and so on. In an aspect, a backcross is performed repeatedly, with a progeny individual of each successive backcross generation being itself backcrossed to the same parental genotype.

As used herein, "elite line" means any line that has resulted from breeding and selection for superior agronomic performance. Similarly, an "elite germplasm" or elite strain of germplasm is an agronomically superior germplasm. Numerous elite lines are available and known to those of skill in the art of cotton breeding, such as DP 555 BG/RR, DP 445 BG/RR, DP 444 BG/RR, DP 454 BG/RR, DP 161 B2RF, DP 141 B2RF, DP 0924 B2RF, DP 0935 B2RF, DP 121 RF, DP 174 RF (Deltapine); ST5599BR, ST5242BR, ST4554B2RF, ST4498B2RF, ST5458B2RF (Stoneville); FM9058F, FM9180B2F, FM1880B2F, FM1740B2F (FiberMax), PHY485WRF, PHY375WRF, PHY745WRF (Acala) (PhytoGen), and MCS0423B2RF, MCS0508B2RF (Cotton States).

As used herein, "genetic element" or "gene" refers to a heritable sequence of DNA, e.g., a genomic sequence, with functional significance. The term "gene" can also be used to refer to, e.g., a cDNA and/or an mRNA encoded by a genomic sequence, as well as to that genomic sequence.

As used herein, "genotype" is the genetic constitution of an individual (or group of individuals) at one or more genetic loci, as contrasted with the observable trait (phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome.

As used herein, a "haplotype" is the genotype of an individual at a plurality of genetic loci. Typically, the genetic loci described by a haplotype are physically and genetically linked, e.g., in the same chromosome interval. Selection based upon a haplotype can be more effective than selection based upon a single marker locus.

As used herein, "selecting" or "selection" in the context of marker-assisted selection or breeding refer to the act of picking or choosing desired individuals, normally from a population, based on certain pre-determined criteria.

As used herein, the terms "trait," "phenotypic trait," or "phenotype" refers to one or more detectable characteristics of a cell or organism which can be influenced by genotype. The phenotype can be observable to the naked eye, or by any other means of evaluation known in the art, e.g., microscopy, biochemical analysis, genomic analysis, transcriptional profiling etc. In some cases, a phenotype is directly controlled by a single gene or genetic locus, e.g., a "single gene trait." In other cases, a phenotype is the result of several genes.

As used herein, "linkage disequilibrium" (LD) refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Linked loci co-segregate more than 50% of the time, e.g., from about 51% to about 100% of the time. Linkage disequilibrium can be measured using any one of the methods provided in Hedrick, Gametic disequilibrium measures: proceed with caution. *Genetics,* 117:331-41(1987). The term "physically linked" is sometimes used to indicate that two loci, e.g., two marker loci, are physically present on the same chromosome. Advantageously, the two linked loci are located in close proximity such that recombination between homologous chromosome pairs does not occur between the two loci during meiosis with high frequency, e.g., such that linked loci cosegregate at least about 90% of the time, e.g., 91%, 92%, 93%, 94%, 95%, 96%, 97%, 98%, 99%, 99.5%, 99.75%, or more of the time.

As used herein, "marker assay" means a method for detecting a polymorphism at a particular locus using a particular method, e.g., measurement of at least one phenotype (such as seed color, flower color, or other visually detectable trait), restriction fragment length polymorphism (RFLP), single base extension, electrophoresis, sequence alignment, allelic specific oligonucleotide hybridization (ASO), random amplified polymorphic DNA (RAPD), microarray-based technologies, and nucleic acid sequencing technologies, etc.

As used herein, "marker assisted selection" (MAS) is a process by which phenotypes are selected based on marker genotypes. "Marker assisted selection breeding" refers to the process of selecting a desired trait or traits in a plant or plants by detecting one or more nucleic acids from the plant, where the nucleic acid is linked to the desired trait, and then selecting the plant or germplasm possessing those one or more nucleic acids.

As used herein, "polymorphism" means the presence of one or more variations in a population. A polymorphism may manifest as a variation in the nucleotide sequence of a nucleic acid or as a variation in the amino acid sequence of a protein. Polymorphisms include the presence of one or more variations of a nucleic acid sequence or nucleic acid feature at one or more loci in a population of one or more individuals. The variation may comprise but is not limited to one or more nucleotide base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs), a restriction fragment length polymorphism, and a tag SNP. A genetic marker, a gene, a DNA-derived sequence, a RNA-derived sequence, a promoter, a 5' untranslated region of a gene, a 3' untranslated region of a gene, microRNA, siRNA, a tolerance locus, a satellite marker, a transgene, mRNA, ds mRNA, a transcriptional profile, and a methylation pattern (DNA or histone methylation) may also comprise polymorphisms. In addition, the presence, absence, or variation in copy number of the preceding may comprise polymorphisms.

As used herein, "SNP" or "single nucleotide polymorphism" means a sequence variation that occurs when a single nucleotide (A, T, C, or G) in the genome sequence is altered or variable. "SNP markers" exist when SNPs are mapped to sites on the genome.

As used herein, "marker" or "molecular marker" or "marker locus" is a term used to denote a nucleic acid or amino acid sequence that is sufficiently unique to characterize a specific locus on the genome. Any detectable polymorphic trait can be used as a marker so long as it is inherited differentially and exhibits linkage disequilibrium with a phenotypic trait of interest. A number of markers and integrated genetic maps have been developed for various cotton species See US 2014/0255922 A1; Wang et al., "A Whole-Genome DNA Marker Map for Cotton Based on the D-Genome Sequence of *Gossypium raimondii* L." G3 (Bethesda) 3:1759-67 (2013); Blenda et al., "A High Density Consensus Genetic Map of Tetraploid Cotton That Integrates Multiple Component Maps through Molecular Marker Redundancy Check," *PLoS One,* 7(9):e45739 (2012); Yu et al., "Genome structure of cotton revealed by a genome-wide SSR genetic map constructed from a $BC_1$ population between *Gossypium hirsutum* and *G. barbadense,*" *BMC Genomics,* 12:15 (2011); Brubaker et al., "Comparative genetic mapping of allotetraploid cotton and its diploid progenitors," *Genome* 42:184-203 (1999).

All markers are used to define a specific locus in cotton genomes. Large numbers of these markers have been mapped. Each marker is therefore an indicator of a specific segment of DNA, having a unique nucleotide sequence. The map positions provide a measure of the relative positions of particular markers with respect to one another. When a trait is stated to be linked to a given marker it will be understood that the actual DNA segment whose sequence affects the trait generally co-segregates with the marker. More precise and definite localization of a trait can be obtained if markers are identified on both sides of the trait. By measuring the appearance of the marker(s) in progeny of crosses, the existence of the trait can be detected by relatively simple molecular tests without actually evaluating the appearance of the trait itself, which can be difficult and time-consuming because the actual evaluation of the trait requires growing plants to a stage and/or under environmental conditions where the trait can be expressed. Molecular markers have been widely used to determine genetic composition in cotton. Additional markers can also be designed and tested based on the available genome sequences of various cotton species. See Zhang et al., "Sequencing of allotetraploid cotton (*Gossypium hirsutum* L. acc. TM-1) provides a resource for fiber improvement," *Nature Biotechnology,* 33:531-537 (2015); Li et al., "Genome sequence of cultivated Upland cotton (*Gossypium hirsutum* TM-1) provides insights into genome evolution," *Nature Biotechnology,* 33:524-530 (2015); Li, F. et al. Genome sequence of the cultivated cotton *Gossypium arboreum. Nature Genetics,* 46, 567-572 (2014); Wang, K. et al. The draft genome of a diploid cotton *Gossypium raimondii. Nature Genetics,* 44:1098-1103 (2012); and references cited therein. Whole genome sequencing efforts also help speed up the identification of sequence polymorphisms and development of new SNP markers.

In an aspect, a marker used herein exhibits a LOD score of 2 or greater, 3 or greater, 4 or greater, 5 or greater, 6 or greater, 7 or greater, 8 or greater, or 9 or greater with a staygreen QTL disclosed herein, measured using a method known in the art such as Qgene Version 2.23 (1996) and default parameters.

As used herein, a "genetic recombination frequency" is the frequency of a crossing over event (recombination) between two genetic loci. Recombination frequency can be observed by following the segregation of markers and/or traits following meiosis. In some cases, two different markers can have the same genetic map coordinates. In that case, the two markers are in such close proximity to each other that recombination occurs between them with such low frequency that it is undetected.

As used herein, "mapping" is the process of defining the linkage relationships of loci through the use of genetic markers, populations segregating for the markers, and standard genetic principles of recombination frequency.

As used herein, "genetic mapping" is the process of defining the linkage relationships of loci through the use of genetic markers, populations segregating for the markers, and standard genetic principles of recombination frequency.

A "genetic map location" is a location on a genetic map relative to surrounding genetic markers on the same linkage group where a specified marker can be found within a given species. In contrast, a "physical map" of the genome refers to absolute distances (for example, measured in base pairs or isolated and overlapping contiguous genetic fragments, e.g., contigs). In general, the closer two markers or genomic loci are on the genetic map, the closer they lie to one another on the physical map. A physical map of the genome does not take into account the genetic behavior (e.g., recombination frequencies) between different points on the physical map. A lack of precise proportionality between genetic distances and physical distances can exist due to the fact that the likelihood of genetic recombination is not uniform throughout the genome; some chromosome regions are cross-over "hot spots," while other regions demonstrate only rare recombination events, if any. Genetic mapping variability can also be observed between different populations of the same crop species. In spite of this variability in the genetic map that may occur between populations, genetic map and marker information derived from one population generally remains useful across multiple populations in identification of plants with desired traits, counter-selection of plants with undesirable traits and in MAS breeding. As one of skill in the art will recognize, recombination frequencies (and as a result, genetic map positions) in any particular population are not static. The genetic distances separating two markers (or a marker and a QTL) can vary depending on how the map positions are determined. For example, variables such as the parental mapping populations used, the software used in the marker mapping or QTL mapping, and the parameters input by the user of the mapping software can contribute to the QTL marker genetic map relationships. However, it is not intended that the disclosure be limited to any particular mapping populations, use of any particular software, or any particular set of software parameters to determine linkage of a particular marker or chromosome interval with a desired phenotype. It is well within the ability of one of ordinary skill in the art to extrapolate the novel features described herein to any gene pool or population of interest, and using any particular software and software parameters. Indeed, observations regarding genetic markers and chromosome intervals in populations in addition to those described herein are readily made using the teaching of the present disclosure.

As used herein, "primer" refers to an oligonucleotide (synthetic or occurring naturally), which is capable of acting as a point of initiation of nucleic acid synthesis or replication along a complementary strand when placed under conditions in which synthesis of a complementary strand is catalyzed by a polymerase. Typically, primers are about 10 to 30 nucleotides in length, but longer or shorter sequences can be employed. Primers may be provided in double-stranded form, though the single-stranded form is more typically used. A primer can further contain a detectable label, for example a 5' end label.

As used herein, "probe" refers to an oligonucleotide (synthetic or occurring naturally) that is complementary (though not necessarily fully complementary) to a polynucleotide of interest and forms a duplex structure by hybridization with at least one strand of the polynucleotide of interest. Typically, probes are oligonucleotides from 10 to 50 nucleotides in length, but longer or shorter sequences can be employed. A probe can further contain a detectable label.

As used herein, a "population of plants" or "plant population" means a set comprising any number, including one, of individuals, objects, or data from which samples are taken for evaluation. Most commonly, the terms relate to a breeding population of plants from which members are selected and crossed to produce progeny in a breeding program. A population of plants can include the progeny of a single breeding cross or a plurality of breeding crosses, and can be either actual plants or plant derived material, or in silico representations of the plants. The population members need not be identical to the population members selected for use in subsequent cycles of analyses or those ultimately selected to obtain final progeny plants. Often, a plant population is derived from a single biparental cross, but may also derive from two or more crosses between the same or different parents. Although a population of plants may comprise any number of individuals, those of skill in the art will recognize that plant breeders commonly use population sizes ranging from one or two hundred individuals to several thousand, and that the highest performing 5-20% of a population is what is commonly selected to be used in subsequent crosses in order to improve the performance of subsequent generations of the population.

As used herein, "cultivar" and "variety" are used synonymously and mean a group of plants within a species (e.g., *G. hirsutum*) that share certain genetic traits that separate them from other possible varieties within that species. Cotton cultivars can be inbreds or hybrids.

As used herein, "introgression" or "introgressing" refers to the transmission of a desired allele of a genetic locus from one genetic background to another.

As used herein, "quantitative trait locus (QTL)" or "quantitative trait loci" (QTLs) refer to a genetic domain that effects a phenotype that can be described in quantitative terms and can be assigned a "phenotypic value" which corresponds to a quantitative value for the phenotypic trait.

As used herein, "single gene converted" or "single gene conversion" refers to plants that are developed using a plant breeding technique known as backcrossing, or via genetic engineering, wherein essentially all of the desired morphological and physiological characteristics of a variety are recovered in addition to the single gene transferred into the variety via the backcrossing technique or via genetic engineering.

Cotton is unique among crop plants in that four separate species in the genus *Gossypium* (Malvaceae) have been independently domesticated and cultivated for commercial lint fiber production. Most cotton fiber production around the world is concentrated in a pair of species, *G. hirsutum* (commonly known as short staple or upland cotton) and *G. barbadense* (commonly known as extra long staple (ELS) or, in the United States, as pima cotton), with small roles for another pair, *G. arboreum* and *G. herbaceum*. Both *G. hirsutum* and *G. barbadense* are tetraploids derived from a hypothetical common ancestor that formed from the combination of an invasive diploid A-genome species and a native diploid D-genome species. Both *G. arboreum* and *G. herbaceum* are A-genome diploid species. *G. hirsutum* 'Upland cotton' is the primary source of cotton fiber, accounting for about 97% of the world production (NCC 2006). *G. barbadense*, the other domesticated allotetraploid, yields an extra-long staple or extra-fine quality cotton fiber that makes about 3% of the total world cotton market.

In one aspect, cotton plants disclosed herein from the species *G. hirsutum* and its subspecies. In an additional aspect, cotton plants disclosed herein are from the group *G. arboreum* L., otherwise known as tree cotton. In another aspect, cotton plants disclosed herein are from the group *G. barbadense* L., otherwise known as American pima or Egyptian cotton. In another aspect, cotton plants disclosed herein are from the group *G. herbaceum* L., otherwise known as levant cotton. *Gossypium* or cotton plants can include hybrids, inbreds, partial inbreds, or members of defined or undefined populations.

Staygreen is a desirable trait in commercial agriculture, e.g., a desirable trait associated with grain filling. Five distinct types of staygreen have been described, including Types A, B, C, D, and E (see, e.g., Thomas and Smart, Crops that stay green. *Annals of Applied Biology,* 123:193-219 (1993); and Thomas and Howarth Five ways to stay green, *Journal of Experimental Botany* 51:329-337 (2000)). In Type A staygreen, initiation of the senescence program is delayed, but then proceeds at a normal rate. In Type B staygreen, while initiation of the senescence program is unchanged, the progression is comparatively slower. In Type C staygreen, chlorophyll is retained even though senescence (as determined through measurements of physiological function such as photosynthetic capacity) proceeds at a normal rate. Type D staygreen is more artificial in that killing of the leaf (i.e., by freezing, boiling or drying) prevents initiation of the senescence program, thereby stopping the degradation of chlorophyll. In Type E staygreen, initial levels of chlorophyll are higher, while initiation and progression of leaf senescence are unchanged, thereby giving the illusion of a relatively slower progression rate. Type A and B are functional staygreens, as photosynthetic capacity is maintained along with chlorophyll content, and these are the types associated with increased yield and drought tolerance in sorghum. Despite the potential importance of this trait, in particular the benefits associated with increasing yield and drought tolerance, very little progress has been made in understanding the biochemical, physiological or molecular basis for genetically determined staygreen.

Staygreen trait has been documented in several cereal crops including sorghum (*Sorghum bicolor* L.), pearl millet (*Pennisetum glaucum* L.), rice (*Oryza sativa* L.), oat (*Avena sativa* L.), wheat (*Triticum aestivum* L.), and maize (*Zea mays* L.). A positive association between the green leaf area duration and yield under stress has been documented in wheat (Evans et al. Wheat. p. 101-150. In L. T. Evans (ed.) *Crop physiology: Some case histories*. Cambridge University Press, Cambridge, UK. (1975)); maize (Tollenaar and Daynard, Leaf senescence in short-season maize hybrids. *Canadian Journal of Plant Science,* 58:869-874 (1978); Wolfe et al., Interactive water and nitrogen effects on senescence of maize. I. Leaf area duration. *Agronomy Journal,* 80:859-864 (1988)); oat (Helsel and Frey, Grain yield variations in oats associated with differences in leaf area duration among oat lines. *Crop Science,* 18:765-769 (1978)); and sorghum, (Henzell et al., Relationships between yield and non-senescence (staygreen) in some grain sorghum hybrids grown under terminal drought stress, p. 355-358. In M. A. Foale, R. G. Henzell and P. N. Vance (ed.) *Proceedings of the Second Australian Sorghum Conference, Gatton*, Feb. 4-6, 1992. Australian Institute of Agricultural Science, Melbourne. Occasional Publication No. 68).

More extensive work has been done on staygreen in sorghum. Green leaf area at maturity is an indicator of post-anthesis drought resistance in sorghum (Rosenow et al., "Drought tolerant sorghum and cotton germplasm." *Agricultural Water Management,* 7:207-222 (1983); Henzell et al., (1992) supra). Several sorghum staygreen genotypes have been identified which exhibit a delay in leaf senescence during grain filling and maturation. See Duncan et al., Descriptive comparison of senescent and non-senescent sorghum genotypes. *Agronomy Journal,* 73:849-853 (1981). Staygreen genotypes in sorghum continue to fill their grain normally under drought conditions. If staygreen plants can maintain photosynthesis for longer time than normal non-staygreen types, whether the longer period of photosynthesis translates into higher yields has been a topic of several studies in sorghum. In 2000, Borrell et al. demonstrated staygreen sorghum lines were able to produce 47% more post-anthesis biomass and had higher grain yields than the non-staygreen lines when they were exposed to drought stress. See Borrell et al. Does maintaining green leaf area in sorghum improve yield under drought? II. Dry matter production and yield. *Crop Science,* 40:1037-1048 (2000). However, when comparing these lines under well-irrigated conditions, there was no yield advantage for the staygreen lines over the non-staygreen lines.

Molecular markers have been used to identify QTLs associated with staygreen in sorghum. Four major QTLs have been found in a B35 inbred sorghum staygreen donor line. These QTLs had consistent effects in different genetic and environment backgrounds and accounted for up to 53.5% phenotype variance. See Subudhi et al., Quantitative trait loci for the stay-green trait in sorghum (*Sorghum bicolor* L. Moench): consistency across genetic backgrounds and environments. *Theoretical Applied Genetics* 101:733-741(2000).

The staygreen phenotype has also been used as a selection criterion for the development of improved varieties of corn, particularly with regard to the development of drought-tolerance. See, e.g., Russell, Genetic improvement of maize yields. *Advances in Agronomy,* 46:245-298 (1991); and, Bruce et al. Molecular and physiological approaches to maize improvement for drought tolerance. *Journal of Experimental Botany,* 53:13-25 (2002).

Attempts to genetically engineer a staygreen trait in cotton using genes from *Arabidopsis* have been reported. Yan et al. (2004) introduced an *Arabidopsis* gene encoding a 14-3-3 protein, GF14λ, into cotton. The overexpression of GF14λ, in cotton showed a staygreen phenotype. The GF14λ-expressing cotton plants displayed increased water-stress tolerance and maintained higher photosynthetic rates under water stress conditions. See Yan et al., Overexpression of the *Arabidopsis* 14-3-3 protein GF14λ, in cotton leads to a 'Stay-green' phenotype and improves stress tolerance under moderate drought conditions. *Plant and Cell Physiology,* 45:1007-1014 (2004). There is a need to identify non-transgenic staygreen trait and QTLs, and to develop molecular markers for marker-assisted breeding of this trait.

In one aspect, this disclosure provides a method of creating a population of cotton plants or seeds, which method comprising the steps of: (a) genotyping a first population of cotton plants or seeds at a marker locus associated with a staygreen (STG) quantitative trait locus (QTL) selected from the group consisting of STG QTLs 1 to 7; (b) selecting from the first population one or more cotton plants or seeds comprising an STG allele of the marker locus; and (c) producing from the selected one or more cotton plants or seeds a second population of cotton plants or seeds comprising the STG QTL. In an aspect, a method comprises genotyping a first population of cotton plants or seeds at a marker locus associated with STG QTL 1, which STG QTL 1 is located in a chromosomal interval flanked by any two of marker loci selected from the group consisting of SEQ ID NOs: 1 to 7. In another aspect, a method comprises genotyping a first population of cotton plants or seeds at a marker locus located in a chromosomal interval flanked by any two of marker loci selected from the group consisting of SEQ ID NOs: 1 to 7. In an aspect, a method comprises genotyping a first population of cotton plants or seeds at a marker locus associated with STG QTL 2, which STG QTL 2 is located in a chromosomal interval flanked by any two of marker loci selected from the group consisting of SEQ ID NOs: 8 to 17. In another aspect, a method comprises genotyping a first population of cotton plants or seeds at a marker locus located in a chromosomal interval flanked by any two of marker loci selected from the group consisting of SEQ ID NOs: 8 to 17. In an aspect, a method comprises genotyping a first population of cotton plants or seeds at a marker locus associated with STG QTL 3, which STG QTL 3 is located in a chromosomal interval flanked by any two of marker loci selected from the group consisting of SEQ ID NOs: 18 to 21. In another aspect, a method comprises genotyping a first population of cotton plants or seeds at a marker locus located in a chromosomal interval flanked by any two of marker loci selected from the group consisting of SEQ ID NOs: 18 to 21. In an aspect, a method comprises genotyping a first population of cotton plants or seeds at a marker locus associated with STG QTL 4, which STG QTL 4 is located in a chromosomal interval flanked by any two of marker loci selected from the group consisting of SEQ ID NOs: 22 to 28. In another aspect, a method comprises genotyping a first population of cotton plants or seeds at a marker locus located in a chromosomal interval flanked by any two of marker loci selected from the group consisting of SEQ ID NOs: 22 to 28. In an aspect, a method comprises genotyping a first population of cotton plants or seeds at a marker locus associated with STG QTL 5, which STG QTL 5 is located in a chromosomal interval flanked by any two of marker loci selected from the group consisting of SEQ ID NOs: 29 to 32. In another aspect, a method comprises genotyping a first population of cotton plants or seeds at a marker locus located in a chromosomal interval flanked by any two of marker loci selected from the group consisting of SEQ ID NOs: 29 to 32. In an aspect, a method comprises genotyping a first population of cotton plants or seeds at a marker locus associated with STG QTL 6, which STG QTL 6 is located in a chromosomal interval flanked by any two of marker loci selected from the group consisting of SEQ ID NOs: 33 to 40. In another aspect, a method comprises genotyping a first population of cotton plants or seeds at a marker locus located in a chromosomal interval flanked by any two of marker loci selected from the group consisting of SEQ ID NOs: 33 to 40. In an aspect, a method comprises genotyping a first population of cotton plants or seeds at a marker locus associated with STG QTL 7, which STG QTL 7 is located in a chromosomal interval flanked by any two of marker loci selected from the group consisting of SEQ ID NOs: 41 to 44. In another aspect, a method comprises genotyping a first population of cotton plants or seeds at a marker locus located in a chromosomal interval flanked by any two of marker loci selected from the group consisting of SEQ ID NOs: 41 to 44.

In a further aspect, a method comprises genotyping a first population of cotton plants or seeds at a marker locus within about 20 cM, 15 cM, 10 cM, 5 cM, 4 cM, 3 cM, 2 cM, 1 cM, 0.5 cM, or less than 0.5 cM of any one of marker loci SEQ ID NOs: 1 to 44. In an aspect, a method further comprises: phenotyping the second population of cotton plants or seeds to confirm an STG trait. In an aspect, the second population of cotton plants exhibit under water deficit conditions a leaf color selected from the group consisting of 135B, 134A, 140A, 140B, and 142A. In an aspect, the second population of cotton plants exhibit under water deficit conditions a leaf color selected from the group consisting of 135B, 134A, 140A, and 140B. In an aspect, step (a) of a method comprises a marker assay. In another aspect, step (a) of a method comprises detecting a haplotype. In an aspect, a haplotype comprises STG alleles of any two, three, four, five or more of marker loci SEQ ID NOs: 1 to 7. In another aspect, a haplotype comprises STG alleles of any two, three, four, five or more of marker loci SEQ ID NOs: 8 to 17. In an aspect, a haplotype comprises STG alleles of any two, three, or four of marker loci SEQ ID NOs: 18 to 21. In another aspect, a haplotype comprises STG alleles of any two, three, four, five or more of marker loci SEQ ID NOs: 22 to 28. In an aspect, a haplotype comprises STG alleles of any two, three, or four of marker loci SEQ ID NOs: 29 to 32. In another aspect, a haplotype comprises STG alleles of any two, three, four, five or more of marker loci SEQ ID NOs: 33 to 40. In a further aspect, a haplotype comprises STG alleles of any two, three, or four of marker loci SEQ ID NOs: 41 to 44. In an aspect, step (a) comprises assaying a SNP marker. In another aspect, step (a) comprises the use of an oligonucleotide probe. In a further aspect, the oligonucleotide probe used is adjacent to a polymorphic nucleotide position in the marker locus being genotyped.

In an aspect, the STG QTLs disclosed herein provide post-anthesis drought or heat tolerance in the first, second, or both populations of cotton plants. In another aspect, the STG QTLs disclosed herein confer no yield penalty under water-sufficient conditions. In a further aspect, the STG QTLs disclosed herein delay the onset of senescence under water-limited conditions. In another aspect, the STG QTLs disclosed herein delay the rate of senescence under water-limited conditions. In an aspect, cotton plants comprising the STG QTLs disclosed herein comprise greener leaves compared to cotton plants without the STG QTL under similar water-sufficient conditions.

In an aspect, the seed or fiber yield of cotton plants comprising an STG QTL disclosed herein is about 3% or more, 5% or more, 8% or more, 10% or more, 12% or more, 15% or more, 17% or more, 20% or more, 25% or more, or 30% or more higher than the seed or fiber yield of cotton plants without an STG QTL under water-limited conditions. In another aspect, the seed or fiber yield of cotton plants comprising an STG QTL disclosed herein is between 3% and 4%, between 4% and 5%, between 5% and 6%, between 6% and 7%, between 7% and 8%, between 8% and 9%, or between 9% and 10% higher than the seed or fiber yield of cotton plants without an STG QTL under water-limited conditions. In a further aspect, the seed or fiber yield of cotton plants comprising an STG QTL disclosed herein is between 3% and 10%, between 4% and 10%, between 5% and 10%, between 6% and 10%, between 7% and 10%, or between 8% and 10% higher than the seed or fiber yield of cotton plants without an STG QTL under water-limited conditions.

In a further aspect, an STG QTL disclosed herein has no negative impact in the selected progeny plant over at least one or more, two or more, three or more, four or more, five or more, six or more, or seven or more traits at maturity selected from the group consisting of plant height, micronaire, bolls open percentage, fiber elongation percentage, fiber maturity ratio, short fiber content, fiber length, fiber strength, uniformity index, lint percentage, and stringout rating, under either water-limited conditions or water-sufficient conditions. In an additional aspect, an STG QTL disclosed herein has no negative impact over one or more fiber characteristics selected from the group consisting of strength, length, fiber fineness, fiber maturity ratio, immature fiber content, fiber uniformity, and micronaire.

In one aspect, this disclosure provides a method of introgressing an STG QTL, the method comprising: (a) crossing a first cotton plant comprising an STG QTL selected from the group consisting of STG QTLs 1 to 7, with a second cotton plant of a different genotype to produce one or more progeny plants or seeds; and (b) assaying the one or more progeny plants or seeds at a marker locus associated with the STG QTL; and (c) selecting a progeny plant or seed comprising the STG QTL. In an aspect, the first cotton plant is an inbred or a hybrid. In another aspect, the second cotton plant is an agronomically elite cotton plant. In an aspect, a method further comprises: (d) crossing the selected progeny plant with itself or the second plant to produce one or more further progeny plants or seeds; and (e) selecting a further progeny plant or seed comprising the STG QTL. In another aspect, step (e) comprises marker-assisted selection, optionally, with a marker within about 20 cM, 15 cM, 10 cM, 5 cM, 4 cM, 3 cM, 2 cM, 1 cM, 0.5 cM, or less than 0.5 cM of any one of STG QTLs 1 to 7. In an aspect, the production of the one or more further progeny plants or seeds comprises backcrossing. In another aspect, the backcrossing comprises 2 to 7 generations of backcrosses.

In another aspect, this disclosure provides a method for selecting a cotton plant or seed, the method comprising: (a) detecting in a population of cotton plants or seeds a cotton plant or seed comprising an STG allele of a marker locus associated with an STG QTL selected from the group consisting of STG QTLs 1 to 7; and (b) selecting the cotton plant or seed comprising the STG allele. In an aspect, a method comprises detecting an STG allele of a marker locus located in a chromosomal interval flanked by any two of marker loci selected from the group consisting of SEQ ID NOs: 1 to 7. In another aspect, a method comprises detecting an STG allele of a marker locus located in a chromosomal interval flanked by any two of marker loci selected from the group consisting of SEQ ID NOs: 8 to 17. In an aspect, a method comprises detecting an STG allele of a marker locus located in a chromosomal interval flanked by any two of marker loci selected from the group consisting of SEQ ID NOs: 18 to 21. In another aspect, a method comprises detecting an STG allele of a marker locus located in a chromosomal interval flanked by any two of marker loci selected from the group consisting of SEQ ID NOs: 22 to 28. In an aspect, a method comprises detecting an STG allele of a marker locus located in a chromosomal interval flanked by any two of marker loci selected from the group consisting of SEQ ID NOs: 29 to 32. In another aspect, a method comprises detecting an STG allele of a marker locus located in a chromosomal interval flanked by any two of marker loci selected from the group consisting of SEQ ID NOs: 33 to 40. In an aspect, a method comprises detecting an STG allele of a marker locus located in a chromosomal interval flanked by any two of marker loci selected from the group consisting of SEQ ID NOs: 41 to 44. In a further aspect, a method comprises detecting an STG allele of a marker locus within about 20 cM, 15 cM, 10 cM, 5 cM, 4 cM, 3 cM, 2 cM, 1 cM, 0.5 cM, or less than 0.5 cM of any one of marker loci SEQ ID NOs: 1 to 44. In yet a further aspect, a method comprises detecting an STG allele of a marker locus within about 20 cM, 15 cM, 10 cM, 5 cM, 4 cM, 3 cM, 2 cM, 1 cM, 0.5 cM, or less than 0.5 cM of any one of STG QTLs 1 to 7. In an aspect, step (a) comprises assaying a SNP marker. In another aspect, step (a) comprises the use of an oligonucleotide probe. In a further aspect, the oligonucleotide probe used is adjacent to a polymorphic nucleotide position in the marker locus being genotyped.

In a further aspect, this disclosure provides a method for evaluating a collection of cotton germplasm, the method comprising: (a) obtaining a collection of cotton germplasm; (b) isolating nucleic acids from each germplasm; (c) assaying the nucleic acids for one or more markers linked to or associated with an STG QTL selected from the group consisting of STG QTLs 1 to 7; (d) selecting germplasm having an STG QTL based on the marker assay. In another aspect, a method further comprises confirming that the selected germplasm has post-anthesis drought or heat tolerance. In an aspect, a method comprises assaying for one or more markers located in a chromosomal interval flanked by any two of marker loci selected from the group consisting of SEQ ID NOs: 1 to 7. In another aspect, a method comprises assaying for one or more markers located in a chromosomal interval flanked by any two of marker loci selected from the group consisting of SEQ ID NOs: 8 to 17. In an aspect, a method comprises assaying for one or more markers located in a chromosomal interval flanked by any two of marker loci selected from the group consisting of SEQ ID NOs: 18 to 21. In another aspect, a method comprises assaying for one or more markers located in a chromosomal interval flanked by any two of marker loci selected from the group consisting of SEQ ID NOs: 22 to 28. In an aspect, a method comprises assaying for one or more markers located in a chromosomal interval flanked by any two of marker loci selected from the group consisting of SEQ ID NOs: 29 to 32. In another aspect, a method comprises assaying for one or more markers located in a chromosomal interval flanked by any two of marker loci selected from the group consisting of SEQ ID NOs: 33 to 40. In an aspect, a method comprises assaying for one or more markers located in a chromosomal interval flanked by any two of marker loci selected from the group consisting of SEQ ID NOs: 41 to 44. In a further aspect, a method comprises assaying for one or more markers within about 20 cM, 15 cM, 10 cM, 5 cM, 4 cM, 3 cM, 2 cM, 1 cM, 0.5 cM, or less than 0.5 cM of any one of marker loci SEQ ID NOs: 1 to 44. In yet a further aspect, a method comprises assaying for one or more markers within about 20 cM, 15 cM, 10 cM, 5 cM, 4 cM, 3 cM, 2 cM, 1 cM, 0.5 cM, or less than 0.5 cM of any one of STG QTLs 1 to 7. In an aspect, a method comprise assaying for one or more SNP markers. In another aspect, step (c) comprises the use of an oligonucleotide probe. In a further aspect, the oligonucleotide probe used is adjacent to a polymorphic nucleotide position in the marker being genotyped.

In one aspect, this disclosure provides a method comprising providing a set of cotton seeds comprising one or more STG QTLs selected from the group consisting of STG QTLs 1 to 7, to a person desirous of planting the set of cotton seeds in a field plot prone to drought or heat stress. In an aspect, an STG QTL in such cotton seeds provides post-anthesis drought or heat tolerance. In another aspect, an STG QTL in such cotton seeds confers no yield penalty under water-sufficient conditions. In a further aspect, an STG QTL in such seeds delays the onset of senescence under water-limited conditions. In another aspect, an STG QTL in such seeds reduces the rate of senescence under water-limited conditions. In an aspect, cotton plants grown from such seeds comprise greener leaves compared to cotton plants without an STG QTL under similar water-sufficient conditions.

In another aspect, this disclosure provides a method of growing a population of cotton plants, the method comprising planting a population of cotton seeds comprising one or more introgressed STG QTLs selected from the group consisting of STG QTLs 1 to 7. In another aspect, this disclosure provides a method of growing a population of cotton plants in a field plot prone to drought or heat stress, the method comprising planting a population of cotton seeds comprising one or more introgressed STG QTLs selected from the group consisting of STG QTLs 1 to 7 in the field plot prone to drought or heat stress. In an aspect, a method further comprises obtaining a population of cotton seeds from a seed distributor. In another aspect, the planted cotton seeds are elite cotton seeds. In an aspect, the drought or heat stress starts after cotton plants grown from the cotton seeds flower. In an aspect, the introgressed one or more STG QTLs provide post-anthesis drought or heat tolerance. In a further aspect, the population of cotton seeds provide higher yield of seed, fiber, or both compared to cotton seeds not comprising the one or more introgressed STG QTLs when grown in the field plot.

In another aspect, this disclosure provides a method of reducing the cost of watering cotton plants, the method comprising: (a) growing a population of cotton plants comprising one or more introgressed STG QTLs selected from the group consisting of STG QTLs 1 to 7; and (b) reducing the amount of water supplied to the population of cotton plants after the cotton plants start flowering. In an aspect, the step (b) comprises reducing watering frequency. In another aspect, the step (b) comprises reducing the amount of water in each watering. In an aspect, a method further comprises adjusting defoliation treatment to increase defoliation rate and prepare for harvest. In an aspect, the reduction of watering has no significant impact over the yield of seed, fiber, or both from the population of cotton plants.

In a further aspect, this disclosure provides cotton plants or seeds comprising a staygreen trait when grown under water-limited conditions, and further comprising one or more, introgressed STG QTLs selected from the group consisting of STG QTLs 1 to 7. In an aspect, the introgressed STG QTLs are also present in or originate from one or more cotton germplasm selected from the group consisting of STG-001 and STG-002 having an ATCC deposit number of PTA-122486 and PTA-122487. In an aspect, the introgressed STG QTL is STG QTL 1 and is located in a chromosomal interval flanked by any two of marker loci selected from the group consisting of SEQ ID NOs: 1 to 7. In another aspect, the introgressed STG QTL is STG QTL 2 and is located in a chromosomal interval flanked by any two of marker loci selected from the group consisting of SEQ ID NOs: 8 to 17. In an aspect, the introgressed STG QTL is STG QTL 3 and is located in a chromosomal interval flanked by any two of marker loci selected from the group consisting of SEQ ID NOs: 18 to 21. In another aspect, the introgressed STG QTL is STG QTL 4 and is located in a chromosomal interval flanked by any two of marker loci selected from the group consisting of SEQ ID NOs: 22 to 28. In an aspect, the introgressed STG QTL is STG QTL 5 and is located in a chromosomal interval flanked by any two of marker loci selected from the group consisting of SEQ ID NOs: 29 to 32. In another aspect, the introgressed STG QTL is STG QTL 6 and is located in a chromosomal interval flanked by any two of marker loci selected from the group consisting of SEQ ID NOs: 33 to 40. In an aspect, the introgressed STG QTL is STG QTL 7 and is located in a chromosomal interval flanked by any two of marker loci selected from the group consisting of SEQ ID NOs: 41 to 44. In an aspect, the cotton plants or seeds disclosed herein are homozygous at one or more introgressed STG QTLs. In another aspect, the cotton plants or seeds disclosed herein are heterozygous at one or more introgressed STG QTLs. In an aspect, the disclosed cotton plants or seeds are transgenic. In another aspect, the disclosed cotton plants or seeds are non-transgenic. In an aspect, the disclosed cotton plants or seeds are hybrids. In another aspect, the disclosed cotton plants or seeds are inbreds. In a further aspect, the disclosed cotton plants or seeds are in an elite cotton background. In an aspect, the disclosed cotton plants or seeds are a single gene conversion of an existing elite cotton variety further comprising an STG QTL disclosed herein. In a further aspect, cotton plants or seeds comprising one or more STG QTLs disclosed herein exhibit higher photosynthetic rates under water stress conditions compared to control plants. In an aspect, cotton plants or seeds disclosed herein exhibit under water deficit conditions a leaf color selected from the group consisting of 135B, 134A, 140A, 140B, and 142A. In another aspect, cotton plants or seeds disclosed herein exhibit under water deficit conditions a leaf color selected from the group consisting of 135B, 134A, 140A, and 140B. In an aspect, cotton plants or seeds disclosed herein exhibit under water sufficient conditions a leaf color selected from the group consisting of 135B, 134A, 140A, 140B, and 142A. In another aspect, cotton plants or seeds disclosed herein exhibit under water sufficient conditions a leaf color selected from the group consisting of 135B, 134A, 140A, and 140B.

In an aspect, cotton plants or seeds disclosed herein exhibit post-anthesis drought or heat tolerance. In another aspect, cotton plants or seeds disclosed herein exhibit no yield penalty under water-sufficient conditions. In a further aspect, cotton plants or seeds disclosed herein exhibit a delayed onset of senescence under water-limited conditions. In another aspect, cotton plants or seeds disclosed herein exhibit a reduced rate of senescence under water-limited conditions. In an aspect, cotton plants or seeds disclosed herein exhibit comprise greener leaves compared to cotton plants without the STG QTL under similar water-sufficient conditions.

In an aspect, the seed or fiber yield of cotton plants disclosed herein comprising an STG QTL disclosed herein is about 3% or more, 5% or more, 8% or more, 10% or more, 12% or more, 15% or more, 17% or more, 20% or more, 25% or more, or 30% or more higher than the seed or fiber yield of cotton plants without a corresponding STG QTL under water-limited conditions. In another aspect, the seed or fiber yield of cotton plants disclosed herein is between 3% and 4%, between 4% and 5%, between 5% and 6%, between 6% and 7%, between 7% and 8%, between 8% and 9%, or between 9% and 10% higher than the seed or fiber yield of cotton plants without a corresponding STG QTL under water-limited conditions. In a further aspect, the seed or fiber yield of cotton plants disclosed herein is between 3% and 10%, between 4% and 10%, between 5% and 10%, between 6% and 10%, between 7% and 10%, or between 8% and 10% higher than the seed or fiber yield of cotton plants without a corresponding STG QTL under water-limited conditions. Water-limited conditions described herein can have different severity. In one aspect, drought or water-limited condition has a PDSI of −1.0 to −1.9 (abnormally dry). In another aspect, drought or water-limited condition has a PDSI of −2.0 to −2.9 (moderate drought). In one aspect, drought or water-limited condition has a PDSI of −3.0 to −3.9 (severe drought). In another aspect, drought or water-limited condition has a PDSI of −4.0 to −4.9 (extreme drought). In a further aspect, drought or water-limited condition has a PDSI of −5.0 or less (exceptional drought).

In a further aspect, cotton plants or seeds disclosed herein exhibit at maturity no significant differences over at least one or more, two or more, three or more, four or more, five or more, six or more, or seven or more traits selected from the group consisting of plant height, micronaire, bolls open percentage, fiber elongation percentage, fiber maturity ratio, short fiber content, fiber length, fiber strength, uniformity index, lint percentage, and stringout rating, under either water-limited conditions or water-sufficient conditions.

In an aspect, cotton plants or seeds disclosed herein exhibit an average staygreen index of 5 or below, 4.5 or below, 4 or below, 3.5 or below, 3 or below, 2.5 or below, 2 or below, 1.5 or below, or 1 or below under high water stress or low water stress. In another aspect, cotton plants or seeds disclosed herein exhibit an average staygreen index of between 1 and 5, between 2 and 4, between 1 and 4, between 1 and 3, between 1 and 2, between 2 and 5, between 3 and 4, between 3 and 5, or between 4 and 5, under high water stress or low water stress.

In an aspect, cotton plants or seeds disclosed herein exhibit an average lint yield of at least about 200, at least about 250, at least about 300, at least about 350, at least about 400, at least about 450, at least about 500, at least about 550, at least about 600, at least about 650, at least about 700, at least about 750, at least about 800, or at least about 850 kg/ha under high water stress. In an aspect, cotton plants or seeds disclosed herein exhibit an average lint yield of between 200 and 1000, between 300 and 900, between 400 and 800, between 500 and 700, between 300 and 1000, between 400 and 900, between 500 and 800, between 600 and 700, between 400 and 1000, between 500 and 900, between 600 and 800, between 300 and 500, between 300 and 600, or between 400 and 500 kg/ha under high water stress.

In an aspect, cotton plants or seeds disclosed herein exhibit an average lint yield of at least about 1200, at least about 1250, at least about 1300, at least about 1350, at least about 1400, at least about 1450, at least about 1500, at least about 1550, at least about 1600, at least about 1650, at least about 1700, at least about 1750, at least about 1800, or at least about 1850 kg/ha under low water stress. In another aspect, cotton plants or seeds disclosed herein exhibit an average lint yield of between 1200 and 2000, between 1300 and 1900, between 1400 and 1800, between 1500 and 1700, between 1300 and 2000, between 1400 and 1900, between 1500 and 1800, between 1600 and 1700, between 1400 and 2000, between 1500 and 1900, between 1600 and 1800, between 1300 and 1500, between 1300 and 1600, or between 1400 and 1500 kg/ha under high water stress.

In an aspect, cotton plants or seeds disclosed herein exhibit a micronaire of at least about 3.0, 3.5, 4.0, 4.5, 5.0, 5.5, or 6.0 μg/inch under high water stress orlow water stress. In an aspect, cotton plants or seeds disclosed herein exhibit a micronaire of about between 2 and 6, between 2 and 5, between 2 and 4, between 2 and 3, between 3 and 6, between 3 and 5, between 3 and 4, between 4 and 6, between 4 and 5, or between 5 and 6 μg/inch under high water stress or low water stress.

In an aspect, cotton plants or seeds disclosed herein exhibit an average bolls open percentage of at least about 15%, 17.5%, 20%, 22.5%, 25%, 27.5%, 30%, 35%, 40%, 45%, 50%, 55%, 60%, 65%, 70%, or 80% under high water stress or low water stress. In another aspect, cotton plants or seeds disclosed herein exhibit an average bolls open percentage of about between 15% and 80%, between 20% and 70%, between 30% and 60%, between 40% and 50%, between 15% and 20%, between 15% and 25%, between 20% and 30%, between 40% and 70%, between 50% and 60%, or between 50% and 55% under high water stress or low water stress.

In an aspect, cotton plants or seeds disclosed herein exhibit an elongation percentage of at least about 4%, 5%, 6%, 7%, 8%, 9%, 10%, 11%, or 12% under high water stress or low water stress. In another aspect, cotton plants or seeds disclosed herein exhibit an average bolls open percentage of about between 4% and 12%, between 5% and 11%, between 6% and 10%, between 7% and 9%, between 4% and 11%, between 4% and 10%, between 4% and 9%, between 4% and 8%, between 4% and 7%, between 5% and 12%, between 6% and 12%, between 7% and 12%, between 8% and 12%, between 9% and 12% or between 10% and 12% under high water stress or low water stress.

In an aspect, cotton plants or seeds disclosed herein exhibit a fiber maturity ratio (%) of at least about 60, 65, 70, 75, 80, 85, or 90 under high water stress or low water stress. In an aspect, cotton plants or seeds disclosed herein exhibit a fiber maturity ratio (%) of between 60 and 95, between 70 and 85, between 75 and 80, between 80 and 90, between 85 and 90, or between 80 and 85 under high water stress or low water stress.

In an aspect, cotton plants or seeds disclosed herein exhibit a short fiber content of at least about 6, 6.5, 7, 7.5, 8, 8.5, or 9 under high water stress or low water stress. In an aspect, cotton plants or seeds disclosed herein exhibit a short fiber content of between 6.0 and 9.5, between 7.0 and 8.5, between 7.5 and 8.0, between 8.0 and 9.0, between 8.5 and 9.0, or between 8.0 and 8.5 under high water stress or low water stress.

In an aspect, cotton plants or seeds disclosed herein exhibit an average fiber length of at least about 0.7, 0.8, 0.9, 1.0, 1.1, 1.2, 1.3, 1.4, 1.5, or 1.6 cm under high water stress or low water stress. In an aspect, cotton plants or seeds disclosed herein exhibit an average fiber length of between 0.7 and 1.6, between 0.8 and 1.5, between 0.9 and 1.4, between 1.0 and 1.3, between 1.1 and 1.2, between 1.1 and 1.3, between 1.1 and 1.4, between 1.1 and 1.5, between 1.1 and 1.6, between 1.2 and 1.3, between 1.2 and 1.4, between 1.3 and 1.4, between 1.4 and 1.5, between 0.7 and 1.1, between 0.8 and 1.1, between 0.9 and 1.1, between 1.0 and 1.1, between 0.9 and 1.1, or between 1.0 and 1.2 cm under high water stress or low water stress.

In an aspect, cotton plants or seeds disclosed herein exhibit an average fiber strength of at least about 15, 17.5, 20, 22.5, 25, 27.5, 30, 35, 40, 45, 50, 55, 60, 65, 70, or 80 g/tex under high water stress or low water stress. In another aspect, cotton plants or seeds disclosed herein exhibit an average bolls open percentage of about between 15 and 80, between 20 and 70, between 30 and 60, between 40 and 50, between 15 and 20, between 15 and 25, between 20 and 30, between 40 and 70, between 50 and 60, or between 50 and 55 g/tex under high water stress or low water stress.

In an aspect, cotton plants or seeds disclosed herein exhibit a uniformity index of at least about 60, 65, 70, 75, 80, 85, or 90 under high water stress or low water stress. In an aspect, cotton plants or seeds disclosed herein exhibit a uniformity index of between 60 and 95, between 70 and 85, between 75 and 80, between 80 and 90, between 85 and 90, or between 80 and 85 under high water stress or low water stress.

In an aspect, cotton plants or seeds disclosed herein exhibit an average lint percentage (%) of at least about 25, 30, 35, 40, 45, 50, 55, 60, 65, 70, or 80 under high water stress or low water stress. In another aspect, cotton plants or seeds disclosed herein exhibit an average bolls open percentage of about between 25 and 80, between 30 and 70, between 40 and 60, between 40 and 50, between 35 and 40, between 35 and 45, between 40 and 60, between 40 and 70, between 50 and 60, or between 50 and 55 under high water stress or low water stress.

In an additional aspect, cotton plants or seeds disclosed herein further exhibit improvement over one or more fiber characteristics selected from the group consisting of strength, length, fiber fineness, fiber maturity ratio, immature fiber content, fiber uniformity, and micronaire. In an additional aspect, cotton plants or seeds disclosed herein further exhibit improvement over fallout rating, gin turnout, lint index, lint percent, lint yield, stringout rating, or any combinations thereof.

Cotton plants or seeds disclosed herein may exhibit the characteristics of any relative maturity group. In an aspect, the maturity group is selected from the group consisting of early maturing varieties, mid season maturing varieties, and full season varieties.

In another aspect, this disclosure provides a container of cotton seeds described herein and a population of cotton plants described herein. A container of cotton seeds of the instant disclosure may contain any number, weight or volume of seeds. For example, a container can contain at least, or greater than, about 10, 25, 50, 100, 200, 300, 400, 500, 600, 700, 800, 900, 1000, 1500, 2000, 2500, 3000, 3500, 4000 or more seeds. Alternatively, the container can contain at least, or greater than, about 5 grams, 10 grams, 15 grams, 20 grams, 25 grams, 50 grams, 100 grams, 250 grams, 500 grams, or 1000 grams of seeds. Alternatively, the container can contain at least, or greater than, about 1 ounce, 5 ounces, 10 ounces, 1 pound, 2 pounds, 3 pounds, 4 pounds, 5 pounds or more seeds. Containers of cotton seeds may be any container available in the art. By way of non-limiting example, a container may be a box, a bag, a can, a packet, a pouch, a tape roll, a pail, a tube, or a bottle.

In an aspect, methods, cotton plants or seeds disclosed herein are used in combination with one or more pesticides including, but not limited to, herbicides, fungicides, insecticides, microbiocides, nematicides, insect repellents, bactericides, and other substances used to control pests. In another aspect, methods or cotton plants disclosed herein are used in combination with one or more triazoles, strobilurins, acylamino acids, pyrimidines, pyridines, arylphenyl ketones, amides, benzanilides, imidazoles, dinitrophenols, morpholines, phenylsulfamides and organophosphorus cpds, derivatives thereof and combinations thereof which may be applied as seed, foliar, drench, or drip treatments.

In one aspect, cotton seeds disclosed herein are untreated. In another aspect, cotton seeds disclosed herein can be subjected to various treatments. For example, the seeds can be treated to improve germination by priming the seeds or by disinfection to protect against seed borne pathogens. In another aspect, seeds can be coated with any available coating to improve, for example, plantability, seed emergence, and protection against seed borne pathogens. Seed coating can be any form of seed coating including, but not limited to, pelleting, film coating, and encrustments.

In a further aspect, the instant disclosure provides methods to enhance cotton plant performance under water deficit conditions by combining two or more staygreen QTLs disclosed herein. In an aspect, the combined staygreen QTLs have additive effects in providing drought tolerance. In another aspect, the combined staygreen QTLs have synergistic effects in providing drought tolerance. In a further aspect, the combination of two or more staygreen QTLs disclosed herein has no negative effects over cotton physiology, resistance, yield, or performance in general.

In one aspect, this disclosure provides cotton plant cells, tissues, and organs that are not reproductive material and do not mediate the natural reproduction of the plant. In another aspect, this disclosure also provides cotton plant cells, tissues, and organs that are reproductive material and mediate the natural reproduction of the plant. In another aspect, this disclosure provides cotton plant cells, tissues, and organs that cannot maintain themselves via photosynthesis. In another aspect, this disclosure provides somatic cotton plant cells. Somatic cells, contrary to germline cells, do not mediate plant reproduction.

The provided cells, tissues and organs may be from seed, fruit, leaf, cotyledon, hypocotyl, meristem, embryos, endosperm, root, shoot, stem, pod, flower, inflorescence, stalk, pedicel, style, stigma, receptacle, petal, sepal, pollen, anther, filament, ovary, ovule, pericarp, phloem, bud, or vascular tissue. In another aspect, this disclosure provides a cotton plant chloroplast. In a further aspect, this disclosure provides epidermal cells, stomata cell, trichomes, root hairs, a storage root, or a tuber. In another aspect, this disclosure provides a cotton protoplast.

Skilled artisans understand that cotton plants naturally reproduce via seeds, not via asexual reproduction or vegetative propagation. In one aspect, this disclosure provides cotton endosperm. In another aspect, this disclosure provides cotton endosperm cells. In a further aspect, this disclosure provides a male or female sterile cotton plant, which cannot reproduce without human intervention.

In a further aspect, this disclosure provides processed products made from the disclosed cotton plants. Such products include, but are not limited to, meal, oil, plant extract, starch, or fermentation or digestion products. In another aspect, this disclosure also provides a cotton meal, which is substantially oil free and which is produced using the oilseed of any of the plants disclosed herein. In another aspect, this disclosure also provides a method of providing a cotton meal by crushing oilseed of any of the plants disclosed herein.

In a further aspect, this disclosure provides cotton products, e.g., fiber, clothing, fabrics such as velvet, corduroy, chambray, velour, jersey, and flannel. Further exemplary cotton products include denim jeans, socks, towels, t-shirts, bed sheets, and underwear. Additional exemplary cotton products include tents, car tire cord, fishnets, and book binding. Also provided herein are products made from cotton seeds, for example, cottonseed oil for cooking and feed for livestock. Further exemplary cotton seed derived products include soap, margarine, emulsifiers, cosmetics, pharmaceuticals, rubber, paint, water proofing, and candles.

Various cotton lines disclosed herein can be used to transmit a staygreen trait to new varieties using various cross pollination and selection methods. Breeders can also obtain hybrids using cotton plants described here. Using standard crossing, backcrossing, and selection techniques, those of skill in the art may obtain commercial cotton varieties with various desirable traits besides staygreen. For example, breeders may obtain commercial cotton lines with staygreen and additional traits such as tolerance to other abiotic stresses and new herbicide tolerance, higher fiber (lint) yield, earlier maturity, improved fiber quality, and resistance to insects. Additional traits combinable with staygreen may be selected from the following: abiotic stress tolerance, e.g., salt tolerance, cold tolerance, heat tolerance, storm tolerance, nutrient deficiency, and the like, male sterility, female sterility, fertility restoration, morphological traits, e.g., plant type, leaf size, leaf color, leaf thickness, leaf shape, leaf hairiness, stem hairiness, petal color, petal spot, pollen color, glands, fiber color, root length, root thickness, and the like, physiological traits, e.g., seed dormancy, vigor, stand count, cold germination, plant mass (dry weight), chlorophyll content, leaf senescence, and the like, fiber quality traits, e.g., fiber length, fiber strength, fiber fineness, short fiber content, fiber elongation, fiber color grade, fiber uniformity, and the like, and seed quality traits, e.g., seed protein content, seed oil content, seed gossypol content, and the like.

Cotton plants or lines disclosed herein can also be genetically engineered to express various phenotypes of agronomic interest. Exemplary genes implicated in this regard include, but are not limited to, genes that confer resistance to pests or disease, genes that confer resistance or tolerance to an herbicide, genes that control male sterility, genes that affect abiotic stress resistance, and other genes and transcription factors that affect plant growth and agronomic traits such as yield, flowering, plant growth, or plant architecture.

Cotton Transformation

Cotton plants disclosed herein can also be genetically transformed. Numerous methods for plant transformation have been developed including biological and physical plant transformation protocols. See, for example, Mild, et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber, et al., "Vectors for Plant Transformation" in *Methods in Plant Molecular Biology and Biotechnology*, Glick B. R. and Thompson, J. E. Eds. (CRC Press, Inc., Boca Raton, 1993) pages 89-119.

A. *Agrobacterium*-Mediated Transformation—One method for introducing an expression vector into plants is based on the natural transformation system of *Agrobacterium*. See, e.g., Horsch, et al., A Simple and General Method for Transferring Genes into Plants, Science 227:1229-1231 (1985). *A. tumefaciens* and *A. rhizogenes* are plant pathogenic soil bacteria which genetically transform plant cells. Descriptions of *Agrobacterium* vector systems and methods for *Agrobacterium*-mediated gene transfer are provided by, for example, U.S. Pat. No. 5,563,055 (Townsend and Thomas), incorporated herein by reference in its entirety.

B. Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles. The expression vector is introduced into plant tissues with a biolistic device that accelerates the microprojectiles to speeds of 300 to 600 m/s which is sufficient to penetrate plant cell walls and membranes.

Another method for physical delivery of DNA to plants is sonication of target cells. Alternatively, liposome and spheroplast fusion have been used to introduce expression vectors into plants. Electroporation of protoplasts and whole cells and tissues can also be used.

Following transformation of cotton target tissues, expression of the above-described selectable marker genes allows for preferential selection of transformed cells, tissues, and/or plants, using regeneration and selection methods well-known in the art.

The foregoing methods for transformation would typically be used for producing a transgenic variety. The transgenic variety could then be crossed with another (non-transformed or transformed) variety, in order to produce a new transgenic variety. Alternatively, a genetic trait which has been engineered into a particular cotton line using the foregoing transformation techniques could be moved into another line using traditional backcrossing techniques that are well-known in the plant breeding arts. For example, a backcrossing approach could be used to move an engineered trait from a public, non-elite variety into an elite variety, or from a variety containing a foreign gene in its genome into a variety or varieties which do not contain that gene.

Additional Breeding

Cotton plants disclosed herein can also be subject to additional breeding using one or more known methods in the art, e.g., pedigree breeding, recurrent selection, mass selection, and mutation breeding. Pedigree breeding starts with the crossing of two genotypes, such as a cotton variety comprising a staygreen QTL disclosed herein and another cotton variety lacking such a locus. If the two original parents do not provide all the desired characteristics, other sources can be included in the breeding population. In the pedigree method, superior plants are selfed and selected in successive filial generations. In the succeeding filial generations the heterozygous condition gives way to homogeneous varieties as a result of self-pollination and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$, etc. After a sufficient amount of inbreeding, successive filial generations will serve to increase seed of the developed variety. The developed variety may comprise homozygous alleles at about 95% or more of its loci.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, a cotton variety may be crossed with another variety to produce a first generation progeny plant. The first generation progeny plant may then be backcrossed to one of its parent varieties to create a BC1 or BC2. Progeny are selfed and selected so that the newly developed variety has many of the attributes of the recurrent parent and yet several of the desired attributes of the non-recurrent parent. This approach leverages the value and strengths of the recurrent parent for use in new cotton varieties.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic line. A synthetic line is the resultant progeny formed by the intercrossing of several selected varieties.

Mass selection is another useful technique when used in conjunction with molecular marker enhanced selection. In mass selection seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Also, instead of self-pollination, directed pollination could be used as part of the breeding program.

Mutation breeding can also be used to introduce new traits into cotton plants disclosed herein. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, gamma rays (e.g. cobalt 60 or cesium 137), neutrons, (product of nuclear fission by uranium 235 in an atomic reactor), beta radiation (emitted from radioisotopes such as phosphorus 32 or carbon 14), or ultraviolet radiation (from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines). Transposon- or T-DNA-based mutagenesis is also encompassed by the present disclosure. Once a desired trait is observed through mutagenesis the trait may then be incorporated into existing germplasm by traditional breeding techniques.

In an aspect, this disclosure also provides methods for making a substantially homozygous cotton plant by producing or obtaining a seed from a cross of a cotton plant comprising a staygreen allele and another cotton plant and applying double haploid methods to the $F_1$ seed or $F_1$ plant or to any successive filial generation.

Hybrid Production

In an aspect, this disclosure provides hybrid cotton plants and seeds, and their production. The development of a cotton hybrid in a cotton plant breeding program involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrids. During the inbreeding process in cotton, the vigor of the lines decreases. Vigor is restored when two different inbred lines are crossed to produce the hybrid. An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained.

Combining ability of a line, as well as the performance of the line, is a factor in the selection of improved cotton lines that may be used as inbreds. Combining ability refers to a line's contribution as a parent when crossed with other lines to form hybrids. The hybrids formed for the purpose of selecting superior lines are designated test crosses. One way of measuring combining ability is by using breeding values. Breeding values are based on the overall mean of a number of test crosses. This mean is then adjusted to remove environmental effects and it is adjusted for known genetic relationships among the lines.

Hybrid seed production requires inactivation of pollen produced by the female parent. A pollination control system and effective transfer of pollen from one parent to the other offers improved plant breeding and an effective method for producing hybrid cotton seed and plants. For example, a male sterility system can be used to produce cotton hybrids.

Male sterility genes can increase the efficiency with which hybrids are made, in that they eliminate the need to physically emasculate the plant used as a female in a given cross. Where one desires to employ male-sterility systems, it may be beneficial to also utilize one or more male-fertility restorer genes. For example, where cytoplasmic male sterility (CMS) is used, hybrid crossing requires three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent.

The presence of a male-fertility restorer gene results in the production of fully fertile $F_1$ hybrid progeny. If no restorer gene is present in the male parent, male-sterile hybrids are obtained. Examples of male-sterility genes and corresponding restorers which could be employed with the plants of the invention are well known to those of skill in the art of plant breeding. Examples of such genes include CMS-D2-2, CMS-hir, CMS-D8, CMS-D4, and CMS-C1. Fertility can be restored to CMS-D2-2 by the D2 restorer in which the restorer factor(s) was introduced from the genome of *G. harknessii* Brandegee (D2-2). Microsporogenesis in both CMS systems aborts during the premeiotic stage. One dominant restorer gene from the D8 restorer was identified to restore fertility of CMS-D8. The D2 restorer for CMS-D2-2 also restores the fertility of CMS-D8, CMS-hir, and CMS-C1.

Marker Detection

The present disclosure provides markers that are in linkage disequilibrium with at least one STG QTL and can be used to select for STG trait and drought tolerance. Exemplary markers comprise SEQ ID NOs: 1-44 with their representative staygreen alleles are shown in Tables 3 and 6. Markers within approximately 20 cM, 10 cM, 5 cM, 1 cM, 0.5 cM, or less than 0.5 cM of these exemplary markers can also be identified from the known art.

Genetic markers are distinguishable from each other (as well as from the plurality of alleles of any one particular marker) on the basis of polynucleotide length and/or sequence. A large number of cotton molecular markers are known in the art, and are published or available from various sources, such as, US 2014/0255922 A1; Wang et al., A Whole-Genome DNA Marker Map for Cotton Based on the D-Genome Sequence of *Gossypium raimondii* L. G3 3:1759-1767 (2013); Blenda et al., A High Density Consensus Genetic Map of Tetraploid Cotton That Integrates Multiple Component Maps through Molecular Marker Redundancy Check. *PLoS One*, 7(9):e45739 (2012); Yu et al., Genome structure of cotton revealed by a genome-wide SSR genetic map constructed from a $BC_1$ population between *Gossypium hirsutum* and *G. barbadense*. *BMC Genomics*, 12:15 (2011); and Brubaker et al., Comparative genetic mapping of allotetraploid cotton and its diploid progenitors.

*Genome* 42:184-203 (1999); and references therein. In general, any differentially inherited polymorphic trait (including a nucleic acid polymorphism) that segregates among progeny is a potential genetic marker.

As a set, polymorphic markers serve as a useful tool for fingerprinting plants to inform the degree of identity of lines or varieties. These markers can form a basis for determining associations with phenotype and can be used to drive genetic gain. The implementation of marker-assisted selection is dependent on the ability to detect and analyze underlying genetic differences between individuals.

Herein, nucleic acid analysis methods include, but are not limited to, PCR-based detection methods, microarray methods, mass spectrometry-based methods, and/or nucleic acid sequencing methods. In one aspect, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

A method of achieving such amplification employs the polymerase chain reaction (PCR) using primer pairs that are capable of hybridizing to the proximal sequences that define a polymorphism in its double-stranded form. Methods for typing DNA based on mass spectrometry have been disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entireties. However, the compositions and methods of the present disclosure can be used in conjunction with any polymorphism typing method to type polymorphisms in genomic DNA samples. These genomic DNA samples used include but are not limited to genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., Large-scale identification of single-feature polymorphisms in complex genomes. *Genome Research* 13:513-523 (2003); Cui et al., Detecting single-feature polymorphisms using oligonucleotide array and robustified projection pursuit. *Bioinformatics* 21:3852-3858 (2005)). On any one microarray, it is expected there will be a plurality of target sequences, which may represent genes and/or noncoding regions wherein each target sequence is represented by a series of overlapping oligonucleotides, rather than by a single probe. This platform provides for high throughput screening a plurality of polymorphisms. A single-feature polymorphism (SFP) is a polymorphism detected by a single probe in an oligonucleotide array, wherein a feature is a probe in the array. Typing of target sequences by microarray-based methods is disclosed in U.S. Pat. Nos. 6,799,122; 6,913,879; and 6,996,476.

Target nucleic acid sequence can also be detected by probe linking methods as disclosed in U.S. Pat. No. 5,616,464, employing at least one pair of probes having sequences homologous to adjacent portions of the target nucleic acid sequence and having side chains which non-covalently bind to form a stem upon base pairing of the probes to the target nucleic acid sequence. At least one of the side chains has a photoactivatable group which can form a covalent cross-link with the other side chain member of the stem.

Other methods for detecting SNPs and Indels include single base extension (SBE) methods. Examples of SBE methods include, but are not limited, to those disclosed in U.S. Pat. Nos. 6,004,744; 6,013,431; 5,595,890; 5,762,876; and 5,945,283. SBE methods are based on extension of a nucleotide primer that is adjacent to a polymorphism to incorporate a detectable nucleotide residue upon extension of the primer. In an aspect, the SBE method uses four synthetic oligonucleotides. Two of the oligonucleotides serve as PCR primers and are complementary to sequence of the locus of genomic DNA which flanks a region containing the polymorphism to be assayed. Following amplification of the region of the genome containing the polymorphism, the PCR product is mixed with the third and fourth oligonucleotides (called extension primers) which are designed to hybridize to the amplified DNA adjacent to the polymorphism in the presence of DNA polymerase and two differentially labeled dideoxynucleosidetriphosphates. If the polymorphism is present on the template, one of the labeled dideoxynucleosidetriphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR, forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another aspect, the locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), Pac-Bio (Menlo Park, Calif.) and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays, as reviewed by Service, Gene sequencing: the race for the $1000 genome. *Science* 311:1544-46 (2006).

In an alternative aspect, in silico methods can be used to detect the marker loci of interest. For example, the sequence of a nucleic acid comprising the marker locus of interest can be stored in a computer. The desired marker locus sequence or its homolog can be identified using an appropriate nucleic acid search algorithm as provided by, for example, in such readily available programs as BLAST, or even simple word processors.

Any of the aforementioned marker types can be employed in the context of the disclosure to identify chromosome intervals encompassing genetic element that contribute to superior agronomic performance (e.g., cotton drought tolerance).

The markers to be used in the methods of the present disclosure should preferably be diagnostic of origin in order for inferences to be made about subsequent populations. Experience to date suggests that SNP markers may be ideal for mapping because the likelihood that a particular SNP allele is derived from independent origins in the extant populations of a particular species is very low. As such, SNP markers appear to be useful for tracking and assisting introgression of QTL, particularly in the case of genotypes.

Association Mapping

In one aspect, the present disclosure provides chromosome intervals, marker loci, germplasm for conducting genome-wide association mapping for cotton staygreen trait or drought tolerance. Exemplary chromosome intervals and marker loci are provided in Tables 2 and 3. Smaller intervals defined by any two marker loci disclosed in Tables 2 and 3 are also contemplated. Genome-wide association mapping is conducted to find signals of association for various complex traits by surveying genetic variation in the whole genome.

Association mapping relies on chromosomal recombination opportunities over a large number of generations, in the history of a species, which allows the removal of association between a QTL and any marker not tightly linked to it, thus improving the rate of discovery of true association (Jannink and Walsh, *Quantitative Genetics, Genomics and Plant Breeding*, Kang, Ed. CAB International, pp. 59-68 (2002)).

An approach used to link phenotypic variation with genetic loci is marker-trait association (MTA) mapping, also known as linkage disequilibrium (LD) mapping. LD mapping emerged as an important gene mapping tool in early 1990's with the advent of high-throughput genotyping technology, and has been widely used in human genetics to identify genes affecting human diseases. This approach was introduced and began to be adopted in plant gene mapping studies in early 2000's (Flint-Garcia et al., Structure of linkage disequilibrium in plants. *Annual Review of Plant Biology* 54:357-374 (2003)).

LD mapping assumes that the main cause for LD is linkage that binds loci on the same chromosome together in transmission to next generation. However, due to recombination events accumulated over many generations in a natural population, each chromosome has been shuffled deeply, so that the chromosome has been broken into many tiny regions where loci remain transmitted together, but loci from different regions tend to transmit independently as if they were from different chromosomes. Chromosomal regions where loci are bound together in transmission are commonly known as LD blocks (Reich et al., Linkage disequilibrium in the human genome. *Nature* 411:199-204 (2001)). LD mapping identifies genes of interest through genetic markers on the LD blocks where the genes are located. This is done by detecting significant associations between the markers and the traits that the genes affect with a sample of unrelated individuals or a sample of unrelated pedigrees that are genotyped on a selected set of markers covering candidate gene regions or the whole genome, and phenotyped on a set of traits of interest.

Compared with traditional linkage mapping methods that are typically based on artificial biparental segregating populations (e.g., $F_2$, BC, DH, RIL, etc.), LD mapping generally produces better mapping resolution, because of the smaller sizes of LD blocks. In addition, LD mapping is useful in identifying more than two functional alleles at associated markers in a germplasm. Further, LD mapping is efficient for evaluating natural populations.

Identification of QTL

A QTL can act through a single gene mechanism or by a polygenic mechanism. In an aspect, the present disclosure provides an STG QTL interval, where an STG QTL (or multiple STG QTLs) that segregates with an STG trait is contained in the chromosomal interval. As used herein, when a QTL (or multiple QTLs) segregates with the staygreen trait, it is referred to herein as a "staygreen locus" (or "staygreen loci").

In one aspect of this disclosure, the boundaries of an STG QTL interval are drawn to encompass markers that will be linked to or associated with one or more STG QTLs. In other words, an STG QTL interval is drawn such that any marker that lies within that interval (including the terminal markers that define the boundaries of the interval) is genetically linked to or associated with the STG QTL. Each interval comprises at least one STG QTL, and furthermore, may indeed comprise more than one STG QTL. Close proximity of multiple QTLs in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identifying the same QTL or two different QTLs. Regardless, knowledge of how many QTLs are in a particular interval is not necessary to make or practice the claimed subject matter.

The statistical principles of STG QTL identification include penalized regression analysis, ridge regression, single point marker analysis, complex pedigree analysis, Bayesian MCMC, identity-by-descent analysis, interval mapping, composite interval mapping (CIM), and Haseman-Elston regression.

In an aspect, STG QTLs disclosed herein are identified using the MQM (Multiple QTL Model) approach. This approach is implemented in three main steps: 1) missing genotypes are imputed and assigned a probability used as a weight in later analysis; 2) co-factors are selected genome-wide by multiple regression and backward elimination; and 3) QTL scan across the genome using the co-factors selected in step 2 (Arends et al., r/QTL: high throughput multiple QTL mapping *Bioinformatics,* 26:2990-2992 (2010)). QTL empirical significance threshold is estimated after 1000 permutations. The putative position of the QTL is estimated at the point of maximum LOD score. The STG QTL support interval is estimated using the Bayesian credible interval method. The phenotypic variance explained by an STG QTL is estimated as the square of the partial correlation coefficient ($R^2$) with the staygreen rating, adjusted for co-factors.

In an aspect, the present disclosure also provides the mapping of additional SNP markers associated with or linked to one or more STG QTLs disclosed herein. SNP markers are ideal for mapping because the likelihood that a particular SNP allele is derived from independent origins in the extant populations of a particular species is very low. As such, SNP markers are useful for tracking and assisting introgression of STG QTLs, particularly in the case of haplotypes. In an aspect, a SNP marker is selected for mapping an STG QTL based on the marker's genetic map position. In another aspect, a SNP marker is selected for mapping an STG QTL based on the marker's physical map position.

The genetic linkage of additional marker molecules can be established by a gene mapping model such as, without limitation, the flanking marker model reported by Lander and Botstein, (Lander and Botstein, Mapping Mendelian Factors Underlying Quantitative Traits Using RFLP Linkage Maps. *Genetics,* 121:185-199 (1989)), and the interval mapping, based on maximum likelihood methods described by Lander and Botstein (supra), and implemented in the software package MAPMAKER/QTL (Lincoln and Lander, *Mapping Genes Controlling Quantitative Traits Using MAPMAKER/QTL*, Whitehead Institute for Biomedical Research, Massachusetts, (1990). Additional software includes Qgene, Version 2.23 (1996), Department of Plant Breeding and Biometry, 266 Emerson Hall, Cornell University, Ithaca, N.Y., the manual of which is herein incorporated by reference in its entirety).

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$ (MLE for the presence of a QTL/MLE given no linked QTL). The LOD score essentially indicates how much more likely the data are to have arisen assuming the presence of a QTL versus in its absence. The LOD threshold value for avoiding a false positive with a given confidence, say 95%, depends on the number of markers and the length of the genome. Graphs indicating LOD thresholds are set forth in Lander and Botstein, (Lander and Botstein, Mapping Mendelian Factors Underlying Quantitative Traits Using RFLP Linkage Maps. *Genetics,* 121:185-199 (1989), and further described by Arús and Moreno-González, *Plant Breeding*, Hayward, Bosemark, Romagosa (eds.) Chapman & Hall, London, pp. 314-331 (1993).

Additional models can be used. Many modifications and alternative approaches to interval mapping have been reported, including the use of non-parametric methods (Kruglyak and Lander, A Nonparametric Approach for Mapping Quantitative Trait Loci. *Genetics,* 139:1421-1428 (1995), the entirety of which is herein incorporated by reference). Multiple regression methods or models can be also be used, in which the trait is regressed on a large number of markers (Jansen, *Biometrics in Plant Breed*, van Oij en, Jansen (eds.) Proceedings of the Ninth Meeting of the Eucarpia Section Biometrics in Plant Breeding, The Netherlands, pp. 116-124 (1994); Weber and Wricke, *Advances in Plant Breeding*, Blackwell, Berlin, 16 (1994)). Procedures combining interval mapping with regression analysis, whereby the phenotype is regressed onto a single putative QTL at a given marker interval, and at the same time onto a number of markers that serve as 'cofactors,' have been reported by Jansen and Stam, High Resolution of Quantitative Traits Into Multiple Loci via Interval Mapping. *Genetics,* 136:1447-1455 (1994) and Zeng, Precision Mapping of Quantitative Trait Loci. *Genetics,* 136:1457-1468 (1994). Generally, the use of cofactors reduces the bias and sampling error of the estimated QTL positions (Utz and Melchinger, *Biometrics in Plant Breeding*, van Oij en, Jansen (eds.) Proceedings of the Ninth Meeting of the Eucarpia Section Biometrics in Plant Breeding, The Netherlands, pp. 195-204 (1994)), thereby improving the precision and efficiency of QTL mapping (Zeng, Precision Mapping of Quantitative Trait Loci. *Genetics,* 136:1457-1468 (1994)). These models can be extended to multi-environment experiments to analyze genotype-environment interactions (Jansen et al., Genotype-by-environment interaction in genetic mapping of multiple quantitative trait loci. *Theoretical and Applied Genetics* 91:33-37 (1995)).

In an aspect, the disclosure provides chromosomal intervals comprising QTL associated with staygreen trait. In one aspect, the chromosome intervals of the disclosure are characterized by genomic regions including and flanked by any two of marker loci SEQ ID NOs: 1 to 7. In another aspect, the chromosome intervals of the disclosure are characterized by genomic regions including and flanked by any two of marker loci SEQ ID NOs: 8 to 17.

The disclosure also provides multiple markers linked to or associated with an STG QTL, for example, the markers having the sequence selected from SEQ ID NOs: 1-44. The disclosure therefore provides plants comprising a nucleic acid molecule selected from the group consisting of SEQ ID NOs: 1-44, fragments thereof, or complements thereof. The present disclosure further provides a plant comprising alleles of the chromosome interval linked to or associated with STG trait and drought tolerance or fragments and complements thereof as well as any plant comprising any combination of one or more staygreen alleles of marker loci selected from the group consisting of SEQ ID NOs: 1-44. Plants provided by the disclosure may be homozygous or heterozygous for such alleles.

The compositions and methods of the present disclosure can be utilized to guide MAS or breeding cotton varieties with a desired complement (set) of allelic forms of chromosome intervals associated with superior agronomic performance (e.g. drought tolerance). Any of the disclosed marker alleles can be introduced into a cotton line via introgression, by traditional breeding (or introduced via transformation, or both) to yield a cotton plant with superior agronomic performance. The number of alleles associated with STG trait and drought tolerance that can be introduced or be present in a cotton plant of the present disclosure ranges from 1 to the number of alleles disclosed herein, each integer of which is incorporated herein as if explicitly recited.

MAS using additional markers flanking either side of the DNA locus provide further efficiency because an unlikely double recombination event would be needed to simultaneously break linkage between the locus and both markers. Moreover, using markers tightly flanking a locus, one skilled in the art of MAS can reduce linkage drag by more accurately selecting individuals that have less of the potentially deleterious donor parent DNA. Any marker linked to or among the chromosome intervals described herein can thus find use within the scope of this disclosure.

These marker loci can be introgressed into any desired genomic background, germplasm, plant, line, variety, etc., as part of an overall MAS breeding program designed to enhance STG trait and drought tolerance. The disclosure also provides QTL intervals that can be used in MAS to select plants that demonstrate drought tolerance. Similarly, QTL intervals can also be used to counter-select plants that are lacking drought tolerance. By identifying plants lacking a desired marker locus, plants lacking drought tolerance can be identified and selected or eliminated from subsequent crosses.

The present disclosure also extends to a method of making a progeny cotton plant and the resulting progeny cotton plants. In one aspect, the method comprises crossing a first parent cotton plant with a second cotton plant and growing the cotton plant parent under plant growth conditions to yield cotton plant progeny. Methods of crossing and growing cotton plants are well within the ability of those of ordinary skill in the art. Such cotton plant progeny can be assayed for alleles associated with drought tolerance as disclosed herein and, thereby, the desired progeny selected. Such progeny plants or seed thereof can be sold commercially for cotton production, used for food, processed to obtain a desired constituent of the cotton, or further utilized in subsequent rounds of breeding. At least one of the first or second cotton plants may be a cotton plant of the present disclosure in that it comprises at least one of the allelic forms of the markers of the present disclosure, such that the progeny are capable of inheriting the allele.

By providing the positions in the cotton genome of QTL intervals and the associated markers within those intervals, the disclosure also allows one skilled in the art to identify and use other markers within the intervals disclosed herein or linked to or associated with the intervals disclosed herein. Having identified such markers, these intervals can be readily identified from public linkage maps.

Closely linked markers flanking the locus of interest that have alleles in linkage disequilibrium (LD) with a staygreen allele at that locus may be effectively used to select for progeny plants with staygreen trait or drought tolerance. Thus, the markers described herein, such as those listed in Tables 3 and 6, as well as other markers genetically linked to or associated with the same chromosome interval, may be used to select for cotton plants with drought tolerance. Often, a set of these markers will be used, (e.g., 2 or more, 3 or more, 4 or more, 5 or more) in the flanking regions of the locus. Optionally, as described above, a marker flanking or within the actual locus may also be used. The parents and their progeny may be screened for these sets of markers, and the markers that are polymorphic between the two parents used for selection. In an introgression program, this allows for selection of the gene or locus genotype at the more proximal polymorphic markers and selection for the recurrent parent genotype at the more distal polymorphic markers.

The choice of markers actually used to practice the disclosure is not limited and can be any marker that is genetically linked to or associated with the QTL intervals as described in Tables 2 or 6, including markers within approximately 20 cM, 10 cM, 5 cM, 1 cM, 0.5 cM, or less than 0.5 cM of the intervals provided herein. Examples include, but are not limited to, any marker selected from SEQ ID NOs: 1-44. Furthermore, since there are many different types of marker detection assays known in the art, it is not intended that the type of marker detection assay used to practice this disclosure be limited in any way.

Marker Assisted Selection (MAS) Breeding

Marker loci and their staygreen alleles provided herein can be used in MAS breeding of drought tolerance. The more tightly linked a marker is with a DNA locus influencing a phenotype (e.g., STG or drought tolerance), the more reliable the marker is in MAS, as the likelihood of a recombination event unlinking the marker and the locus decreases. Markers containing the causal mutation for a trait, or that are within the coding sequence of a causative gene, are ideal as no recombination is expected between them and the sequence of DNA responsible for the phenotype. However, markers do not need to contain or correspond to causal mutations in order to be effective in MAS. In fact, most MAS breeding only uses markers linked to or associated with a causal mutation.

Developing molecular markers in crop species can increase efficiency in plant breeding through MAS. Genetic markers are used to identify plants that contain a desired genotype at one or more loci, and that are expected to transfer the desired genotype, along with a desired phenotype to their progeny. Genetic markers can be used to identify plants containing a desired genotype at one locus, or at several unlinked or linked loci (e.g., a haplotype), and that would be expected to transfer the desired genotype, along with a desired phenotype to their progeny. The present disclosure provides the means to identify plants that exhibit drought tolerance by identifying chromosomal intervals and genetic markers associated with drought tolerance.

In general, MAS uses polymorphic markers that have been identified as having a significant likelihood of co-segregation with a desired trait. Such markers are presumed to map near a gene or genes that give the plant its desired phenotype, and are considered indicators for the desired trait.

Identification of plants or germplasm that include a marker locus or marker loci linked to a desired trait or traits provides a basis for performing MAS. Plants that comprise favorable markers or favorable alleles are selected for, while plants that comprise markers or alleles that are negatively correlated with the desired trait can be selected against. Desired markers and/or alleles can be introgressed into plants having a desired (e.g., elite or exotic) genetic background to produce an introgressed plant or germplasm having the desired trait. In an aspect, it is contemplated that a plurality of markers for desired traits are sequentially or simultaneous selected and/or introgressed. The combinations of markers that are selected for in a single plant is not limited, and can include any combination of markers disclosed herein or any marker linked to the markers disclosed herein, or any markers located within the QTL intervals defined herein.

In an aspect, a first cotton plant or germplasm exhibiting a desired trait (the donor, e.g., a staygreen cotton) can be crossed with a second cotton plant or germplasm (the recipient, e.g., an elite or exotic cotton, depending on characteristics that are desired in the progeny) to create an introgressed cotton plant or germplasm as part of a breeding program. In an aspect, the recipient plant can also contain one or more loci associated with one or more desired traits, which can be qualitative or quantitative trait loci. In another aspect, the recipient plant can contain a transgene.

In an aspect, the recipient cotton plant or germplasm will typically lack desired traits as compared to the first cotton plant or germplasm, while the introgressed cotton plant or germplasm will display improved traits as compared to the second plant or germplasm. An introgressed cotton plant or germplasm produced by these methods are also a feature of this disclosure.

MAS is a powerful shortcut to select for desired phenotypes and for introgressing desired traits into cultivars (e.g., introgressing desired traits into elite lines). MAS is easily adapted to high throughput molecular analysis methods that can quickly screen large numbers of plant or germplasm genetic material for the markers of interest and is much more cost effective than cultivating and observing plants for visible traits.

When a population is segregating for multiple loci affecting one of multiple traits, e.g., multiple loci involved in drought tolerance, the efficiency of MAS compared to phenotypic screening becomes even greater, because all of the loci can be evaluated together from a single sample of DNA.

Introgression of STG QTLs Using MAS

The instant disclosure provides methods and markers for introgressing an STG QTL disclosed herein into a new cotton variety using MAS.

Multiple methods are available to achieve the introgression. For example, introgression of a desired allele at a specified locus can be transmitted to at least one progeny via a cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background.

The introgression of one or more desired loci from a donor line into another line is achieved via repeated backcrossing to a recurrent parent accompanied by selection to retain one or more loci from the donor parent. Markers associated with drought tolerance are assayed in progeny and those progeny with one or more desired markers are selected for advancement. In another aspect, one or more markers can be assayed in the progeny to select for plants with the genotype of the agronomically elite parent.

It is generally anticipated that trait introgression activities will require more than one generation, wherein progeny are crossed to the recurrent (agronomically elite) parent or selfed. Selections are made based on the presence of one or more markers linked to drought tolerance and can also be made based on the recurrent parent genotype, wherein screening is performed on a genetic marker and/or phenotype basis. In another aspect, markers of this disclosure can be used in conjunction with other markers, ideally at least one on each chromosome of the cotton genome, to track the introgression of drought tolerance into elite germplasm. In another aspect, QTL intervals associated with drought tolerance will be useful in conjunction with SNP molecular markers of the present disclosure to combine quantitative and qualitative drought tolerance in the same plant. It is within the scope of this disclosure to utilize the methods and compositions for trait integration of drought tolerance. It is contemplated by the inventors that the present disclosure will be useful for developing commercial varieties with drought tolerance and other agronomically elite phenotypes.

The following are exemplary embodiments of the present disclosure.

Embodiment 1

A method of creating a population of cotton plants or seeds, the method comprising the steps of:

a. genotyping a first population of cotton plants or seeds at a marker locus associated with a staygreen (STG) quantitative trait locus (QTL) selected from the group consisting of STG QTLs 1 to 7;

b. selecting from the first population one or more cotton plants or seeds comprising an STG allele of the marker locus; and c. producing from the selected one or more cotton plants or seeds a second population of cotton plants or seeds comprising the STG QTL.

Embodiment 2

The method of Embodiment 1, wherein the STG QTL 1 is located in a chromosomal interval flanked by any two of marker loci selected from the group consisting of SEQ ID NOs: 1 to 7.

Embodiment 3

The method of Embodiment 1, wherein the STG QTL 2 is located in a chromosomal interval flanked by any two of marker loci selected from the group consisting of SEQ ID NOs: 8 to 17.

Embodiment 4

The method of Embodiment 1, wherein the STG QTL 3 is located in a chromosomal interval flanked by any two of marker loci selected from the group consisting of SEQ ID NOs: 18 to 21.

Embodiment 5

The method of Embodiment 1, wherein the STG QTL 4 is located in a chromosomal interval flanked by any two of marker loci selected from the group consisting of SEQ ID NOs: 22 to 28.

Embodiment 6

The method of Embodiment 1, wherein the STG QTL 5 is located in a chromosomal interval flanked by any two of marker loci selected from the group consisting of SEQ ID NOs: 29 to 32.

Embodiment 7

The method of Embodiment 1, wherein the STG QTL 6 is located in a chromosomal interval flanked by any two of marker loci selected from the group consisting of SEQ ID NOs: 33 to 40.

Embodiment 8

The method of Embodiment 1, wherein the STG QTL 7 is located in a chromosomal interval flanked by any two of marker loci selected from the group consisting of SEQ ID NOs: 41 to 44.

Embodiment 9

The method of Embodiment 1, wherein the marker locus is located in a chromosomal interval flanked by any two of marker loci selected from the group consisting of SEQ ID NOs: 1 to 7.

Embodiment 10

The method of Embodiment 1, wherein the marker locus is located in a chromosomal interval flanked by any two of marker loci selected from the group consisting of SEQ ID NOs: 8 to 17.

Embodiment 11

The method of Embodiment 1, wherein the marker locus is located in a chromosomal interval flanked by any two of marker loci selected from the group consisting of SEQ ID NOs: 18 to 21.

Embodiment 12

The method of Embodiment 1, wherein the marker locus is located in a chromosomal interval flanked by any two of marker loci selected from the group consisting of SEQ ID NOs: 22 to 28.

Embodiment 13

The method of Embodiment 1, wherein the marker locus is located in a chromosomal interval flanked by any two of marker loci selected from the group consisting of SEQ ID NOs: 29 to 32.

Embodiment 14

The method of Embodiment 1, wherein the marker locus is located in a chromosomal interval flanked by any two of marker loci selected from the group consisting of SEQ ID NOs: 33 to 40.

Embodiment 15

The method of Embodiment 1, wherein the marker locus is located in a chromosomal interval flanked by any two of marker loci selected from the group consisting of SEQ ID NOs: 41 to 44.

Embodiment 16

The method of Embodiment 1, wherein the marker locus is within about 20 cM, 15 cM, 10 cM, 5 cM, 4 cM, 3 cM, 2 cM, 1 cM, 0.5 cM, or less than 0.5 cM of any one of marker loci SEQ ID NOs: 1 to 44.

Embodiment 17

The method of Embodiment 1, wherein the STG QTL provides post-anthesis drought or heat tolerance.

Embodiment 18

The method of Embodiment 1, wherein the STG QTL confer no yield penalty under water-sufficient conditions.

Embodiment 19

The method of Embodiment 1, wherein the STG QTL delays the onset of senescence under water-limited conditions.

Embodiment 20

The method of Embodiment 1, wherein the STG QTL delays the rate of senescence under water-limited conditions.

Embodiment 21

The method of Embodiment 1, wherein cotton plants comprising the STG QTL comprise greener leaves compared to cotton plants without the STG QTL under similar water-sufficient conditions.

Embodiment 22

The method of Embodiment 1, wherein the seed or fiber yield of cotton plants comprising the STG QTL is about 3% or more, 5% or more, 8% or more, 10% or more, 12% or more, 15% or more, 17% or more, 20% or more, 25% or more, or 30% or more higher than the seed or fiber yield of cotton plants without the STG QTL under water-limited conditions.

Embodiment 23

The method of Embodiment 1, wherein the seed or fiber yield of cotton plants comprising the STG QTL is between 3% and 4%, between 4% and 5%, between 5% and 6%, between 6% and 7%, between 7% and 8%, between 8% and 9%, or between 9% and 10% higher than the seed or fiber yield of cotton plants without the STG QTL under water-limited conditions.

Embodiment 24

The method of Embodiment 1, wherein the seed or fiber yield of cotton plants comprising the STG QTL is between 3% and 10%, between 4% and 10%, between 5% and 10%, between 6% and 10%, between 7% and 10%, or between 8% and 10% higher than the seed or fiber yield of cotton plants without the STG QTL under water-limited conditions.

Embodiment 25

The method of Embodiment 1, wherein the step (a) comprises a marker assay.

Embodiment 26

The method of Embodiment 1, wherein the step (a) comprises detecting a haplotype.

Embodiment 27

The method of Embodiment 26, wherein the haplotype comprises STG alleles of any two of marker loci SEQ ID NOs: 1 to 7.

Embodiment 28

The method of Embodiment 26, wherein the haplotype comprises STG alleles of any two of marker loci SEQ ID NOs: 8 to 17.

Embodiment 29

The method of Embodiment 26, wherein the haplotype comprises STG alleles of any two of marker loci SEQ ID NOs: 18 to 21.

Embodiment 30

The method of Embodiment 26, wherein the haplotype comprises STG alleles of any two of marker loci SEQ ID NOs: 22 to 28.

Embodiment 31

The method of Embodiment 26, wherein the haplotype comprises STG alleles of any two of marker loci SEQ ID NOs: 29 to 32.

Embodiment 32

The method of Embodiment 26, wherein the haplotype comprises STG alleles of any two of marker loci SEQ ID NOs: 33 to 40.

Embodiment 33

The method of Embodiment 26, wherein the haplotype comprises STG alleles of any two of marker loci SEQ ID NOs: 41 to 44.

Embodiment 34

The method of Embodiment 1, wherein the step (a) comprises assaying a SNP marker.

Embodiment 35

The method of Embodiment 1, wherein the step (a) comprises the use of an oligonucleotide probe.

Embodiment 36

The method of Embodiment 35, wherein the oligonucleotide probe is adjacent to a polymorphic nucleotide position in the marker locus.

Embodiment 37

A method of introgressing an STG QTL, the method comprising:

a. crossing a first cotton plant comprising an STG QTL selected from the group consisting of STG QTLs 1 to 7, with a second cotton plant of a different genotype to produce one or more progeny plants or seeds; and
b. assaying the one or more progeny plants or seeds at a marker locus associated with the STG QTL; and
c. selecting a progeny plant or seed comprising the STG QTL.

Embodiment 38

The method of Embodiment 37, wherein the STG QTL 1 is located in a chromosomal interval flanked by any two of marker loci selected from the group consisting of SEQ ID NOs: 1 to 7.

Embodiment 39

The method of Embodiment 37, wherein the STG QTL 2 is located in a chromosomal interval flanked by any two of marker loci selected from the group consisting of SEQ ID NOs: 8 to 17.

Embodiment 40

The method of Embodiment 37, wherein the STG QTL 3 is located in a chromosomal interval flanked by any two of marker loci selected from the group consisting of SEQ ID NOs: 18 to 21.

Embodiment 41

The method of Embodiment 37, wherein the STG QTL 4 is located in a chromosomal interval flanked by any two of marker loci selected from the group consisting of SEQ ID NOs: 22 to 28.

Embodiment 42

The method of Embodiment 37, wherein the STG QTL 5 is located in a chromosomal interval flanked by any two of marker loci selected from the group consisting of SEQ ID NOs: 29 to 32.

Embodiment 43

The method of Embodiment 37, wherein the STG QTL 6 is located in a chromosomal interval flanked by any two of marker loci selected from the group consisting of SEQ ID NOs: 33 to 40.

Embodiment 44

The method of Embodiment 37, wherein the STG QTL 7 is located in a chromosomal interval flanked by any two of marker loci selected from the group consisting of SEQ ID NOs: 41 to 44.

Embodiment 45

The method of Embodiment 37, wherein the marker locus is located in a chromosomal interval flanked by any two of marker loci selected from the group consisting of SEQ ID NOs: 1 to 7.

Embodiment 46

The method of Embodiment 37, wherein the marker locus is located in a chromosomal interval flanked by any two of marker loci selected from the group consisting of SEQ ID NOs: 8 to 17.

Embodiment 47

The Embodiment of claim 37, wherein the marker locus is located in a chromosomal interval flanked by any two of marker loci selected from the group consisting of SEQ ID NOs: 18 to 21.

Embodiment 48

The method of Embodiment 37, wherein the marker locus is located in a chromosomal interval flanked by any two of marker loci selected from the group consisting of SEQ ID NOs: 22 to 28.

Embodiment 49

The method of Embodiment 37, wherein the marker locus is located in a chromosomal interval flanked by any two of marker loci selected from the group consisting of SEQ ID NOs: 29 to 32.

Embodiment 50

The method of Embodiment 37, wherein the marker locus is located in a chromosomal interval flanked by any two of marker loci selected from the group consisting of SEQ ID NOs: 33 to 40.

Embodiment 51

The method of Embodiment 37, wherein the marker locus is located in a chromosomal interval flanked by any two of marker loci selected from the group consisting of SEQ ID NOs: 41 to 44.

Embodiment 52

The method of Embodiment 37, wherein the marker locus is within about 20 cM, 15 cM, 10 cM, 5 cM, 4 cM, 3 cM, 2 cM, 1 cM, 0.5 cM, or less than 0.5 cM of any one of marker loci SEQ ID NOs: 1 to 44

Embodiment 53

The method of Embodiment 37, further comprising:

d. crossing the selected progeny plant with itself or the second plant to produce one or more further progeny plants or seeds; and e. selecting a further progeny plant or seed comprising the STG QTL.

Embodiment 54

The method of Embodiment 53, wherein step (e) of selecting comprises marker-assisted selection.

Embodiment 55

The method of Embodiment 54, wherein the marker-assisted selection comprises selecting a marker within about 20 cM, 15 cM, 10 cM, 5 cM, 4 cM, 3 cM, 2 cM, 1 cM, 0.5 cM, or less than 0.5 cM of any one of STG QTLs 1 to 7.

Embodiment 56

The method of Embodiment 53, wherein the production of the one or more further progeny plants or seeds comprises backcrossing.

Embodiment 57

The method of Embodiment 56, wherein the backcrossing comprises 2 to 7 generations of backcrosses.

Embodiment 58

The method of Embodiment 37, wherein the first cotton plant is an inbred or a hybrid.

Embodiment 59

The method of Embodiment 37, wherein the second cotton plant is an agronomically elite cotton plant.

Embodiment 60

The method of Embodiment 37, wherein the STG QTL has no impact in the selected progeny plant over at least one or more, two or more, three or more, four or more, five or more, six or more, or seven or more traits at maturity selected from the group consisting of plant height, micronaire, bolls open percentage, fiber elongation percentage, fiber maturity ratio, short fiber content, fiber length, fiber strength, uniformity index, lint percentage, and stringout rating, under either water-limited conditions or water-sufficient conditions.

Embodiment 61

A method for selecting a cotton plant or seed, the method comprising:

a. detecting in a population of cotton plants or seeds a cotton plant or seed comprising an STG allele of a marker locus associated with an STG QTL selected from the group consisting of STG QTLs 1 to 7; and b. selecting the cotton plant or seed comprising the STG allele.

Embodiment 62

The method of Embodiment 61, wherein the marker locus is located in a chromosomal interval flanked by any two of marker loci selected from the group consisting of SEQ ID NOs: 1 to 7.

Embodiment 63

The method of Embodiment 61, wherein the marker locus is located in a chromosomal interval flanked by any two of marker loci selected from the group consisting of SEQ ID NOs: 8 to 17.

Embodiment 64

The method of Embodiment 61, wherein the marker locus is located in a chromosomal interval flanked by any two of marker loci selected from the group consisting of SEQ ID NOs: 18 to 21.

Embodiment 65

The method of Embodiment 61, wherein the marker locus is located in a chromosomal interval flanked by any two of marker loci selected from the group consisting of SEQ ID NOs: 22 to 28.

Embodiment 66

The method of Embodiment 61, wherein the marker locus is located in a chromosomal interval flanked by any two of marker loci selected from the group consisting of SEQ ID NOs: 29 to 32.

Embodiment 67

The method of Embodiment 61, wherein the marker locus is located in a chromosomal interval flanked by any two of marker loci selected from the group consisting of SEQ ID NOs: 33 to 40.

Embodiment 68

The method of Embodiment 61, wherein the marker locus is located in a chromosomal interval flanked by any two of marker loci selected from the group consisting of SEQ ID NOs: 41 to 44.

Embodiment 69

The method of Embodiment 61, wherein the marker locus is within about 20 cM, 15 cM, 10 cM, 5 cM, 4 cM, 3 cM, 2 cM, 1 cM, 0.5 cM, or less than 0.5 cM of any one of marker loci SEQ ID NOs: 1 to 44.

Embodiment 70

The method of Embodiment 61, wherein the marker locus is within about 20 cM, 15 cM, 10 cM, 5 cM, 4 cM, 3 cM, 2 cM, 1 cM, 0.5 cM, or less than 0.5 cM of any one of STG QTLs 1 to 7.

Embodiment 71

The method of Embodiment 61, wherein the step (a) comprises a marker assay.

Embodiment 72

A method for evaluating a collection of cotton germplasm, the method comprising:

a. obtaining a collection of cotton germplasm;

b. isolating nucleic acids from each germplasm;

c. assaying the nucleic acids for one or more markers linked to an STG QTL selected from the group consisting of STG QTLs 1 to 7;

d. selecting germplasm having an STG QTL based on the marker assay.

Embodiment 73

The method of Embodiment 72, wherein the one or more markers are within about 20 cM, 15 cM, 10 cM, 5 cM, 4 cM, 3 cM, 2 cM, 1 cM, 0.5 cM, or less than 0.5 cM of any one of marker loci SEQ ID NOs: 1 to 44

Embodiment 74

The method of Embodiment 72, wherein the method further comprises confirming that the selected germplasm has post-anthesis drought or heat tolerance.

Embodiment 75

A method comprising providing a set of cotton seeds comprising one or more STG QTLs selected from the group consisting of STG QTLs 1 to 7, to a person desirous of planting the set of cotton seeds in a field plot prone to drought or heat stress.

Embodiment 76

The method of Embodiment 75, wherein the one or more STG QTLs provide post-anthesis drought or heat tolerance.

Embodiment 77

The method of Embodiment 75, wherein the set of cotton seeds comprising the one or more STG QTLs provide higher yield of seed, fiber, or both compared to cotton seeds not comprising the one or more STG QTLs when grown under water limited conditions.

Embodiment 78

A method of growing a population of cotton plants in a field plot prone to drought or heat stress, the method comprising planting a population of cotton seeds comprising one or more introgressed STG QTLs selected from the group consisting of STG QTLs 1 to 7 in the field plot prone to drought or heat stress.

Embodiment 79

The method of Embodiment 78, wherein the cotton seeds are elite cotton seeds.

Embodiment 80

The method of Embodiment 78, further comprising obtaining the population of cotton seeds from a seed distributor.

Embodiment 81

The method of Embodiment 78, wherein the drought or heat stress starts after cotton plants grown from the cotton seeds flower.

Embodiment 82

The method of Embodiment 78, wherein the introgressed one or more STG QTLs provide post-anthesis drought or heat tolerance.

Embodiment 83

The method of Embodiment 78, wherein the population of cotton seeds provide higher yield of seed, fiber, or both compared to cotton seeds not comprising the one or more introgressed STG QTLs when grown in the field plot.

Embodiment 84

A method of reducing the cost of watering cotton plants, the method comprising:

a. growing a population of cotton plants comprising one or more introgressed STG QTLs selected from the group consisting of STG QTLs 1 to 7;

b. reducing the amount of water supplied to the population of cotton plants after the cotton plants start flowering.

Embodiment 85

The method of Embodiment 84, wherein the method further comprises adjusting defoliation treatment to increase defoliation rate and prepare for harvest.

Embodiment 86

The method of Embodiment 84, wherein the reduction of watering has no significant impact over the yield of seed, fiber, or both from the population of cotton plants.

Embodiment 87

The method of Embodiment 84, wherein the step (b) comprises reducing watering frequency.

Embodiment 88

The method of Embodiment 84, wherein the step (b) comprises reducing the amount of water in each watering.

Embodiment 89

A cotton plant or seed comprising a staygreen trait and one or more, two or more, three or more, four or more, five or more, six or more introgressed STG QTLs selected from the group consisting of STG QTLs 1 to 7.

Embodiment 90

The cotton plant or seed of Embodiment 89, wherein the cotton plant or seed is transgenic.

Embodiment 91

The cotton plant or seed of Embodiment 89, wherein the introgressed STG QTLs are also present in or originate from one or more cotton germplasm selected from the group consisting of STG-001 and STG-002 having an ATCC deposit number of PTA-122486 and PTA-122487, respectively.

Embodiment 92

The cotton plant or seed of Embodiment 89, wherein the STG QTL 1 is located in a chromosomal interval flanked by any two of marker loci selected from the group consisting of SEQ ID NOs: 1 to 7.

Embodiment 93

The cotton plant or seed of Embodiment 89, wherein the STG QTL 2 is located in a chromosomal interval flanked by any two of marker loci selected from the group consisting of SEQ ID NOs: 8 to 17.

Embodiment 94

The method of Embodiment 89, wherein the STG QTL 3 is located in a chromosomal interval flanked by any two of marker loci selected from the group consisting of SEQ ID NOs: 18 to 21.

Embodiment 95

The method of Embodiment 89, wherein the STG QTL 4 is located in a chromosomal interval flanked by any two of marker loci selected from the group consisting of SEQ ID NOs: 22 to 28.

Embodiment 96

The method of Embodiment 89, wherein the STG QTL 5 is located in a chromosomal interval flanked by any two of marker loci selected from the group consisting of SEQ ID NOs: 29 to 32.

Embodiment 97

The method of Embodiment 89, wherein the STG QTL 6 is located in a chromosomal interval flanked by any two of marker loci selected from the group consisting of SEQ ID NOs: 33 to 40.

Embodiment 98

The method of Embodiment 89, wherein the STG QTL 7 is located in a chromosomal interval flanked by any two of marker loci selected from the group consisting of SEQ ID NOs: 41 to 44.

Embodiment 99

The cotton plant or seed of Embodiment 89, wherein the cotton plant or seed is non-transgenic.

Embodiment 100

The cotton plant or seed of Embodiment 89, wherein the cotton plant or seed is homozygous at the one or more introgressed STG QTLs.

Embodiment 101

The cotton plant or seed of Embodiment 89, wherein the cotton plant or seed is a hybrid.

Embodiment 102

The cotton plant or seed of Embodiment 89, wherein the cotton plant or seed is an inbred.

Embodiment 103

The cotton plant or seed of Embodiment 89, wherein the cotton plant or seed has post-anthesis drought or heat tolerance.

Embodiment 104

The cotton plant or seed of Embodiment 89, wherein cotton plant or seed is from an elite cotton variety.

Embodiment 105

The cotton plant or seed of Embodiment 89, wherein the introgressed STG QTLs have no impact over at least one or more, two or more, three or more, four or more, five or more, six or more, or seven or more cotton traits at maturity selected from the group consisting of plant height, micronaire, bolls open percentage, fiber elongation percentage, fiber maturity ratio, short fiber content, fiber length, fiber strength, uniformity index, lint percentage, and stringout rating, under either water-limited conditions or water-sufficient conditions.

Embodiment 106

The cotton plant or seed of Embodiment 89, wherein the seed or fiber yield of the cotton plant or seed is about 3%, 5%, 8%, 10%, 12%, 15%, 17%, 20%, 22%, 25%, 30%, 35%, 40%, 45%, 50%, 55%, 60%, 65%, 70% or more higher than the seed or fiber yield of a cotton plant without the introgressed STG QTLs under water-limited conditions.

Embodiment 107

A cotton plant or seed comprising an STG trait and an introgressed STG QTL, wherein the STG QTL is within about 20 cM, 15 cM, 10 cM, 5 cM, 4 cM, 3 cM, 2 cM, 1 cM, 0.5 cM, or less than 0.5 cM of any one of marker loci SEQ ID NOs: 1 to 44.

Embodiment 108

The cotton plant or seed of Embodiment 107, wherein the STG QTL provides post-anthesis drought or heat tolerance.

Embodiment 109

The cotton plant or seed of Embodiment 107, wherein the STG QTL confers no yield penalty under water-sufficient conditions.

Embodiment 110

The cotton plant or seed of Embodiment 107, wherein the STG QTL delays the onset of senescence under water-limited conditions.

Embodiment 111

The cotton plant or seed of Embodiment 107, wherein the STG QTL reduces the rate of senescence under water-limited conditions.

Embodiment 112

The cotton plant or seed of Embodiment 107, wherein the cotton plant or a cotton plant grown from the cotton seed exhibits no wilting under water-limited conditions.

Embodiment 113

The cotton plant or seed of Embodiment 107, wherein the cotton plant or a cotton plant grown from the cotton seed comprises greener leaves compared to a cotton plant without the STG QTL under similar water-sufficient conditions.

Embodiment 114

The cotton plant or seed of Embodiment 107, wherein the cotton plant or a cotton plant grown from the cotton seed comprises seed or fiber yield of about 3%, 5%, 8%, 10%, 12%, 15%, 17%, 20%, 22%, 25%, 30%, 35%, 40%, 45%, 50%, 55%, 60%, 65%, 70% or more higher than the seed or fiber yield of a cotton plant without the STG QTL under water-limited conditions.

EXAMPLES

Example 1. Identification of a Staygreen (STG) Trait in Cotton and Development of Bi-Parental Mapping Populations A cotton staygreen trait is first identified in Monsanto's cotton breeding program. Cotton plants with this trait have thick, succulent, and dark-green colored leaves. The canopy of staygreen cotton plants is bushier than normal non-staygreen plants. When exposed to heat or water stress, leaves of staygreen plants stay turgid much longer and are relatively slower to wilt than non-staygreen plants. Canopy temperature of staygreen plants is lower than that of non-staygreen plants. Staygreen cotton plants tend to have delayed senescence, early and late season cold tolerance, and better early-season vigor than non-staygreen plants. A bi-parental mapping approach is used to understand the genetic basis of the cotton staygreen trait.

Two bi-parental mapping populations are developed by crossing staygreen lines STG-001 and STG-002 with the same non-staygreen line HS200. HS200 is used as female parent in both crosses. A total of 186 $F_{5:8}$ RILs are obtained from the HS200×STG-001 cross while 140 $F_{4:6}$ RILs are obtained from the HS200×STG-002 cross.

Example 2. Cotton STG QTLs Identified from Bi-Parental Mapping

The HS200×STG-001 and HS200×STG-002 mapping populations are used to identify genetic determinants of the STG trait. All plants are phenotyped in field trials using visual ratings on a 1-9 ordinal scale. The leaf color rating ranging from dark-green (rating 1) to light-yellow (rating 9) and levels of wilting are described in Table 1.

Progenies from HS200×STG-002 are phenotyped at four locations distributed in Texas, New Mexico and Arizona in 2011 in an RCB design with three replications. Progenies from HS200×STG-001 are phenotyped in 2010 at two locations in New Mexico and Texas in an RCB design with two replications. Leaf tissues are collected for genotyping.

Both phenotypic and genotypic data are pre-processed prior to marker-trait association analysis. The repeatability of the staygreen phenotyping is estimated using the variance component. Data are diagnosed for influential outlier observations using the studentized deleted residuals and Cook's Distance metrics. Effectiveness of the outlier removal is assessed by comparing the repeatability before and after data quality check. Experiment sets that have repeatability lower than 30% are dropped from the analysis. Log-transformation is applied to the raw data to approximate normal distribution. For each entry, an adjusted mean is estimated following data quality check.

Polymorphic markers having less than 15% of missing data are selected for QTL mapping. The QTL analysis is completed using the R/qtl package (Broman et al., R/qtl:

QTL mapping in experimental crosses. *Bioinformatics,* 19:889-90, (2003)). A MQM (Multiple QTL model) approach is used, which is implemented in three main steps: 1) missing genotypes are imputed and assigned a probability used as a weight in later analysis; 2) co-factors are selected genome-wide by multiple regression and backward elimination; 3) QTL scan across the genome using the co-factors selected in step 2 (Arends et al., R/qtl: high throughput multiple QTL mapping. *Bioinformatics,* 26:2990-92 (2010)). QTL empirical significance threshold is estimated after 1000 permutations. The putative position of the QTL is estimated at the point of maximum LOD score. The QTL confidence interval is estimated using the 1.5-LOD drop support interval and the Bayesian credible interval estimate method. The phenotypic variance explained by a QTL is estimated as the square of the partial correlation coefficient (r-squared) with the staygreen rating, adjusted for co-factors. QTL additive effect is also estimated.

TABLE 1

A staygreen (STG) rating system used to phenotype plants that are fully loaded with green bolls and exhibit water stress symptoms such as wilting. Cotton plants with an STG rating of 1 to 4 are categorized as having a staygreen trait. An STG rating of 5 corresponds to a moderate staygreen trait, while an STG rating of 6 to 9 represents a non-staygreen plant.

| STG Rating | Corresponding RHS color scale | Wilting status |
|---|---|---|
| 1 | 135B | Light to no |
| 2 | 134A | wilting |
| 3 | 140A | |
| 4 | 140B | Moderate |
| 5 | 142A | wilting |
| 6 | 142B | |
| 7 | 143D | Complete |
| 8 | 145C | wilting |
| 9 | 145D | |

A total of 1462 informative markers spanning 5260 cM are selected for QTL mapping in the HS200×STG-001 population. The average marker spacing is 3.7 cM. The repeatability of the STG rating across locations and replications is 0.44. Two significant QTL are identified on chromosome A11 (11) and D06 (19) (Table 2).

A smaller set of 146 informative markers spanning only 2298 cM are identified for QTL mapping in the HS200×STG-002 population. As a result, a wider average marker spacing of 21.7 cM is obtained. The repeatability of the STG rating across locations and replications is 0.57. Two minor effect QTLs and two stronger effect QTLs are identified in this population. The support interval of the strong effect QTLs overlap with the two QTLs identified from population HS200×STG-001 (Table 2). Some of the most significant markers in the QTL intervals on chromosomes A11 and D06 are listed in Table 3.

TABLE 2

Average parameters of two staygreen QTLs identified in two bi-parental mapping populations HS200xSTG-001 and HS200xSTG-002. The QTL support-interval indicates the interval which overlaps between the two populations. PVE represents Percent of Variance Explained.

| STG QTL No. | Chromosome | QTL support-interval (cM) | LOD | PVE (%) | Additive Effect |
|---|---|---|---|---|---|
| 1 | A11 | 98-180 | 5.8 | 14.0 | 0.61 |
| 2 | D06 | 87-128 | 10.6 | 18.5 | 0.64 |

TABLE 3

Markers in staygreen QTL intervals on chromosomes A11 and D06 and associated with STG QTL No. 1 or 2. These markers are estimated from bi-parental population HS200xSTG-002 where marker density is higher.

| Marker SEQ ID | STG QTL No. | Chromosome | Position (cM) | Length | SNP position | LOD score | p value | Additive effect | Representative STG allele | Representative Non-STG allele | Marker Start on Cotton gossypium__ hirsutum tm1__NBI__V1. 1 | Marker End on Cotton gossypium__ hirsutum tm1__NBI__V1.1 |
|---|---|---|---|---|---|---|---|---|---|---|---|---|
| 1 | 1 | A11 | 113.8 | 121 | 61 | 4.3 | 0.005251 | 0.38 | A | G | 16313936 | 16314056 |
| 2 | 1 | A11 | 140.7 | 121 | 61 | 5.2 | 0.001205 | 0.5 | A | G | 17681669 | 17681789 |
| 3 | 1 | A11 | 142.8 | 121 | 61 | 5.1 | 0.001474 | 0.49 | A | C | 17563460 | 17563580 |
| 4 | 1 | A11 | 143.9 | 594 | 440 | n/d | 0.002308 | 0.4525 | T | C | 17830791 | 17831384 |
| 5 | 1 | A11 | 166.5 | 121 | 61 | 0.3 | 0.001965 | 0.48 | C | T | 18024985 | 18024865 |
| 6 | 1 | A11 | 168.1 | 121 | 61 | 0.3 | 0.003176 | 0.46 | A | G | 18635512 | 18635632 |
| 7 | 1 | A11 | 171.2 | 121 | 61 | n/d | 1.02E−05 | 0.563 | A | G | 18143190 | 18143310 |
| 8 | 2 | D06 | 92.6 | 121 | 61 | n/d | 8.00E−15 | 0.884 | A | G | 44503491 | 44503371 |
| 9 | 2 | D06 | 95.5 | 121 | 61 | 3.9 | 1.04E−07 | 0.69 | G | A | 48721942 | 48721822 |
| 10 | 2 | D06 | 99.3 | 121 | 61 | 12.3 | 3.13E−07 | 0.68 | G | A | 50174908 | 50174788 |
| 11 | 2 | D06 | 99.8 | 601 | 224 | n/d | 1.09E−15 | 0.933 | I | D | 44447447 | 44446848 |
| 12 | 2 | D06 | 103.2 | 121 | 61 | 12.7 | 4.14E−08 | 0.7 | A | G | 41287100 | 41286980 |
| 13 | 2 | D06 | 105.5 | 121 | 61 | n/d | 4.93E−15 | 0.885 | G | A | 39212924 | 39213044 |
| 14 | 2 | D06 | 105.6 | 121 | 61 | 12.6 | 4.14E−08 | 0.7 | G | T | 37595394 | 37595274 |
| 15 | 2 | D06 | 114.5 | 121 | 61 | 12.1 | 1.91E−08 | 0.69 | C | T | 37116513 | 37116393 |
| 16 | 2 | D06 | 117.1 | 676 | 292 | 12 | 1.91E−08 | 0.69 | T | G | 30611001 | 30611676 |
| 17 | 2 | D06 | 124.8 | 508 | 104 | 11.8 | 3.58E−08 | 0.69 | C | A | 33905839 | 33906345 |

Example 3. Analysis of the QTL Efficacy and Yield Equivalency in Field Trials The two staygreen QTLs identified from bi-parental populations mapping (STG QTL Nos. 1 and 2) are evaluated for their impact on agronomic traits such as yield and fiber quality. A panel consisting of 195 $F_4$ and $F_6$ plants derived from three crosses STG-001/NSTG-001, STG-001/NSTG-002 and STG-001/NSTG-003 and seven checks is developed for field trials. In 2012, plants are observed under high water stress at 3-4 locations in Texas. Ten traits of interest including staygreen rating, yield, and various fiber quality traits are measured. In 2013, a subset of 59 plants from this panel are phenotyped for the same ten traits at three locations in Texas under low water stress. All $F_4$ and $F_6$ plants are genotyped with STG-linked markers from chromosomes A11 and D06 (STG QTLs 1 and 2 from Table 1).

A new set of markers are developed in an effort to saturate both QTL regions. After a single marker analysis, two most significant markers (SEQ ID NO: 4 and SEQ ID NO: 7) from STG QTL 1 region (on chromosome A11) and three most significant markers (SEQ ID NO: 8, SEQ ID NO: 11 and SEQ ID NO: 13) from STG QTL 2 region (on chromosome D06) are identified. For each of the two QTLs, the combined genotype from these markers are used to estimate the positive/negative (staygreen/non-staygreen) status of each individual based on whether they carry the STG favorable alleles or unfavorable alleles, respectively.

Under high water stress, the STG individuals (POS) display an average STG rating of 3.2±0.3 versus 5.9±0.3 for non-staygreen (NSTG) individuals (FIG. 1, Table 4). A 12% yield advantage for STG plants over NSTG plants is observed. The boll open percent is significantly lower in STG individuals.

Figure 2:
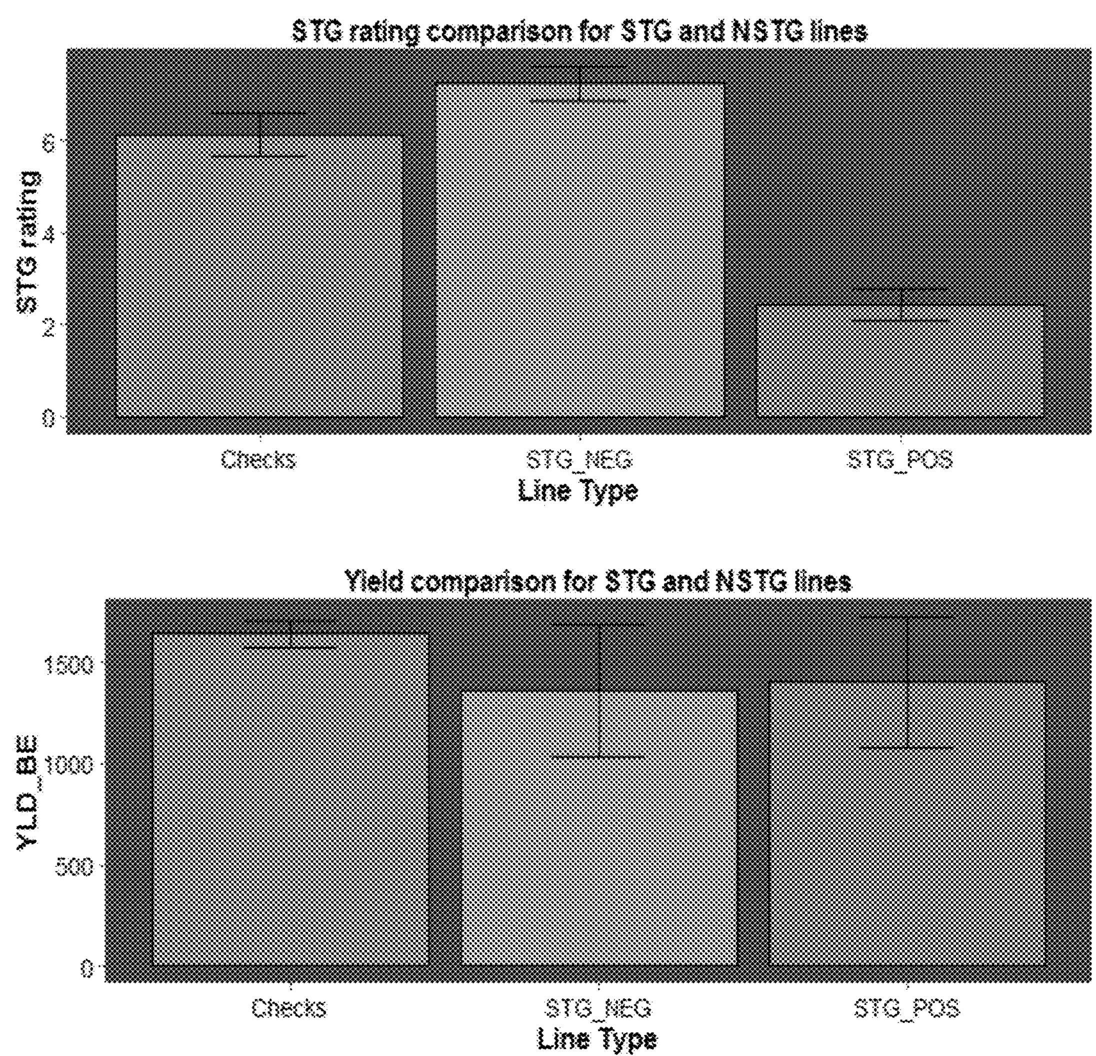
FIG. 2 shows the STG index and yield of staygreen and non-staygreen plants under low moisture stress. STG_POS: staygreen individuals based on genotype at QTL1 and QTL2; STG_NEG: non-staygreen individuals based on genotype at QTL1 and QTL2.

Under low moisture stress, a significant difference between STG and NSTG plants for staygreen index is also observed. No significant difference is observed for yield between the two groups, thus indicating absence of yield penalty (FIG. 2, Table 5).

TABLE 4

Summary of STG effects on various traits under high water stress. STG_POS: staygreen individuals based on genotype at QTL1 and QTL2; STG_NEG: non-staygreen individuals based on genotype at QTL1 and QTL2. Checks represent plants from a set of top performing lines.

| Trait | | STG_POS | STG_NEG | Checks |
|---|---|---|---|---|
| Staygreen Index | Mean | 3.22 | 5.94 | 6.97 |
| Rating | Standard error | 0.29 | 0.27 | 0.09 |
| Yield (kg/ha) | Mean | 398.61 | 357.02 | 465.9 |
| | Standard error | 30.48 | 30.33 | 7.47 |
| Micronaire | Mean | 4.56 | 4.55 | 4.45 |
| (μg/inch) | Standard error | 0.08 | 0.08 | 0.02 |
| Bolls open % | Mean | 19.81 | 38.45 | 24.86 |
| | Standard error | 2.43 | 2.35 | 0.99 |
| Elongation (%) | Mean | 8.11 | 7.49 | 7.97 |
| | Standard error | 0.2 | 0.19 | 0.08 |
| Fiber Maturity | Mean | 85.41 | 85.87 | 85.26 |
| Ratio (%) | Standard error | 0.17 | 0.15 | 0.08 |
| Short Fiber | Mean | 8.07 | 8.99 | 8.92 |
| Content (%) | Standard error | 0.71 | 0.71 | 0.15 |
| Fiber Length (cm) | Mean | 1.07 | 1.08 | 1.12 |
| | Standard error | 0.02 | 0.02 | 0 |
| Fiber Strength(g/ | Mean | 27.48 | 27.35 | 27.28 |
| tex) | Standard error | 0.5 | 0.48 | 0.17 |
| Uniformity Index | Mean | 81.75 | 80.92 | 81.18 |
| | Standard error | 0.42 | 0.41 | 0.13 |
| Lint Percent | Mean | 38.03 | 39.15 | 41.41 |
| (%) | Standard error | 0.42 | 0.39 | 0.17 |

TABLE 5

Summary of STG effects on various traits under low moisture stress.

| Trait | | STG_POS | STG_NEG | Checks |
|---|---|---|---|---|
| Staygreen Index | Mean* | 2.45 | 7.24 | 6.13 |
| Rating | Standard error* | 0.33 | 0.36 | 0.46 |
| Yield (kg/ha) | Mean | 1402.67 | 1360.37 | 1640.72 |
| | Standard error | 321.87 | 323.26 | 65.95 |
| Micronaire | Mean | 4.25 | 4.60 | 4.16 |
| (μg/inch) | Standard error | 0.22 | 0.22 | 0.05 |
| Bolls open % | Mean | 52.62 | 59.73 | 46.23 |
| | Standard error | 5.84 | 5.97 | 2.66 |
| Elongation (%) | Mean | 9.21 | 8.44 | 8.11 |
| | Standard error | 0.34 | 0.36 | 0.11 |
| Fiber Maturity | Mean | 83.90 | 85.38 | 84.57 |
| Ratio (%) | Standard error | 0.38 | 0.39 | 0.10 |
| Short Fiber | Mean | 6.66 | 7.78 | 7.05 |
| Content | Standard error | 0.27 | 0.29 | 0.10 |
| Fiber Length (cm) | Mean | 1.13 | 1.11 | 1.20 |
| | Standard error | 0.02 | 0.02 | 0.00 |
| Fiber Strength(g/ | Mean | 28.46 | 29.26 | 30.44 |
| tex) | Standard error | 0.70 | 0.72 | 0.21 |
| Uniformity Index | Mean | 83.99 | 83.02 | 83.51 |
| | Standard error | 0.42 | 0.43 | 0.14 |
| Lint Percent | Mean | 38.12 | 41.33 | 39.77 |
| (%) | Standard error | 0.71 | 0.75 | 0.25 |

*staygreen index is estimated in only one location of the three locations. STG_POS: staygreen individuals; STG_NEG: non-staygreen individuals.

Example 4. Additional STG QTLs and STG-Associated Markers Identified Through Genome Wide Association Study (GWAS)

A genome wide association approach is taken to identify additional STG QTLs. A total of 229 cotton lines are included in an association panel. Phenotypic data are collected in 2014 at La Mesa, Tex. and Tarzan, Tex. using an RCB design with three replications. The association panel is genotyped with the Cotton Infinium fingerprinting platform comprising a consensus map assembly of 16,900 markers. Minimum allele frequency required for marker inclusion in the analysis is 0.05. Pairwise identity-by-state (IBS) among all individuals is estimated and one individual is selected in a pair with IBS greater than 0.95. Highly heterozygous markers are dropped from the analysis. Individuals and markers with 10% or more missing data are also discarded.

The association analysis is carried out using the R package GenABEL (Aulchenko et al., GenABEL: an R library for genome-wide association analysis. *Bioinformatics* 23:1294-1296(2007)). A principal component analysis method is used to correct for population structure. See Patterson et al., Population structure and eigenanalysis. *PLoS Genetics* 2:e190 (2006); Price et al., Principal components analysis corrects for stratification in genome-wide association studies. *Nature Genetics,* 38:904-909 (2006). The genetic relatedness between every pair of individuals is included in the linear mixed model directly in order to correct for relatedness among individuals (Yu et al., A unified mixed-model method for association mapping that accounts for multiple levels of relatedness. *Nature Genetics,* 38:203-208 (2006)). Multiple testing adjustment is performed by FDR and 1000 permutations. Following the single marker regression approach and taking into account population structure and kinship adjustments and FDR correction, three most significant STG-associated markers are identified as SEQ ID NO: 38, SEQ ID NO: 37 and SEQ ID NO: 39. All three markers are closely linked on chromosome A11 (11).

A penalized elastic net regression is also performed to select the most important markers in high dimensional multiple regression model when p>n. See Waldmann et al., Evaluation of the lasso and the elastic net in genome-wide association studies. Front *Genetics,* 4:1-11(2013). A bootstrap aggregating of the Elastic Net over 1000 resamples is also conducted to assess marker selection stability (Motyer et al., LASSO model selection with post-processing for a genome-wide association study data set. *BMC Proceedings,* 2011, 5(Suppl 9):S24 (2011)). From the elastic-net bootstrap aggregating (bagging) obtained from 1000 resampling, the same markers previously identified on chromosome A11 are again identified. Based on a minimum 10% marker selection rate, five regions were identified as significant on chromosome A7 (7), A10 (10) and D10 (23). Table 6 summarizes the p values and additive effect associated with significant markers in each QTL region. The five QTL regions cumulatively account for 25% of STG trait variation.

TABLE 6

Summary of significant markers in the five stay-green QTL regions identified by genome-wide association study.

| STG QTL No. | Chromosome | Marker SEQ ID | Position | P value | Additive effect | R-Squared | Representative STG allele | Representative Non-STG allele | Marker Start on Cotton gossypium_hirsutum tm1_NBI_V1.1 | Marker End on Cotton gassypium_hirsutum tm1_NBI_V1.1 |
|---|---|---|---|---|---|---|---|---|---|---|
| 3 | 7 | 18 | 31.6 | 0.038365 | 0.18 | 0.009 | A | C | 74540356 | 74540236 |
| | (A07) | 19 | 42.3 | 4.78E−05 | 0.34 | 0.047 | C | T | 72799498 | 72799378 |
| | | 20 | 44.6 | 0.000432 | 0.27 | 0.024 | G | A | 72966662 | 72966832 |
| | | 21 | 50.6 | 0.048401 | 0.11 | 0.020 | A | T | 71200744 | 71200864 |
| 4 | 10 | 22 | 9.6 | 0.000727 | 0.27 | 0.052 | A | G | 99730279 | 99730159 |
| | (A10) | 23 | 10.5 | 0.001107 | 0.31 | 0.032 | G | A | 99860962 | 99860842 |
| | | 24 | 11.2 | 7.69E−05 | 0.31 | 0.079 | T | A | 99706246 | 99706854 |
| | | 25 | 13.2 | 7.69E−05 | 0.31 | 0.079 | G | T | 99440284 | 99439654 |
| | | 26 | 13.3 | 6.1E−05 | 0.31 | 0.079 | A | T | 99254682 | 99254801 |
| | | 27 | 15.3 | 7.69E−05 | 0.31 | 0.079 | C | T | 98715782 | 98716031 |
| | | 28 | 15.3 | 7.69E−05 | 0.31 | 0.079 | A | G | 98878968 | 98879650 |
| 5 | 10 | 29 | 114.1 | 0.016191 | 0.10 | 0.029 | C | A | 66317542 | 66317662 |
| | (A10) | 30 | 119.5 | 0.048561 | 0.11 | 0.007 | C | T | 58297911 | 58297791 |
| | | 31 | 119.6 | 0.030426 | 0.12 | 0.007 | T | A | 58584947 | 58584827 |
| | | 32 | 121.1 | 0.002092 | 0.41 | 0.054 | A | G | 56792293 | 56792691 |
| 6 | 11 | 33 | 90.9 | 7.11E−06 | 0.39 | 0.046 | C | G | 16899868 | 16899988 |
| | (A11) | 34 | 92.5 | 4.96E−05 | 0.37 | 0.041 | T | C | 16861573 | 16861453 |
| | | 35 | 93.5 | 3.28E−05 | 0.38 | 0.041 | G | A | 16995153 | 16995033 |
| | | 36 | 94.4 | 3.09E−05 | 0.36 | 0.043 | T | C | 16943062 | 16943640 |
| | | 37 | 95 | 4.72E−08 | 0.40 | 0.087 | A | G | 17078051 | 17077931 |
| | | 38 | 95.7 | 4.72E−08 | 0.40 | 0.087 | T | A | 17093309 | 17093429 |
| | | 39 | 96.2 | 1.37E−06 | 0.36 | 0.072 | C | T | 17177192 | 17177072 |
| | | 40 | 109.2 | 0.327838 | 0.06 | 0.003 | C | A | 18625457 | 18625577 |
| 7 | 23 | 41 | 179.7 | 0.009575 | 0.10 | 0.021 | A | G | 1477376 | 1477496 |
| | (D10) | 42 | 180.5 | 0.011431 | 0.10 | 0.022 | A | G | 1216074 | 1215954 |
| | | 43 | 183 | 0.000585 | 0.17 | 0.061 | A | G | 937786 | 937665 |
| | | 44 | 186.4 | 0.003075 | 0.12 | 0.033 | C | T | 952944 | 953064 |

Example 5. Introgression of an STG Trait into Additional Cotton Varieties

A cotton plant comprising any one of the identified STG QTLs is crossed with an elite cotton line comprising a desirable trait (e.g., improved yield under drought, cold, heat stress conditions) but having no STG trait. $F_1$ progeny plants from this cross are assayed for one or more SNP markers exemplified in Table 3 or any markers that are associated with these SNP markers to select for an STG QTL. A selected $F_1$ progeny plant is then backcrossed with the parent elite cotton line comparing the desirable trait (recurrent parent). Plants from the BC1 generation are also genotyped using SNP markers exemplified in Table 1 or other associated markers to select for the STG QTL. After multiple rounds of backcrossing (e.g., 5-7 generations), a new elite cotton line is obtained comparing both the STG trait and the desirable trait in the recurrent parent elite line.

As various modifications could be made in the constructions and methods herein described and illustrated without departing from the scope of the disclosure, it is intended that all matter contained in the foregoing description or shown in the accompanying drawings shall be interpreted as illustrative rather than limiting. The breadth and scope of the present disclosure should not be limited by any of the above-described exemplary embodiments, but should be defined only in accordance with the following claims appended hereto and their equivalents. All patent and non-patent documents cited in this specification are incorporated herein by reference in their entireties.

DEPOSIT INFORMATION

Applicant has made a deposit of at least 2500 seeds for each of cotton varieties STG-001 and STG-002 disclosed herein with the American Type Culture Collection (ATCC), 10801 University Boulevard, Manassas, Va. 20110-2209 USA. The deposit accession numbers for varieties STG-001 and STG-002 are ATCC Accession Nos. PTA-122486 and PTA-122487. The date of deposit was Aug. 24, 2015. Access to the deposits will be available during the pendency of the application to the Commissioner of Patents and Trademarks and persons determined by the Commissioner to be entitled thereto upon request. The deposits will be maintained for a period of 30 years, or 5 years after the most recent request, or for the enforceable life of the patent, whichever is longer, and will be replaced if they become nonviable during that period. Applicant does not waive any infringement of rights granted under this patent or under the Plant Variety Protection Act (7 U.S.C. 2321 et seq.).

What is claimed is:

1. A method of creating a population of cotton plants or seeds, said method comprising the steps of:

a. identifying in a first population of staygreen (STG) cotton plants or seeds, cotton plants having at least one marker linked within 3.0 cM to at least one haplotype comprising three or more representative STG alleles in at least one polymorphic locus;

b. selecting from said first population one or more cotton plants or seeds comprising said at least one marker linked to said at least one haplotype comprising three or more representative STG alleles; and c. crossing said selected one or more cotton plants or seeds to produce a second population of cotton plants or seeds comprising an STG phenotype and said at least one haplotype comprising three or more representative STG alleles;

wherein said haplotype comprises three representative STG alleles of the haplotype of quantitative trail locus (QTL) 1 selected from the group consisting of:

an A nucleotide at position 61 of SEQ ID NO:1,
an A nucleotide at position 61 of SEQ ID NO:2,
an A nucleotide at position 61 of SEQ ID NO:3,
a T nucleotide at position 440 of SEQ ID NO:4,
a C nucleotide at position 61 of SEQ ID NO:5,
an A nucleotide at position 61 of SEQ ID NO:6, and
an A nucleotide at position 61 of SEQ ID NO:7, the haplotype of QTL 2 selected from the group consisting of: an A nucleotide at position 61 of SEQ ID NO:8,
a G nucleotide at position 61 of SEQ ID NO:9,
a G nucleotide at position 61 of SEQ ID NO:10,
an insertion beginning at position 224 of SEQ ID NO:11,
an A nucleotide at position 61 of SEQ ID NO:12,
a G nucleotide at position 61 of SEQ ID NO:13,
a G nucleotide at position 61 of SEQ ID NO:14,
a C nucleotide at position 61 of SEQ ID NO:15,
a T nucleotide at position 292 of SEQ ID NO:16, and
a C nucleotide at position 104 of SEQ ID NO:17;

the haplotype of QTL 3 selected from the group consisting of:

an A nucleotide at position 61 of SEQ ID NO:18,
a C nucleotide at position 61 of SEQ ID NO:19,
a G nucleotide at position 50 of SEQ ID NO:20, and
an A nucleotide at position 61 of SEQ ID NO:21;

the haplotype of QTL 4 selected from the group consisting of:

an A nucleotide at position 61 of SEQ ID NO:22,
a G nucleotide at position 61 of SEQ ID NO:23,
a T nucleotide at position 230 of SEQ ID NO:24,
a G nucleotide at position 61 of SEQ ID NO:25,
an A nucleotide at position 61 of SEQ ID NO:26,
a C nucleotide at position 150 of SEQ ID NO:27, and
an A nucleotide at position 391 of SEQ ID NO:28;

the haplotype of QTL 5 selected from the group consisting of:

a C nucleotide at position 61 of SEQ ID NO:29,
a C nucleotide at position 61 of SEQ ID NO:30,
a T nucleotide at position 61 of SEQ ID NO:31,
and an A nucleotide at position 230 of SEQ ID NO:32;

the haplotype of QTL 6 selected from the group consisting of:

a C nucleotide at position 61 of SEQ ID NO:33,
a T nucleotide at position 61 of SEQ ID NO:34,
a G nucleotide at position 61 of SEQ ID NO:35,
a T nucleotide at position 156 of SEQ ID NO:36,
an A nucleotide at position 61 of SEQ ID NO:37,
a T nucleotide at position 61 of SEQ ID NO:38,
a C nucleotide at position 61 of SEQ ID NO:39, and
a C nucleotide at position 61 of SEQ ID NO:40; or the haplotype of QTL 7 selected from the group consisting of:

an A nucleotide at position 61 of SEQ ID NO:41;
an A nucleotide at position 61 of SEQ ID NO:42,
an A nucleotide at position 61 of SEQ ID NO:43; and
a C nucleotide at position 61 of SEQ ID NO:44.

2. The method of claim 1, wherein said at least one marker is located in a chromosomal haplotype flanked by:

any two polymorphic loci selected from the group consisting of SEQ ID NOs: 1 to 7;

any two polymorphic loci elected from the group consisting of SEQ ID NOs: 8 to 17;

any two polymorphic loci selected from the group consisting of SEQ ID NOs: 18 to 21;
any two polymorphic loci selected from the group consisting of SEQ ID NOs: 22 to 28;
any two polymorphic loci selected from the group consisting of SEQ ID NOs: 29 to 32;
any two polymorphic loci selected from the group consisting of SEQ ID NOs: 33 to 40,
any two polymorphic loci selected from the group consisting of SEQ ID NOs: 41 to 44, or combinations thereof.

3. The method of claim 1, wherein said at least one marker is within said at least one haplotype comprising three or more representative STG alleles.

4. The method of claim 1, wherein said at least one haplotype comprising three or more representative STG alleles confers no seed or fiber yield penalty under water-sufficient conditions.

5. The method of claim 4, wherein the seed or fiber yield under water-limited conditions of cotton plants comprising said representative STG allele is 3% or more higher than the seed or fiber yield of cotton plants without said at least one haplotype comprising three or more representative STG alleles under water-limited conditions.

6. The method of claim 1, further comprising producing said first population of cotton plants or seeds by crossing a first cotton plant comprising at least one haplotype comprising three or more representative STG alleles, with a second cotton plant that does not comprise said at least one haplotype comprising three or more representative STG alleles of said first cotton plant.

7. The method of claim 4, wherein said at least one haplotype comprising three or more representative STG alleles has no impact in said second population of cotton plants or seeds over at least one or more traits at maturity selected from the group consisting of plant height, micronaire, bolls open percentage, fiber elongation percentage, fiber maturity ratio, short fiber content, fiber length, fiber strength, uniformity index, lint percentage, and stringout rating, under either water-limited conditions or water-sufficient conditions.

8. The method of claim 1, wherein said method comprises selecting cotton plants or seeds for at least two markers linked within 3.0 cM to at least two different haplotypes comprising three or more representative STG alleles loci.

9. The method of claim 8, wherein at least three markers are linked with at least three different STG QTL haplotypes selected from the group consisting of STG QTL haplotypes 1 to 7.

10. A method for selecting a cotton plant or seed comprising a representative staygreen (STG) allele, said method comprising:

a. crossing an STG cotton plant, comprising at least one haplotype comprising three or more representative STG alleles, to a second cotton plant lacking said haplotype;
b. detecting a marker linked within 3.0 centimorgan (cM) of said at least one haplotype comprising three or more representative STG alleles in a progeny cotton plant produced from said cross; and
c. selecting said progeny cotton plant or seed comprising said haplotype comprising three or more representative STG alleles;

wherein said haplotype comprises three representative STG alleles of the haplotype of quantitative trail locus (QTL) 1 selected from the group consisting of:
an A nucleotide at position 61 of SEQ ID NO:1,
an A nucleotide at position 61 of SEQ ID NO:2,
an A nucleotide at position 61 of SEQ ID NO:3,
a T nucleotide at position 440 of SEQ ID NO:4,
a C nucleotide at position 61 of SEQ ID NO:5,
an A nucleotide at position 61 of SEQ ID NO:6, and
an A nucleotide at position 61 of SEQ ID NO:7,
the haplotype of QTL 2 selected from the group consisting of: an A nucleotide at position 61 of SEQ ID NO:8,
a G nucleotide at position 61 of SEQ ID NO:9,
a G nucleotide at position 61 of SEQ ID NO:10,
an insertion beginning at position 224 of SEQ ID NO:11,
an A nucleotide at position 61 of SEQ ID NO:12,
a G nucleotide at position 61 of SEQ ID NO:13,
a G nucleotide at position 61 of SEQ ID NO:14,
a C nucleotide at position 61 of SEQ ID NO:15,
a T nucleotide at position 292 of SEQ ID NO:16, and
a C nucleotide at position 104 of SEQ ID NO:17;
the haplotype of QTL 3 selected from the group consisting of:
an A nucleotide at position 61 of SEQ ID NO:18,
a C nucleotide at position 61 of SEQ ID NO:19,
a G nucleotide at position 50 of SEQ ID NO:20, and
an A nucleotide at position 61 of SEQ ID NO:21;
the haplotype of QTL 4 selected from the group consisting of:
an A nucleotide at position 61 of SEQ ID NO:22,
a G nucleotide at position 61 of SEQ ID NO:23,
a T nucleotide at position 230 of SEQ ID NO:24,
a G nucleotide at position 61 of SEQ ID NO:25,
an A nucleotide at position 61 of SEQ ID NO:26,
a C nucleotide at position 150 of SEQ ID NO:27, and
an A nucleotide at position 391 of SEQ ID NO:28;
the haplotype of QTL 5 selected from the group consisting of:
a C nucleotide at position 61 of SEQ ID NO:29,
a C nucleotide at position 61 of SEQ ID NO:30,
a T nucleotide at position 61 of SEQ ID NO:31,
and an A nucleotide at position 230 of SEQ ID NO:32;
the haplotype of QTL 6 selected from the group consisting of:
a C nucleotide at position 61 of SEQ ID NO:33,
a T nucleotide at position 61 of SEQ ID NO:34,
a G nucleotide at position 61 of SEQ ID NO:35,
a T nucleotide at position 156 of SEQ ID NO:36,
an A nucleotide at position 61 of SEQ ID NO:37,
a T nucleotide at position 61 of SEQ ID NO:38,
a C nucleotide at position 61 of SEQ ID NO:39, and
a C nucleotide at position 61 of SEQ ID NO:40; or
the haplotype of QTL 7 selected from the group consisting of:
an A nucleotide at position 61 of SEQ ID NO:41;
an A nucleotide at position 61 of SEQ ID NO:42,
an A nucleotide at position 61 of SEQ ID NO:43; and
a C nucleotide at position 61 of SEQ ID NO:44.

11. The method of claim 10, wherein said marker is located in a chromosomal haplotype flanked by:
any two polymorphic loci selected from the group consisting of SEQ ID NOs: 1 to 7;
any two polymorphic loci elected from the group consisting of SEQ ID NOs: 8 to 17;
any two polymorphic loci selected from the group consisting of SEQ ID NOs: 18 to 21;
any two polymorphic loci selected from the group consisting of SEQ ID NOs: 22 to 28;
any two polymorphic loci selected from the group consisting of SEQ ID NOs: 29 to 32;

any two polymorphic loci selected from the group consisting of SEQ ID NOs: 33 to 40, or any two polymorphic loci selected from the group consisting of SEQ ID NOs: 41 to 44.

12. The method of claim 1, wherein said at least one marker is within 1 cM of said haplotype comprising three or more representative STG alleles.

13. The method of claim 10, wherein said marker is within 1 cM of said haplotype comprising three or more representative STG alleles.

14. The method of claim 2, wherein said any two polymorphic loci are SEQ ID NOs: 4 and 5.

15. The method of claim 2, wherein said any two polymorphic loci are SEQ ID NOs: 16 and 17.

16. The method of claim 1, further comprising producing said first population of cotton plants or seeds by crossing a first cotton plant comprising at least one haplotype comprising three or more representative STG alleles linked with a polymorphic locus selected from the group consisting of SEQ ID NOs: 1 to 44, with a second cotton plant comprising a different at least one haplotype comprising three or more representative STG alleles linked with a polymorphic locus selected from the group consisting of SEQ ID NOs: 1 to 44; wherein each said polymorphic locus is linked with a different STG QTL haplotype selected from the group consisting of STG QTL haplotypes 1 to 7.

17. The method of claim 16, wherein said second cotton plant comprises at least two different haplotypes comprising three or more representative STG alleles in at least two polymorphic loci selected from the group consisting of SEQ ID NOs: 1 to 44, wherein said polymorphic loci are linked with at least two different STG QTL haplotypes selected from the group consisting of STG QTL haplotypes 1 to 7.

18. The method of claim 16, wherein said second cotton plant comprises at least three different haplotypes comprising three or more a representative STG allele in at least three polymorphic loci selected from the group consisting of SEQ ID NOs: 1 to 44, wherein said polymorphic loci are linked with at least three different STG QTL haplotypes selected from the group consisting of STG QTL haplotypes 1 to 7.

* * * * *